(12) United States Patent
Chow et al.

(10) Patent No.: US 11,434,537 B2
(45) Date of Patent: Sep. 6, 2022

(54) BIOMARKER FOR PROGNOSIS OF COLORECTAL CANCER

(71) Applicant: NATIONAL CHENG KUNG UNIVERSITY, Tainan (TW)

(72) Inventors: Nan-Haw Chow, Tainan (TW);
Chien-An Chu, Tainan (TW);
Hsiao-Sheng Liu, Tainan (TW);
Chung-Ta Lee, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 61 days.

(21) Appl. No.: 16/790,804

(22) Filed: Feb. 14, 2020

(65) Prior Publication Data
US 2021/0262036 A1 Aug. 26, 2021

(51) Int. Cl.
*C12Q 1/6886* (2018.01)
*C12Q 1/686* (2018.01)

(52) U.S. Cl.
CPC .......... *C12Q 1/6886* (2013.01); *C12Q 1/686* (2013.01); *C12Q 2531/113* (2013.01); *C12Q 2561/113* (2013.01); *C12Q 2600/158* (2013.01); *G01N 2800/52* (2013.01)

(58) Field of Classification Search
CPC .................. C12Q 1/6886; C12Q 1/686; C12Q 2531/113; C12Q 2561/113; C12Q 2600/158; G01N 2800/52
See application file for complete search history.

(56) References Cited

PUBLICATIONS

Avissar et al., "MicroRNA Expression Ratio Is Predictive of Head and Neck Squamous Cell Carcinoma," Clinical Cancer Research, Apr. 15, vol. 15, No. 8, pp. 2850-2855. (Year: 2009).*
Ju et al., "Characterization of a colorectal cancer migration and autophagy-related microRNA miR-338-5p and its target gene PIK3C3," Biomarkers and Genomic Medicine, vol. 5, pp. 74-78. (Year: 2013).*
Gen Bank Accession No. NR_029897 [retrieved on-line, retrieval date, Aug. 12, 2021; retrieved from https://www.ncbi.nlm.nih.gov/nucleotide/NR_029897.1?report=genbank&log$=nuclalign&blast_rank=41&RID=HBFPMUYS016], (Year: 2021).*
Gen Bank Accession No. NM_002647 [retrieved on-line, retrieval date, Aug. 12, 2021; retrieved from https://www.ncbi.nlm.nih.gov/nuccore/NM_002647.4], (Year: 2021).*
Gopalan et al., "Regulation of microRNA-1288 in Colorectal Cancer: Altered Expression and Its Clinicopathological Significance," Molecular Carcinogenesis, vol. 53, pp. E36-E44. (Year: 2014).*
Jarzab et al., "Ratio of proliferation markers and HSP90 gene expression as a predictor of pathological complete response in breast cancer neoadjuvant chemotherapy," Folia Histochemica et Cytobiologica, vol. 54, No. 4, pp. 202-209. (Year: 2016).*
Chu, et al. "MiR-338-5p promotes metastasis of colorectal cancer by inhibition of phosphatidylinositol 3-kinase, catalytic subunit type 3-mediated autophagy pathway", EbioMedicine 43 (2019) 270-281, Available online Apr. 12, 2019.

* cited by examiner

*Primary Examiner* — Young J Kim
(74) *Attorney, Agent, or Firm* — Amin, Turocy & Watson, LLP

(57) ABSTRACT

Provided is a method of accurate and sensitive characterization and prognosis of colorectal cancer in a subject. The method includes obtaining a cancer tissue from the subject and determining the expression level of a miRNA and a target gene of the miRNA. Also provided is a kit for prognosis of colorectal cancer in a subject in need thereof.

8 Claims, 45 Drawing Sheets

Specification includes a Sequence Listing.

HCT116

N.C.

miR-338-5p

SEQUENCE LISTING

```
<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: primer for miRNA

<400> SEQUENCE: 1
aacaatatcc tggtgctgag tgga                                            24

<210> SEQ ID NO 2
<211> LENGTH: 27
<212> TYPE: DNA
<213> ORGANISM: Artificial Sequence
<220> FEATURE:
<223> OTHER INFORMATION: Primer for miRNA u54

<400> SEQUENCE: 2
ggtacctatt gtgttgagta acggtga                                         27

<210> SEQ ID NO 3
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(21)

<400> SEQUENCE: 3
tcgatgtgtc aagtgtgatg a                                               21

<210> SEQ ID NO 4
<211> LENGTH: 21
<212> TYPE: DNA
```

```
<213> ORGANISM: Artificial Sequence
<220> FEATURE:
<223> OTHER INFORMATION: Primer
<220> FEATURE:
<221> NAME/KEY: primer_bind
<222> LOCATION: (1)..(21)

<400> SEQUENCE: 4
ttcagatcgt ggtcagaagg t                                        21

<210> SEQ ID NO 5
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(21)

<400> SEQUENCE: 5
ggcggcacca ccatgtaccc t                                        21

<210> SEQ ID NO 6
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(21)

<400> SEQUENCE: 6
aggggccgga ctcgtcatac t                                        21

<210> SEQ ID NO 7
<211> LENGTH: 22
<212> TYPE: RNA
<213> ORGANISM: Homo sapiens

<400> SEQUENCE: 7
gggcuuguuu ugaaauauug ua                                       22

<210> SEQ ID NO 8
<211> LENGTH: 22
<212> TYPE: RNA
<213> ORGANISM: Artificial Sequence
<220> FEATURE:
<223> OTHER INFORMATION: Artificially mutated sequence for plasmid
      construction
<220> FEATURE:
<221> NAME/KEY: 3'UTR
<222> LOCATION: (1)..(22)
<220> FEATURE:
<221> NAME/KEY: mutation
<222> LOCATION: (15)..(15)
<220> FEATURE:
<221> NAME/KEY: mutation
<222> LOCATION: (17)..(17)
<220> FEATURE:
<221> NAME/KEY: mutation
<222> LOCATION: (19)..(19)
<220> FEATURE:
<221> NAME/KEY: mutation
<222> LOCATION: (21)..(21)

<400> SEQUENCE: 8
gggcuuguuu ugaacuguag ga                                       22
```

BIOMARKER FOR PROGNOSIS OF COLORECTAL CANCER

BACKGROUND

1. Technical Field

The present disclosure relates to biomarkers and methods for prognostic prediction of colorectal cancer in a subject in need thereof. The present disclosure also relates to methods, compositions and kits for prognosing, characterizing and treating colorectal cancer in a subject in need thereof.

2. Description of Related Art

Colorectal cancer (CRC) has become one of the most common types of cancer. In 2018, CRC is the third most common human cancer worldwide with 1,096,601 new reported cases and accounts for 551,269 (5.8%) cancer-related deaths. In Taiwan, CRC is the third leading cause of cancer-related deaths (24.7%) in 2018.

An effective cancer treatment regimen involves many different considerations and strategies. Following the diagnosis of cancer, an informative and accurate characterization of a cancer stage is of crucial importance in determining the proper treatment regimen. For CRC, it is categorized as stages 0 to IV at the time of diagnosis according to tumor, node and metastasis (TNM) system refined by American Joint Committee on Cancer (AJCC). A stage 0 CRC indicates that tumor is confined to mucosa. When cancer cells invade into submucosa or muscularis propria, it is considered stage I. The stage II CRCs are grouped as stage IIA if cancer cells invade to subserosa but has not grown through it, stage IIB if they penetrate the surface of visceral peritoneum, or stage IIC if they directly invade or adhere to other organs or structures. The late stages of CRC comprise stage III when cancer cells spread to lymph nodes and stage VI if they have metastasized to distant organs. Tumor staging is currently the fundamental factor for determining the prognosis of CRC patients, and is the basis for selecting an appropriate treatment regimen.

Most of the time, patients diagnosed with stage I and stage II CRC are recommended to have surgical resection, and patients with stage III CRC are treated with adjuvant chemotherapy in addition to surgery. However, despite the advances in neoadjuvant and adjuvant therapy for CRC, almost half of the CRC patients may still develop recurrent tumor, and some of them may even present with cancer metastasis. For example, stage II CRC patients may still have 25 to 30% of recurrence rate. Furthermore, chemotherapy is ineffective against some of stage III patients. Hence, patients diagnosed with the same stage of CRC can still have very different responses to treatment and thereby distinct prognosis. These facts indicate that conventional stage classification is not sufficient in predicting the prognosis of CRC patients.

Thus, a more reliable biological marker and a more efficient method for determining the prognosis of CRC are needed.

SUMMARY

Herein, the present disclosure is therefore provided with a biomarker and a method to prognosticate the progression or recurrence of CRC in a subject.

In an aspect of the present disclosure, a method for assessing the prognosis of CRC in a subject in need thereof is provided. The method comprises obtaining a cancer tissue from a subject in need thereof; and measuring, by a pair of oligonucleotides, the expression level of at least one miRNA associated with colorectal cancer in the cancer tissue; followed by measuring a second expression level of at least one target gene of the miRNA in cancer tissue by another pair of oligonucleotides; and determining a ratio between the first expression level of the miRNA and the second expression level of the target gene as indicative of prognosis of the colorectal cancer of the subject.

In one embodiment of the present disclosure, the prognosis is indicative of metastatic potential of colorectal cancer, a tumor stage of colorectal cancer, or survival of the subject. In another embodiment of the present disclosure, the prognosis is indicative of metastatic potential of colorectal cancer to the liver, lung, lymph nodes, peritoneum, abdominal wall, small intestine, stomach, pancreas, biliary tract, spleen, uterus, ovary, fallopian tube, head, neck, brain, respiratory organs, skin, bone, and distant soft tissue. In yet another embodiment of the present disclosure, the prognosis is indicative of metastatic potential of colorectal cancer to the liver or lung. In one embodiment of the present disclosure, the prognosis is indicative of survival is recurrence-free survival, disease-free survival, disease-specific survival, overall survival, or metastasis-free survival.

In one embodiment of the present disclosure, the method for assessing the prognosis of CRC in a subject further comprising determining a therapy based on prognosis and treating the subject with therapy. In one embodiment, the therapy is surgery, radiation therapy, chemotherapy, targeted therapy, immunotherapy or a combination thereof.

In one embodiment of the present disclosure, the method for assessing the prognosis of CRC in a subject comprises amplification or hybridization to measure the first expression level and the second expression level. In one embodiment, the first expression level and the second expression are measured by real-time PCR. In another embodiment, the first pair of oligonucleotides used to measure the expression level comprises a sequence of SED ID NO. 1. In another embodiment, the second pair of oligonucleotides used to measure the expression level comprises a sequence of SED ID NO. 2, a sequence of SED ID NO. 3, or a combination thereof.

In an aspect of the present disclosure, a method for assessing the prognosis of CRC in a subject in need thereof comprises measuring the expression level of miRNA-338-5p (miR-338-5p). In another embodiment, a method for assessing the prognosis of CRC in a subject in need thereof comprises measuring the expression level of the target gene encoding a protein selected from the group consisting of sprouty homolog 2 (SPRY2), hemogen (HEMGN), DNA-binding protein inhibitor ID-1 (ID1), DEAD box protein 5 (DDX5), voltage-gated sodium channel NaV1.7 (SCN9A), homeobox protein Hox-A5 (HOXA5), phosphatidylinositol 3-kinase catalytic subunit type 3 (PIK3C3), Ras-related protein Rab-1A (RAB1A), Ras-related protein Rab-28 (RAB28), protocadherin-20 (PCDH20), cullin-2 (CUL2), coiled-coil domain-containing protein 126 (CCDC126), Krueppel-like factor 2 (KLF2), NEDD4 family-interacting protein 1 (NDFIP1), RB1-inducible coiled-coil protein 1 (RB1CC1), phosphatidylinositol N-acetylglucosaminyltransferase subunit P (PIGP), adrenomedullin (ADM), cytoplasmic protein NCK2 (NCK2), ribose-5-phosphate isomerase (RPIA), neurotrophin-3 (NTF3), as-related protein Rab-23 (RAB23), chloride intracellular channel protein 4 (CLIC4), homeobox expressed in ES cells 1 (HESX1), serine/threonine-protein phosphatase 2A 56 kDa regulatory subunit alpha isoform (PPP2R5A), protein Tob1 (TOB1), HORMA domain-containing protein (HORMAD1), E3 ubiquitin-protein ligase RBX1 (RBX1), acidic leucine-rich nuclear phosphoprotein 32 family member E (ANP32E), serine/threonine-protein kinase 17B (STK17B), aryl hydrocarbon receptor nuclear translocator-like protein 2 (ARNTL2), protein inturned (INTU), nuclear receptor subfamily 1 group D member 1 (NR1D1), chromobox protein homolog 3 (CBX3), heparan sulfate glucosamine 3-O-sulfotransferase 5 (HS3ST5), dual specificity protein phosphatase 2 (DUSP2), tetratricopeptide repeat protein 33 (TTC33), fucose-1-phosphate guanylyltransferase (FPGT), melanoma-associated antigen 10 (MAGEA10), cell adhesion molecule 2 (CADM2), E3 ubiquitin-protein ligase RNF170 (RNF170), V-type proton ATPase 116 kDa subunit a isoform 4, V-ATPase 116 kDa isoform a4 (ATP6V0A4), interleukin-22 receptor subunit alpha-2 (IL22RA2) and a combination thereof.

In an aspect of the present disclosure, a method of treating colorectal cancer is provided, comprising administering to a subject in need thereof a composition to counteract a ratio between a first expression level of a miRNA associated with colorectal cancer and a second expression level of a target gene of the miRNA. In one embodiment, the method comprises administering to a subject in need thereof a composition that counteracts the ratio by inhibiting biological activity of the target gene. In another embodiment, the composition counteracts the ratio by enhancing biological activity of the target gene. In yet another embodiment, the composition includes small-inhibitory RNA (siRNA), short hairpin RNA (shRNA), antisense oligonucleotide, antibody or autophagy inducer and inhibitor.

In an aspect of the present disclosure, an artificial oligonucleotide having at least 85% sequence identity to SEQ ID NO. 1, 2 or 3 is provided. In another aspect of the present disclosure, a kit comprising one or more of the artificial oligonucleotides having at least 85% sequence identity to SEQ ID NO. 1, 2 or 3 and a reagent for amplification is provided.

The method of the present disclosure provides an accurate prognostic prediction of CRC by measuring the expression level of at least one miRNA associated with colorectal cancer in the cancer tissue and the expression level of at least one target gene of miRNA in the cancer tissue, and determining a ratio between the first expression level of the miRNA and the second expression level of the target gene as indicative of the prognosis of colorectal cancer of the subject. In another aspect of the present disclosure, a kit comprising multiple oligonucleotides is provided for measuring expression levels of more than one miRNA and more than one target genes of the miRNA, so as to simultaneously determine more than one ratio between the first expression level of the miRNA and the second expression level of the target gene as described above and provide the prognostic prediction of colorectal cancer of the subject.

The method of the present disclosure provides a reliable and accurate prognostication for CRC patients than current method used for staging CRC.

BRIEF DESCRIPTION OF THE DRAWINGS

The present disclosure will become more readily appreciated by reference to the following descriptions in conjunction with accompanying drawings, wherein:

FIG. 1(a) shows the relative expression of miR-338-5p (T/N ratio) in benign polyps and CRC tumor tissues (n=95). FIG. 1(b) shows the relative expression of miR-338-5p (T/N ratio) in benign polyps and CRC tumor tissues across all different stages (n=95). FIG. 1(c) shows the relative expression of miR-338-5p (T/N ratio) in CRC patients of stages I and II compared with stages III and IV. FIG. 1(d) shows the relative expression of miR-338-5p (T/N ratio) in CRC patients of stage M0 compared with M1. FIG. 1 (e) shows the relative expression of miR-338-5p in association with overall survivals of CRC patients less than 3 years versus those of greater than 3 years (n=66). (p-values were analyzed using Mann-Whitney test).

FIG. 2(a) shows the relative RNA expression of PIK3C3 (T/N ratio) in benign polyps and CRC tumor tissues (n=95). FIG. 2(b) shows the relative RNA expression of PIK3C3 (T/N ratio) in benign polyps and CRC tumor tissues cross all different stages (n=95). FIG. 2(c) shows the correlation of miR-338-5p with PIK3C3 mRNA expression (T/N ratio) estimated in polyps and CRC tumor tissues (n=95) using linear regression analyzed by Spearman tests. FIG. 2(d) shows the miR-338-5p/PIK3C3 ratio calculated in benign polyps, early stage (stage I) and late-stages (stages II to IV) of CRC tumor tissues (n=95). Data are presented as median (IQR) with p-values analyzed by Mann-Whitney tests. FIG. 2(e) shows under the curve (AUC) of ROC curves, cutoff values, specificity, and sensitivity for benign polyps and stage I CRC tumor tissues in relation to stages II to IV CRC tumor tissues (n=95). FIG. 2(f) shows the result of Kaplan-Meier analysis using miR-338-5p/PIK3C3 ratio in estimating the overall survival of polyps and CRC patients (n=95) at 6 years after surgery (p-values were analyzed by Log Rank tests).

FIG. 3(a) show the miR-338-5p expressions in SW480, SW620 and HCT116 three different CRC cell lines. The data are shown as means±SEM (n=5). FIG. 3(b) shows the miR-338-5p expressions after miR-338-5p (50 nM or 100 nM) or negative control (N.C.) (100 nM) was transiently transfected into HCT116 cells. FIG. 3(c) shows the miR-338-5p expressions after anti-miR-338-5p (50 nM or 100 nM) or anti-N.C. (100 nM) was transiently transfected into SW480 cells. Data are presented as median (IQR) (n=3) (p-values were analyzed using Mann-Whitney tests). FIG. 3(d) shows mRNA expressions of miR-338-5p target genes, including SPRY2, HEMGN, NDFIP1, ID1, ADM, PPP2R5A, DDX5, SCN9A, PIK3C3, and HOXA5 measured by qPCR after transfection of miR-338-5p into HCT116 cells or anti-miR-338-5p into SW480 cells.

FIG. 4(a) shows the Western blot used to confirm the quality of RIP. FIG. 4(b) shows expression of miR-338-5p in IgG control or Ago2 RIP fractions measured by qPCR assay in shGFP control cells. FIGS. 4(c) and 4(d) show mRNA expression levels of miR-338-5p and PIK3C3 in IgG or Ago2 RIP fractions measured by RT-qPCR assay. Data are presented as median (IQR) (n=5) (P-values were analyzed using Mann-Whitney tests).

FIG. 5(a) shows the Wild-type (WT-PIK3C3, SEQ ID NO.: 7) and mutant-type (Mut-PIK3C3, SEQ ID NO.: 8) target sequences of PIK3C3 constructed into 3'-UTR of p-miR-reporter luciferase plasmid downstream of luciferase gene. CMV refers to the cytomegalovirus promoter. FIG. 5(b) shows quantitative data presented as means±SEM (n=5) (P-values were analyzed using Mann-Whitney tests). FIG. 5(c) shows expression of PIK3C3 protein in CRC cell lines evaluated using Western blot. miR-338-5p or its N.C. was transiently transfected into HCT116 cells, and anti-miR-338-5p or anti-N.C. was transiently transfected into SW480 cells. Expression of PIK3C3 protein was assessed using Western blot. The β-actin was used as a loading control.

FIG. 6(a) shows the results of Kaplan-Meier analysis used to calculate the survival rate of mice injected with different cells (P-values were analyzed using Log Rank tests). FIG. 6(b) shows the spleen weight and spleen tumor volume of the mice. FIG. 6(c) shows photographs of tumor cells in ascites revealed by Liu's stain, with volume of ascites and number of tumor cells in ascites quantified in bar graphs. Data are presented as median (IQR) (n=5) (P-values were analyzed using Mann-Whitney tests). The scale bar in the photograph is 200 µm.

FIG. 7(a) shows metastatic tumors in the spleen, liver, and lung examined by hematoxylin and eosin (H&E) stain and PIK3C3 immunohistochemical staining (IHC) (100×). The metastatic tumors were indicated by arrow points. IHC showed that expression of PIK3C3 was high in both primary and metastatic tumors, when PIK3C3 was overexpressed. FIG. 7(b) shows the number and volume of metastatic tumors measured in the liver and lung, respectively. The scale bar represents 200 µm. Data are presented as median (IQR) (n=5) (P-values were analyzed using Mann-Whitney tests). FIG. 7(c) shows the expression of miR-338-5p and PIK3C3 mRNAs in primary tumors in the spleen by qPCR. (n=5). Correlation was calculated using linear regression (Data were analyzed by Spearman tests). FIG. 7(d) shows the expression level of PIK3C3 in splenic primary tumors and metastatic tumors in the liver and/or lung examined by IHC. FIG. 7(e) shows the ratio of miR-338-5p/PIK3C3 measured in splenic primary tumors and metastatic tumors in the liver. Data are expressed as median (IQR) (n=5) (P-values were analyzed using Mann-Whitney tests).

FIG. 8(a) shows the cell proliferation of HCT116 cells transiently transfected with miR-338-5p or negative control (N.C.) (100 nM) and cultured in the 96-well plates (4000/well) for 24 h. The number of cells was calculated every 24 h using MTT assay for four consecutive days. FIG. 8(b) shows the result of wound-healing after miR-338-5p or N.C. (100 nM) was transiently transfected into HCT116 cells. Twenty-four hours after creation of wounding, images of wound healing were recorded using an optical microscope (40×). Expression of miR-338-5p was confirmed using qPCR. The width between wounding was calculated at each time point and expressed as a percentage relative to that of time zero. FIG. 8(c) shows the result of wound-healing after anti-miR-338-5p or anti-negative control (anti-N.C.) (100 nM) was transiently transfected into SW480 cells. Twenty-four hours after wounding, images of wound healing were recorded using an optical microscope (40×). The scale bar represents 100 µm. The ratios of migration and miR-338-5p expression are shown as median (IQR) (n=5) (P-value was analyzed using Mann-Whitney tests). Data are expressed as means (n=6) (P-values were analyzed using ANOVA). FIGS. 8(d) and 8(e) show results of cell migration analyzed using Transwell migration assays 48 h after transfection with miR-338-5p or anti-miR-338-5p into HCT116 or SW480 cells. The transfected cells were seeded on Transwell plates, and migrated cells at the bottom of membrane were calculated. The scale bar represents 50 µm. The number of migrated HCT116 cells is shown as means±SEM (n=8) (P-values were analyzed using t tests). The number of migrated SW480 cells is shown as median (IQR) (n=5) (P-values were analyzed using Mann-Whitney tests). FIG. 8(f) shows results of cell invasion analyzed using Transwell invasion assays 96 h after transient transfection of anti-miR-338-5p (100 nM) into SW480 cells. The Transwell columns were coated with a Matrigel membrane. The transfected cells were seeded on the Transwell plates. Only invaded cells at the bottom of membrane after 96 h were counted. The scale bar represents 50 µm. Data are shown as median (IQR) (n=5) (P-value was analyzed using Mann-Whitney tests).

FIG. 9(a) shows the pCMV-Vps34 plasmid transiently transfected into SW480 cells and analyzed for PIK3C3 protein expression 48 h later. Cell migration was evaluated using Transwell assay. 48 hours after transfection, SW480 cells were seeded on Transwell plates, and cells appeared at the bottom of membrane were counted (n=8). FIG. 9(b) shows the result of cell invasion with pCMV-Vps34 plasmid transiently transfected into SW480 cells. Transwell columns were coated with a Matrigel membrane and seeded with transfected cells 48 h later. The invaded cells at the bottom of membrane were counted after 96 h (n=8). The scale bar represents 50 µm. Data are expressed as means±SEM, and P-value was analyzed using t-tests.

FIG. 10(a) shows the result of miR-338-5p or pCMV-Vps34 plasmid transiently transfected into SW480 cells and analyzed for PIK3C3 protein expression 48 h later, while evaluating cell migration using Transwell assay and photography. SW480 cells were seeded on Transwell plates, and cells appeared at the bottom of membrane were counted. Data are expressed as means±SEM (n=8) (P-value was analyzed using t tests). FIG. 10(b) shows the result of miR-338-5p and pCMV-Vps34 plasmids transiently transfected into SW480 cells and analyzed for cell invasion. Transwell columns were coated with a Matrigel membrane and seeded with transfected cells 48 h later. The invaded cells at the bottom of membrane were counted after 96 h. Data are expressed as means±SEM (n=8) (P-value was analyzed using t-tests). The scale bar represents 50 µm. FIG. 10(c) shows the result of wound healing assays to analyze HCT116 stable PIK3C3 overexpression cells infected with miR-338-5p or shGFP lentivirus and counted for migrated cells after 24 h. The scale bar represents 100 µm. Data are expressed as median (IQR) (n=4-5) (P-value was analyzed using Mann-Whitney tests).

FIG. 11(a) shows the SW480 cells transfected with sh-Vps34 lentivirus and assayed for PIK3C3 protein expression. Migration of SW480 cells was assayed using Transwell assay. Number of migrated CRC cells was counted after 48 h (n=8). FIG. 11(b) shows SW480 cells infected with sh-Vps34 lentivirus and counted for invaded cells after 96 h (n=8). The scale bar represents 50 μm. Data are expressed as means±SEM, and P-value was analyzed using t tests.

FIG. 12(a) shows the result of SW480 cells transiently transfected with anti-miR-338-5p (100 nM) and sh-Vps34 lentivirus, and then assayed for PIK3C3 protein expression and migration of SW480 cells. Number of migrated CRC cells was counted after 48 h with Transwell assay. Data are expressed as means±SEM (n=8) (P-value was analyzed using t-tests). FIG. (b) shows the result of Transwell invasion assays used to analyze SW480 cells transfected with anti-miR-338-5p or sh-Vps34 lentivirus and counted for invaded cells after 96 h. Data are expressed as means±SEM (n=8) (P-value was analyzed using t tests). The scale bar represents 50 μm.

FIG. 13(a) shows the result of RIP assay performed to precipitate the Ago2 complexes from stable miR-338-5p overexpression or shGFP control cells. Level of SPRY2 RNA expression in Ago2 RIP fractions was measured by RT-qPCR assay. Data are presented as median (IQR) (n=6) (P-values were analyzed using Mann-Whitney tests). FIG. 13(b) shows the result of SW480 and HCT116 cells transfected with miR-338-5p and analyzed for expression of SPRY2, P-ERK, ERK, P-AKT, AKT and β-actin by Western blot, respectively.

FIG. 14(a) shows the result of amiodarone-induced LC3 puncta formation. LC3 puncta were labelled with anti-LC3 antibody and fluorescent isothiocyanate-conjugated goat anti-rabbit IgG (green fluorescence). SW480 cell nuclei were stained with Hoechst 33258 (blue fluorescence). Images were photographed using florescent microscopy (the scale bar represents 10 μm). Data are presented as median (IQR) (n=5) (P value was analyzed using Mann-Whitney tests). FIG. 14(b) shows the Western blot of PIK3C3 and LC3 in SW480 cells treated with 10 μM of amiodarone for 48 h and then transfected with miR-338-5p or N.C. (100 nM). FIG. 14(c) shows the result of Transwell assay on SW480 cells treated with 10 μM of amiodarone and then transfected with or without 100 nM of miR-338-5p. Data are presented as median (IQR) (n=5) (P value was analyzed using Mann-Whitney tests). The scale bar represents 50 μm. FIG. 14(d) shows the Western blot of PIK3C3 and LC3 in HCT116 stable cells infected with lentivirus carrying miR-338-5p or shGFP, and then treated with amiodarone (10 μM) for 48 h. FIG. 14(e) shows the result of wound healing assays on HCT116 stable cells infected with lentivirus carrying miR-338-5p or shGFP, and then treated with 10 μM of amiodarone for 48 h. Number of migrated cells was counted after 24 h. The scale bar represents 100 μm. Data are expressed as median (IQR) (n=6) (P value was analyzed using MannWhitney tests). FIG. 14(f) shows the result of Transwell invasion assay on HCT116 cells infected with miR-338-5p or shGFP lentivirus, and invaded cells were counted after 48 h. The scale bar represents 50 μm. Data are expressed as means±SEM (n=8) (P value was analyzed using t tests).

FIG. 15(a) shows the Western blot to measure the expression of ATG5-ATG12 and LC3 in SW480 cells infected with shATG5 lentivirus. Representative results of Transwell assays are also shown. The scale bar represents 50 μm. Data are presented as means±SEM (n=8) (P values were analyzed using t tests). FIG. 15(b) shows the Western blot to measure the expression of ATG5-ATG12 and LC3 in SW480 cells infected with shATG5 lentivirus, followed by transfection with anti-miR-338-5p or anti-N.C. (100 nM). Representative results of Transwell assays are also shown. The scale bar represents 50 μm. The number of migrated cells is shown as means±SEM (n=8) (P values were analyzed using t tests). FIG. 15(c) shows the Western blot to analyze the expression of PIK3C3, LC3, p62, Snail, Twist, N-cadherin, E-cadherin, vimentin, fibronectin and β-actin, respectively, in HCT116 cells infected with lentivirus carrying miR-338-5p.

DETAILED DESCRIPTION

Figure 1A:
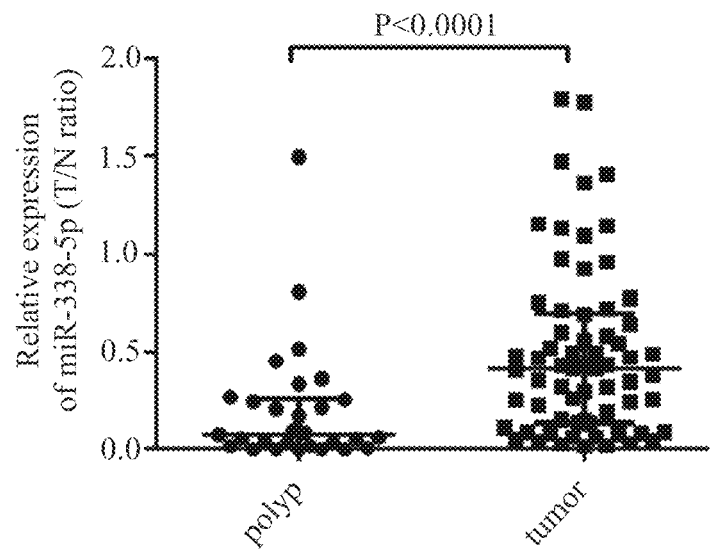
FIGS. 1(a) to 1(e) show the association of miR-338-5p with tumor staging and patient survival with expression of miR-338-5p or PIK3C3 mRNA assayed by real-time qPCR.

The present disclosure provides a method and biomarker to prognosticate the survival and recurrence of CRC in a subject by analyzing the expression levels of miRNAs and the target genes thereof, and more particularly analyzing the ratio between the expression levels of miRNA and its target genes to determine the prognosis of CRC patients.

MiR-338 belongs to the family of brain-specific miRNA precursors in an intronic region within the apoptosis-associated tyrosine kinase (AATK) gene. The miR-338 stem loop contains miR-338-3p and miR-338-5p. MiR-338-3p inhibits the migration and invasion of CRC in vitro, whereas increased serum miR-338-5p was observed in the advanced stages of CRC patients. MiR-338-5p was shown to promote invasion of human glioma in vitro; however, on the contrary, miR-338-5p suppressed proliferation, colony formation, migration and cisplatin resistance for esophageal squamous cell carcinoma (ESCC). Therefore, miR-338-5p's relevance to cancer is controversial, and clinical relevance and mechanisms underlying miR-338-5p in the pathogenesis of human CRC are still unclear.

The phosphatidylinositol 3-kinase (PIK3-kinase) catalytic subunit type 3 (PIK3C3) contains three classes of catalytic subunits: class I, class II, and class III (35). PIK3C3 is encoded by yeast vacuolar protein sorting 34 (Vps34) gene and is relevant in intracellular membrane trafficking. PIK3C3 also induces autophagy nucleation through complex formation with Beclin1, autophagy related 14 (Atg14), and UV radiation resistance associated (UVRAG) by phosphorylation of 3-OH of phosphatidylinositol to phosphatidyl-inositol-3-phosphate. In addition, PIK3C3 complex inhibits the epithelial-mesenchymal transition (EMT) by activating autophagy and degrading Snail and Twist of breast cancer cells, resulting in suppression of cell migration, tumor formation, and metastasis.

Sprouty (SPRY) was first discovered in 1998 as a common antagonist for fibroblast growth factor (FGF) and epidermal growth factor (EGF) signaling pathways in Drosophila. Three human homologs of the fly gene (hSPRY1, hSPRY2, hSPRY3) were identified by Hacohen et al., and the fourth member, hSPRY4, was found in mice and humans. SPRY could inhibit the activation of extracellular signal-regulated kinase (ERK) in response to a wide range of trophic factors, including FGF, platelet-derived growth factor (PDGF), vascular endothelial growth factor (VEGF), and nerve growth factor (NGF). SPRY2 acts as an antagonist of EGF and FGF pathways through inhibition of fibroblast growth factor receptor substrate 2 (FRS2), cbl proto-oncogene (CBL), growth factor receptor bound protein 2 (GRB2) and rapidly accelerated fibrosarcoma (RAF) kinase. In addition, SPRY2 enhances the EGF-induced mitogen-activated protein kinase (MAPK) activation.

Autophagy is an adaptive cellular process to stress through composition of autophagosomes, which contain microtubule-associated protein light chain 3 II (LC3 II). The autophagosomes engulf cytosolic organelles and proteins, fuse with lysosome, recycle macromolecules for the synthesis of essential components prepare as an energy supply. Autophagy is involved in a number of human diseases. With regard to carcinogenesis, autophagy has multifaceted roles that can suppress tumorigenesis, as well as promote tumor formation through different mechanisms.

Autophagy could inhibit the migration of cancer cells. For example, induction of autophagy represses migration and invasion of cervical cancer cells through inhibition of VEGF and MMP9. Autophagy also regulates cell migration through degradation of β1 integrin. Up-regulated Beclin1 inhibits the migration and metastasis of CRC in vitro through autophagy. Down-regulated autophagy-related genes (ATG5 and Beclin1) were observed in primary CRCs. Furthermore, absence of ATG5, Beclin1, and LC3B is associated with poor prognosis of CRC patients. The miR-338-3p inhibits the autophagy of human cervical cancer cells through PI3K/AKT/mTOR signaling pathway. However, the potential significance of miR-338-5p in autophagy remains ambiguous before the present disclosure.

For statistical analysis carried out in this application, the parametric test (Student's t-test or analysis of variance (ANOVA)) was chosen to analyze the data with normal distribution, and results were presented as means±standard error of the mean (SEM). For abnormally distributed data or small sample size, the non-parametric test (Mann-Whitney U test or Kruskal-Wallis H test) was used. The results are presented as median (interquartile range, IQR). Correlation of miR-338-5p with PIK3C3 mRNA expression was analyzed using Spearman tests. Survival analysis was calculated using Log Rank test. Univariate and multivariate associations with overall survival were evaluated using Cox proportional hazards regression models and estimated using the hazard ratio with 95% confidence interval (CI).

All terms including descriptive or technical terms which are used herein should be construed as having meanings that are obvious to one of ordinary skill in the art. However, the terms may have different meanings according to an intention of one of ordinary skill in the art, case precedents, or appearance of new technologies. Also, some terms may be arbitrarily selected by the applicant, and in this case, the meaning of the selected terms will be described in detail in the comprehensive descriptions of the present disclosure. Thus, the terms used herein have to be defined based on meaning of the terms together with descriptions throughout the specification.

Also, when a part "includes" or "comprises" a component or a step, unless there is a particular description contrary thereto, the part can further include other components or other steps, not excluding the others.

MicroRNAs (miRNA) are a class of short, endogenous and noncoding RNAs of 18 to 24 nucleotides (nt) long that target specific mRNA 3'-untranslated regions (3'-UTRs), and decay or inhibit the translation of their target mRNAs. MiRNA functions as an epigenetic factor in the regulation of cell proliferation, tumor invasion, and metastasis by modulating tumor suppresser genes or oncogenes. As used herein, the term "microRNA" (miRNA or miR) includes human miRNAs, mature single stranded miRNAs, precursor miRNAs (pre-miR), and variants thereof, which may be naturally occurring or artificially synthesized. In some instances, the term "miRNA" also includes primary miRNA (pri-miR) transcripts and duplex miRNAs. Unless otherwise noted, when used herein, the name of a specific miRNA refers to the mature miRNA. For example, miR-122a refers to a mature miRNA sequence derived from pre-miR-122. The sequences for particular miRNAs, including human mature and precursor sequences, are reported in the miRBase: Sequences Database; Griffiths-Jones et al., Nucleic Acids Research, 2008, 36, Database Issue, D154-D158; Griffiths-Jones et al., Nucleic Acids Research, 2006, 34, Database Issue, D140-D144; and Griffiths-Jones, Nucleic Acids Research, 2004, 32, Database Issue, D109-D111. For certain miRNAs, a single precursor contains more than one mature miRNA sequences. In other instances, multiple precursor miRNAs contain the same mature sequence. In some instances, mature miRNAs have been re-named based on new scientific consensus. The skilled artisan will appreciate that scientific consensus regarding the precise nucleic acid sequence for a given miRNA, in particular for mature forms of the miRNAs, may change with time. MiRNAs detected by assays of this disclosure include naturally occurring or artificially synthesized sequences for the miRNAs.

Primers based on nucleotide sequences of the target sequences can be designed for use in amplification of the target sequences. For use in amplification reactions, such as PCR, a pair of primers can be used. The primers may hybridize to specific sequences of the probe set under stringent conditions, e.g. under conditions of high stringency, as known in the art. The pairs of primers are usually chosen so as to generate an amplification product of at least about 50 nucleotides, e.g. at least about 100 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, or at least about 1000 nucleotides. Algorithms for the selection of primer sequences are generally known in the art, and are available in commercial software packages. These primers may be used in standard quantitative or qualitative PCR-based assays to assess transcript expression levels of RNAs. Alternatively, these primers may be used in combination with probes, such as molecular beacons in amplifications using real-time PCR.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with normal linkage or backbone of RNA and DNA being a 3' to 5' phosphodiester linkage. Specific examples of polynucleotide probes or primers useful in this disclosure include oligonucleotides containing modified backbones or non-natural inter-nucleoside linkages. As defined in this disclosure, oligonucleotides having modified backbones include both those that retain a phosphorus atom in the backbone and those that lack a phosphorus atom in the backbone. For the present disclosure, and as sometimes referenced in the art, modified oligonucleotides that do not have a phosphorus atom in their inter-nucleoside backbone can also be considered to be oligonucleotides.

A sequence identity of at least 80% includes at least 82%, at least 84%, at least 86%, at least 88%, at least 90%, at least 91%, at least 92%, at least 93%, at least 94%, at least 95%, at least 96%, at least 97%, at least 98%, at least 99%, and 100% sequence identity (to each and every nucleic acid sequence presented herein and/or to each and every SEQ ID NO presented herein).

Any of a variety of sequence alignment methods can be used to determine percent identity, including, without limitation, global methods, local methods and hybrid methods, e.g. segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g. CLUSTAL W (see, e.g. Julie D. Thompson et al., CLUSTAL W: Improving the Sensitivity of Progressive Multiple Sequence Alignment through Sequence Weighting, Position-Specific Gap Penalties and Weight Matrix Choice, 22 (22) Nucleic Acids Research 4673-4680 (1994)), and iterative refinement, (see, e.g. Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996)). Local methods align sequences by identifying one or more conserved motifs shared by all of the input sequences. Non-limiting methods include, e.g. Match-box (see, e.g. Eric Depiereux and Ernest Feytmans, Match-Box: A Fundamentally New Algorithm for the Simultaneous Alignment of Several Protein Sequences, 8(5) CABIOS 501-509 (1992)), Gibbs sampling (see, e.g. C. E. Lawrence et al., Detecting Subtle Sequence Signals: A Gibbs Sampling Strategy for Multiple Alignment, 262 (5131) Science 208-214 (1993)), and Align-M (see, e.g. Ivo Van Wale et al., Align-M: A New Algorithm for Multiple Alignment of Highly Divergent Sequences, 20 (9) Bioinformatics: 1428-1435 (2004)). Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992.

The term "amplification" refers to any process of producing at least one copy of a nucleic acid, e.g. an expressed RNA, and in many cases, producing multiple copies. An amplification product can be RNA or DNA, and may include a complementary strand to the expressed target sequence. DNA amplification products can be produced initially through reverse translation and then optionally from further amplification reactions. The amplification product may include all or a portion of a target sequence, and may optionally be labeled. A variety of amplification methods are suitable for use, including polymerase-based methods and ligation-based methods. Exemplary amplification techniques include polymerase chain reaction (PCR) method, lipase chain reaction (LCR), ribozyme-based methods, self-sustained sequence replication (3SR), nucleic acid sequence-based amplification (NASBA), the use of Q Beta replicase, reverse transcription, nick translation, and the like.

The first cycle of amplification in polymerase-based methods typically forms a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR may be designed to hybridize to regions in their corresponding template that can produce an amplifiable segment; thus, each primer may hybridize so that its 3'-nucleotide is paired to a nucleotide in its complementary template strand that is located at the 3' end from the 3'-nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase T7, Sequenase Version 2.0 T7, Tub, Taq, Tth, Pfic, Pfu, Tsp, Tfl, Tli and *Pyrococcus* sp. (strain GB-D) DNA polymerases; RNA polymerases such as *E. coli*, SP6, T3 and T7 RNA polymerases; and reverse transcriptases such as AMV, M-MuLV, MMLV, RNAse H MMLV (SuperScript), SuperScript II, ThermoScript, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfic, Pfu, Tsp, Tfl, Tli and *Pyrococcus* sp. (strain GB-D) DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e g manganese), optional cosolvents, temperature, thermal cycling profile for amplification schemes comprising a polymerase chain reaction, and may depend in part on the polymerase being used as well as the nature of the sample. Cosolvents include formamide (typically at from about 2% to about 10%), glycerol (typically at from about 5% to about 10%), and DMSO (typically at from about 0.9% to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used; for example, centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; for example, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

As used herein, prognosis of cancer may include predicting the clinical outcome of the patient, assessing the risk of cancer recurrence, determining treatment modality, or determining treatment efficacy.

As used herein, the term "metastasis" describes the spread of a cancer from one part of the body to another. A tumor formed by cells that have spread can be called a "metastatic tumor" or a "metastasis." The metastatic tumor often contains cells that are like those in the original (primary) tumor.

As used herein, the term "progression" describes the course of a disease, such as a cancer, as it becomes worse or spreads in the body.

The terms "subject," "patient" and "individual" are used interchangeably herein and refer to a warm-blooded animal, such as a mammal that is afflicted with, or suspected of having, at risk for or being pre-disposed to, or being screened for cancer, in particular actual or suspected cancer. These terms include, but are not limited to, domestic animals, sports animals, primates and humans. For example, the terms refer to a human.

It is further noted that, as used in this disclosure, the singular forms "a," "an," and "the" include plural referents unless expressly and unequivocally limited to one referent. The term "or" is used interchangeably with the term "and/or" unless the context clearly indicates otherwise.

EXAMPLE

Exemplary embodiments of the present disclosure are further described in the following examples, which do not limit the scope of the present disclosure.

The following examples describe the methods to analyze the expression levels of miRNA and its target genes as the prognostic biological markers for CRC patients.

Example 1: Clinical Implication of miR-338-5p and PIK3C3 Expression Levels

A total of 29 sample pairs consisting of colorectal polyps and normal adjacent specimens and 66 sample pairs consisting of colorectal cancer and adjacent normal specimens were collected.

Total RNA was extracted from the specimens using Trizol (1000 µL, MDBio Inc., Taipei, Taiwan), followed by addition of chloroform (200 µL), and then mixed by shaking and incubated at room temperature (RT) for 5 min. Then, the mixture was centrifuged at 12,000 rpm at 4° C. for 8 min. The supernatants (600 µLt) was transferred to a new Eppendorf tube, and incubated with isopropanol (600 µL) at −20° C. for 30 min. After centrifugation at 12,000 rpm for 8 min at 4° C., the pellets were rinsed with 75% alcohol (1 mL), centrifuged at 7,500 rpm twice at 4° C., and then air-dried at RT for 10 min. Finally, the RNA pellet was resuspended with diethyl pyrocarbonate (DEPC) treated water (50 to 200 µL), and measured for RNA concentration at $OD_{260}$.

Reverse transcription of miRNA was performed using miScript II RT kit (QGENE) or Ncode VILO miRNA cDNA Synthesis Kit (Invitrogen) and the products were incubated at 37° C. for 60 min Expression of miR-338-5p and U54 (reference control) was measured by quantitative polymerase chain reaction (qPCR) using miScript SYBR green (QGENE) or SYBR® Green Supermix (Application Biosystems, Birchwood, UK). The PCR cycling program consisted of 40 cycles, with each cycle having DNA denaturation for 30 sec. at 94° C., followed by primer annealing for 30 sec. at 60° C. and a final step of elongation for 30 sec. at 72° C.

Expression levels of PIK3C3 and β-actin (reference control) mRNA were measured by qPCR using SYBR Green Supermix (Application Biosystems, Birchwood, UK). The PCR cycling program consisted of 40 cycles, with each cycle having DNA denaturation for 30 sec. at 94° C., followed by primer annealing for 30 sec. at 55° C. and an elongation step for 30 sec. at 72° C.

The primers used in the PCR is shown in Table 1 below.

TABLE 1

Primer sequences used in PCR for determining expression levels of MiR-338-5p and PIK3C3

| Primer | | SEQ ID NO. |
|---|---|---|
| miR-338-5p | 5'-AAC-AAT-ATC-CTG-GTG-CTG-AGT-GGA-3' | 1 |
| U54 | 5'-GGT-ACC-TAT-TGT-GTT-GAG-TAA-CGG-TGA-3' | 2 |
| PIK3C3F | 5'-TCG-ATG-TGT-CAA-GTG-TGA-TGA-3' | 3 |
| PIK3C3R | 5'-TTC-AGA-TCG-TGG-TCA-GAA-GGT-3' | 4 |
| β-actinF | 5'-GGC-GGC-ACC-ACC-ATG-TAC-CCT-3' | 5 |
| β-actinR | 5'-AGG-GGC-CGG-ACT-CGT-CAT-ACT-3' | 6 |

The expression level data were normalized with endogenous U54 or β-actin reference control using comparative $C_T$ methods, with relative level of miR-338-5p expression represented by log 10 ($2^{-\Delta CT}$) ($-\Delta C_T = C_T$ miR-338-5p$-C_T$ U54) and relative level of PIK3C3 expression represented by log 10 ($2^{-\Delta CT}$) ($-\Delta C_T = C_T$ PIK3C3$-C_T$ β-actin). Expression levels of miR-338-5p or PIK3C3 were estimated as ratios of its expression in the tumor relative to that of adjacent non-tumor tissue. Then, miR-338-5p/PIK3C3 ratio was calculated.

For abnormally distributed data or small sample size, non-parametric test (Mann-Whitney U test or Kruskal-Wallis H test) was used. The results were presented as median (interquartile range, IQR). The correlation of miR-338-5p with PIK3C3 mRNA expression was analyzed using Spearman tests. Survival analysis was calculated using Log Rank test. Univariate and multivariate associations with overall survival were evaluated using Cox proportional hazards regression models and estimated using the hazard ratio with 95% confidence interval (CI).

The association of miR-338-5p expression levels with clinicopathologic indicators and patient outcomes was analyzed. A significantly lower ratio of miR-338-5p expression (tumor/adjacent normal, T/N) was demonstrated in benign polyps than in CRCs measured by real-time PCR, as shown in FIG. 1(a) and Table 2 below.

TABLE 2

Correlation of clinicopathologic characteristics with miR-338-5p expression (T/N ratio) in colorectal polyps and CRC tumor tissues (n = 95)

| Variables | Cases (n) | Median (IQR)[1] | P[2] |
|---|---|---|---|
| Sex | | | 0.3618 |
| Male | 58 | 0.2474 (0.0602-0.4729) | |
| Female | 37 | 0.3461 (0.0716-0.6181) | |

TABLE 2-continued

Correlation of clinicopathologic characteristics with miR-338-5p expression (T/N ratio) in colorectal polyps and CRC tumor tissues (n = 95)

| Variables | Cases (n) | Median (IQR)[1] | P[2] |
|---|---|---|---|
| Polyp/Tumor | | | <0.0001* |
| Polyp | 29 | 0.0770 (0.0178-0.2594) | |
| Tumor | 66 | 0.4103 (0.1350-0.6961) | |

N: adjacent non-tumor tissue.
T: tumor tissue.
[1]IQR: interquartile range.
[2]Mann-Whitney test.
P-value < 0.05 was considered statistically significant and marked with *.

Figure 1B:
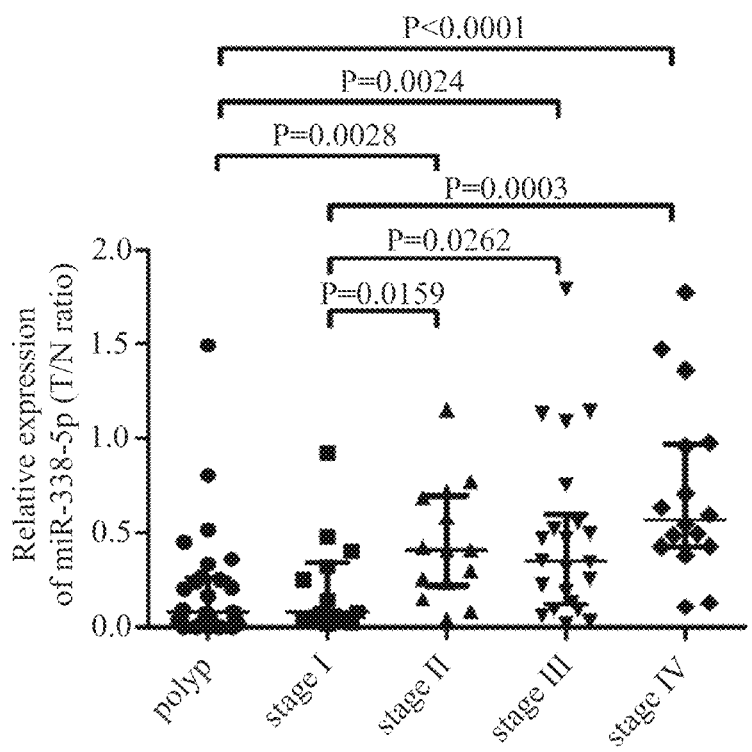
Figure 1C:
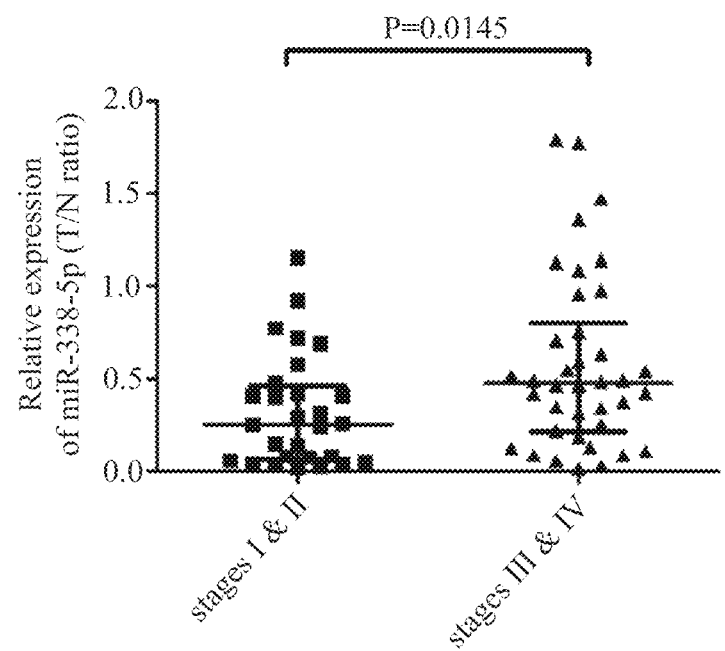
Figure 1D:
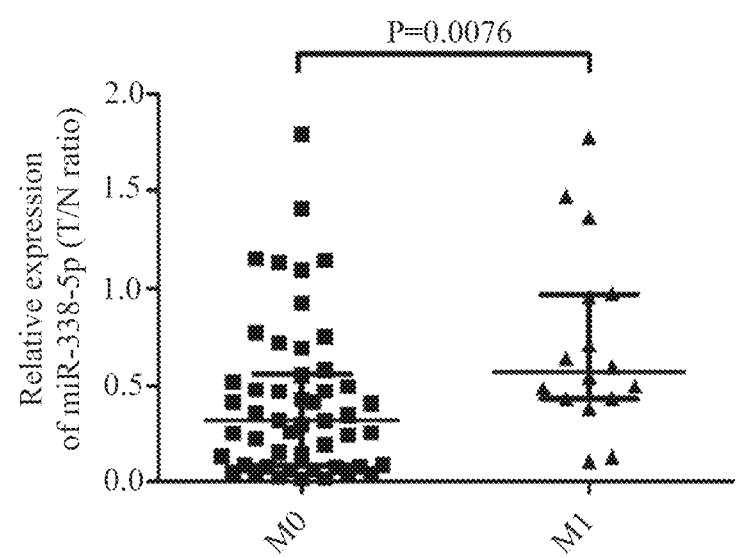
Figure 1E:
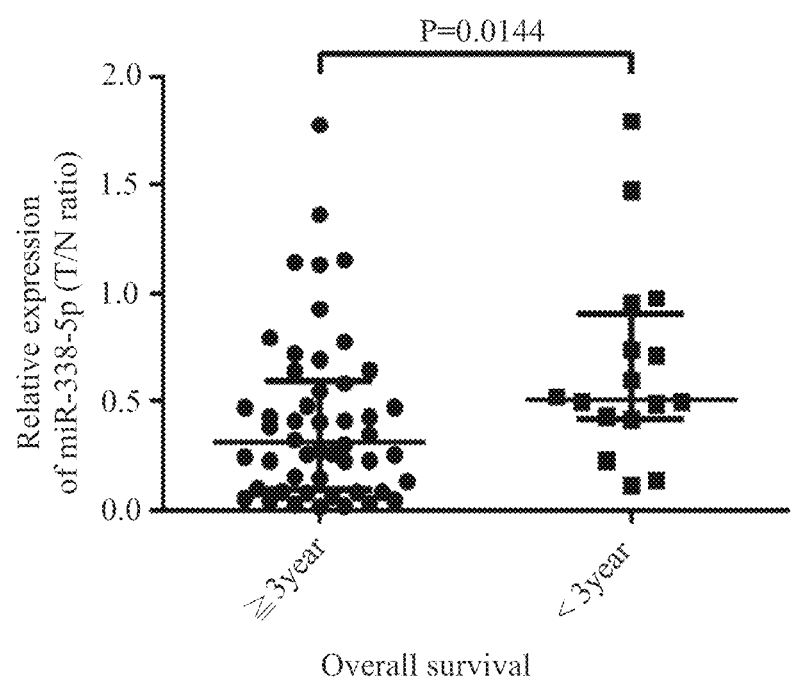

In addition, as shown in FIG. 1(b), expression of miR-338-5p was lower in early stages of colorectal neoplasia (polyps or stage I CRC) than those of advanced stages of CRC (stages II-IV). As shown in Table 3 below, further analysis showed that overexpression of miR-338-5p was positively related to individual tumor stages (P=0.0019, Kruskal-Wallis test), advanced tumors (stages I-II vs. stages P=0.0145, Mann-Whitney test) (FIG. 1(c)), distant metastasis (P=0.0076, Mann-Whitney test) (FIG. 1(d)), and poor overall survival (P=0.0144, Mann-Whitney test) (FIG. 1(e)).

TABLE 3

Correlation of clinicopathologic characteristics of CRC patients with miR-338-5p expression (T/N ratio) (n = 66)

| Variables | Case | Median (IQR)[1] | P[2] |
|---|---|---|---|
| Tumor stage | | | 0.0019* |
| I | 14 | 0.0800 (0.0424-0.3421) | |
| II | 14 | 0.4103 (0.2201-0.6984) | |
| III | 22 | 0.3498 (0.1250-0.6033) | |
| IV | 16 | 0.5702 (0.4275-0.9711) | |
| Stages I + II vs. III + IV | | | 0.0145* |
| I + II | 28 | 0.2550 (0.0647-0.4650) | |
| III + IV | 38 | 0.4785 (0.2153-0.8051) | |
| N-stage | | | 0.1920 |
| N0 | 32 | 0.3095 (0.0789-0.6640) | |
| N1 | 23 | 0.4684 (0.2235-0.6394) | |
| N2 | 11 | 0.4288 (0.3803-0.7930) | |
| Post-Op. Recur. + Metast.[3] | | | 0.2648 |
| Yes | 45 | 0.3461 (0.1881-0.6104) | |
| No | 21 | 0.4858 (0.1214-0.9668) | |
| Metastasis | | | 0.0076* |
| No (M0) | 50 | 0.3195 (0.0875-0.5601) | |
| Yes (M1) | 16 | 0.5702 (0.4275-0.9711) | |
| Overall Survival | | | 0.0144* |
| ≥3 years | 50 | 0.3095 (0.0931-0.5960) | |
| <3 years | 16 | 0.5067 (0.4190-0.9026) | |
| Disease-free Survival | | | 0.8178 |
| ≥3 years | 40 | 0.2776 (0.08377-0.5343) | |
| <3 years | 10 | 0.3355 (0.07279-0.6624) | |

N: adjacent non-tumor tissue.
T: tumor tissue.
[1]IQR: interquartile range.
[2]Mann-Whitney test or Kruskal-Wallis test.
[3]Postoperative tumor recurrence + metastasis within 5 years.
*P < 0.05.

Figure 2A:
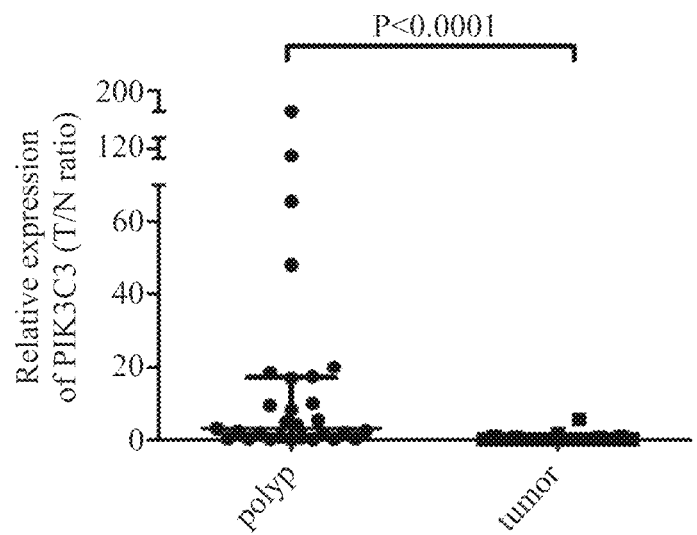
FIGS. 2(a) to 2(f) show the association of PIK3C3 expression and expression ratio of PIK3C3/miR-338-5p with tumor staging and patient survival.
Figure 2B:
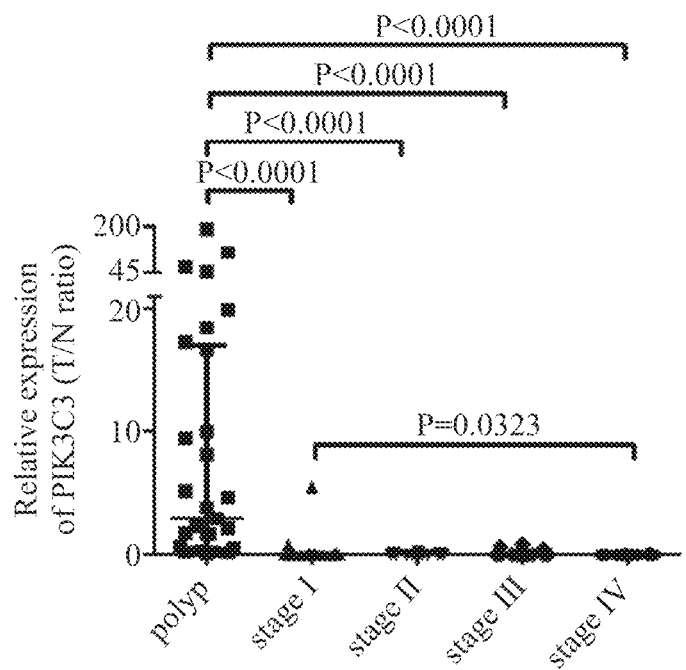

As for PIK3C3, the relative mRNA expressions of PIK3C3 (T/N) were significantly higher in benign polyps than in CRC tumor tissues of stages I to IV, as shown in FIG. 2(a), FIG. 2(b) and Table 4 below.

TABLE 4

Correlation of clinicopathologic characteristics with PIK3C3 expression (T/N ratio) in colorectal polyps and CRC tumor tissues (n = 95)

| Variables | Cases (n) | Median (IQR)[1] | P[2] |
|---|---|---|---|
| Sex | | | 0.0969 |
| Male | 58 | 0.0791 (0.0042-1.7350) | |
| Female | 37 | 0.0189 (0.0015-0.2540) | |
| Pathologic diagnosis | | | <0.0001* |
| Polyp | 29 | 2.9490 (0.4986-16.9700) | |
| Tumor | 66 | 0.0075 (0.0017-0.0685) | |

N: adjacent non-tumor tissue.
T: tumor tissue.
[1]IQR: interquartile range.
[2]Mann-Whitney test.
*P < 0.05.

The phosphatidylinositol 3-kinase (PIK3-kinase) has three classes of catalytic subunits: class I, class II, and class III. PIK3C3 is encoded by yeast vacuolar protein sorting 34 (Vps34) gene and involves in intracellular membrane trafficking. PIK3C3 also induces autophagy nucleation through complex formation with Beclin1, autophagy related 14 (Atg14), and UV radiation resistance associated (UVRAG) by phosphorylation of 3-OH of phosphatidylinositol to phosphatidyl-inositol-3-phosphate. In addition, PIK3C3 complex inhibits the EMT by activating autophagy and degrading Snail and Twist of breast cancer cells, resulting in suppression of cell migration, tumor formation, and metastasis.

It was found that PIK3C3 mRNA expression itself had no significant association with clinicopathologic indicators and patient outcome, as shown in Table 5 below.

TABLE 5

Correlation of clinicopathologic characteristics of CRC patients with PIK3C3 expression (T/N ratio) (n = 66)

| Variables | Cases (n) | Median (IQR)[1] | P[2] |
|---|---|---|---|
| Stage | | | 0.2734 |
| I | 14 | 0.0357 (0.0037-0.1400) | |
| II | 14 | 0.0075 (0.0001-0.0548) | |
| III | 22 | 0.0053 (0.0010-0.0703) | |
| IV | 16 | 0.0033 (0.0017-0.0212) | |
| Stage I + II vs. III + IV | | | 0.2153 |
| I + II | 28 | 0.0075 (0.0037-0.1134) | |
| III + IV | 38 | 0.0033 (0.0013-0.0448) | |
| N-stage | | | 0.4913 |
| N0 | 32 | 0.0072 (0.0030-0.0935) | |
| N1 | 23 | 0.0027 (0.0011-0.0595) | |
| N2 | 11 | 0.0220 (0.0021-0.0878) | |
| Post-Op. Recur. + Metast.[3] | | | 0.4246 |
| No | 45 | 0.0078 (0.0017-0.1077) | |
| Yes | 21 | 0.0043 (0.0018-0.0310) | |
| Metastasis | | | 0.2780 |
| No | 50 | 0.0079 (0.0017-0.0883) | |
| Yes | 16 | 0.0033 (0.0017-0.0212) | |
| Overall Survival | | | 0.7819 |
| ≥3 years | 50 | 0.0069 (0.0021-0.0793) | |
| <3 years | 16 | 0.0269 (0.0015-0.0765) | |
| Disease-free Survival | | | 0.6890 |
| ≥3 years | 40 | 0.0072 (0.0017-0.0704) | |
| <3 years | 10 | 0.0346 (0.0011-0.0883) | |

N: adjacent non-tumor tissue.
T: tumor tissue.
[1]IQR: interquartile range.
[2]Mann-Whitney test or Kruskal-Wallis test.
[3]Postoperative tumor recurrence + metastasis within 5 years.
*P < 0.05.

Figure 2C:
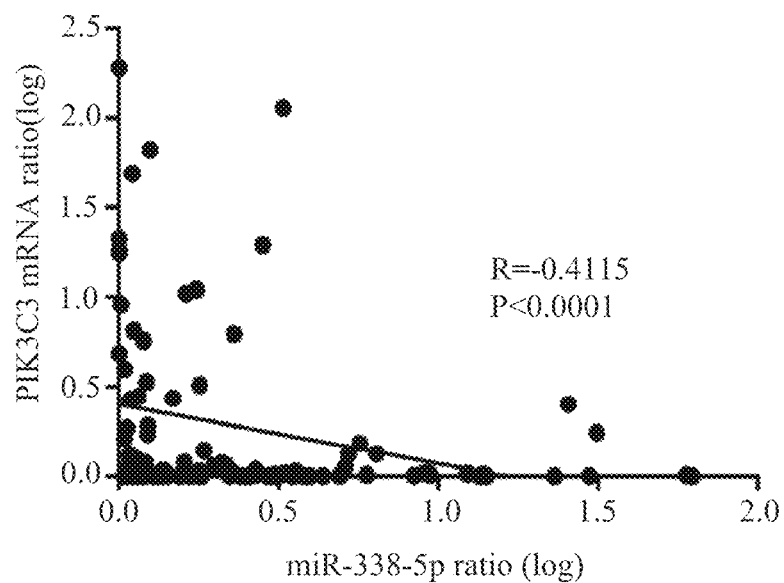
Figure 2D:
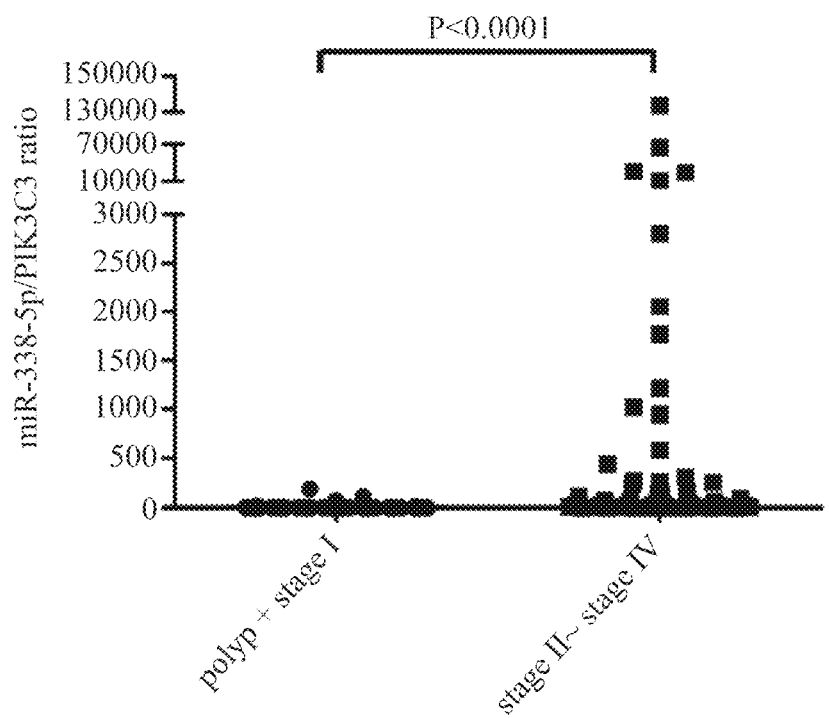
Figure 2E:
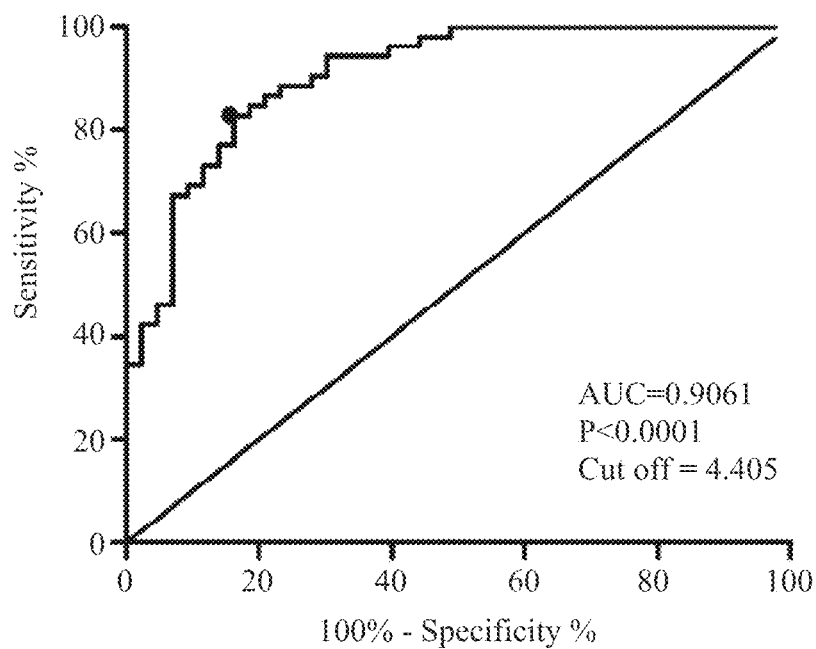
Figure 2F:
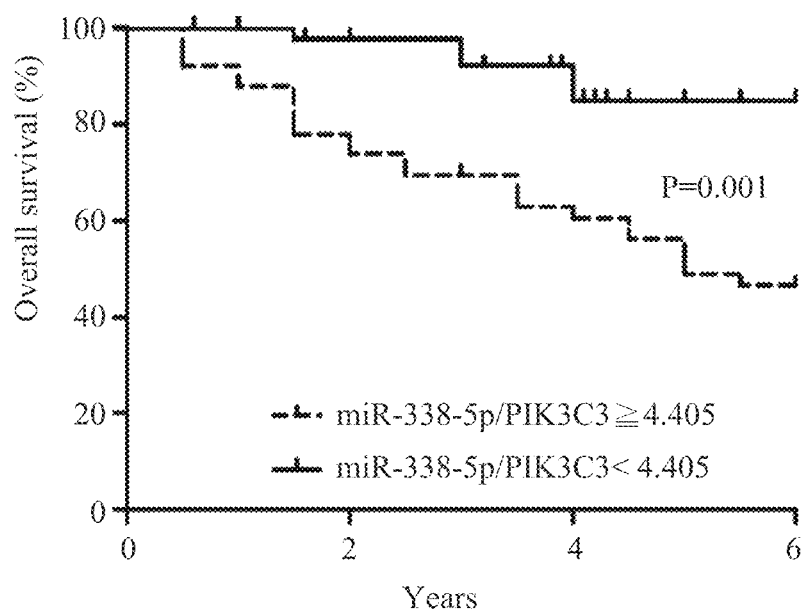

Further analysis found that expression of PIK3C3 was negatively related to miR-338-5p, as shown in FIG. 2(c). Linear regression analysis showed that PIK3C3 expression is inversely correlated with miR-338-5p in vivo (P<0.0001, r=−0.4115, Spearman test). Late-stage tumors at stages II to IV had significantly higher miR-338-5p/PIK3C3 ratios (P<0.0001, Mann-Whitney test) than those of early-stage colorectal neoplasia, as shown in FIG. 2(d). The miR-338-5p/PIK3C3 ratio is found to effectively distinguish tumor grading with area AUC values estimated at 0.9061 and cut-off set at 4.405, as shown in FIG. 2(e). An AUC between 0.5 and 0.6 was defined as non-discriminatory, between 0.6 and 0.7 as acceptable, between 0.7 and 0.8 as excellent, and between 0.8 and 0.9 as outstanding. A ratio of miR-338-5p/PIK3C3 larger than or equal to 4.405 also significantly predicted poor overall survival of patients (P=0.001, Log Rank test), as shown in FIG. 2(f). Kaplan-Meier analysis was used to estimate the overall survival of polyps and CRC patients (n=95) at 6 years after surgery, and the miR-338-5p/PIK3C3 ratio at 4.405 could be used as a prognostic biomarker for CRC patients. These findings provide support for the involvement of miR-338-5p and PIK3C3 in the progression of CRC tumorigenesis.

Univariate analysis results in Table 6 below showed that polyps or CRCs with miR-338-5p/PIK3C3 ratio>4.405 had 5.418 times higher risk of mortality than those with ratio<4.405 (P=0.002, Cox proportional hazards regression model), and patients of stages II to IV CRC had 20.908 times higher risk of mortality than that of polyps or stage I CRC (P=0.003, Cox proportional hazards regression model).

TABLE 6

Univariate association with death of polyps and CRC patients

| Variables | Number (%) | Hazard ratio for death (95% CI)[1] | P-value |
|---|---|---|---|
| MiR-338-5p/PIK3C3 | | | 0.002* |
| <4.405 | 45 (47) | 1.0 (reference) | |
| ≥4.405 | 50 (53) | 5.42 (1.88-15.59) | |
| Lesion | | | 0.003* |
| Polyp + stage I CRC | 43 (45) | 1.0 (reference) | |
| Stage II to IV CRC | 52 (55) | 20.91 (2.84-153.91) | |

TABLE 6-continued

Univariate association with death of polyps and CRC patients

| Variables | Number (%) | Hazard ratio for death (95% CI)[1] | P-value |
|---|---|---|---|

[1]The 95% confidence interval (CI) for the hazard ratio was estimated using Cox proportional hazards regression model.
*P < 0.05.

Multivariate analysis results as shown in Table 7 below revealed that CRC patients at stages II to IV had 13.921 times higher risk of mortality than those with polyps or stage I CRC (P=0.014, Cox proportional hazards regression model).

TABLE 7

Multivariate association with death of polyps and CRC patients

| Variables | Number (%) | Hazard ratio for death (95% CI)[1] | P-value |
|---|---|---|---|
| miR-338-5p/PIK3C3 | | | 0.111 |
| <4.405 | 45 (47) | 1.0 (reference) | |
| ≥4.405 | 50 (53) | 2.44 (0.82-7.32) | |
| Lesion | | | 0.014* |
| Polyp + stage ICRC | 43 (45) | 1.0 (reference) | |
| Stage II to IV CRC | 52 (55) | 7.89 (2.64-23.65) | |

[1]The 95% confidence interval (CI) for the hazard ratio was estimated using Cox proportional hazards regression model.
*P < 0.05.

Therefore, miR-338-5p is inversely correlated with PIK3C3 expression and involves in the progression of CRC. The miR-338-5p/PIK3C3 ratio is a prognostic biomarker in identifying the CRC patients who may require aggressive treatment strategy.

Example 2: Identification of Potential Target Genes of miR-338-5p in CRC

To identify potential target genes of miR-338-5p in tumorigenesis of CRC, analysis was carried out by TargetScan, EBI, and DIANA-microT software, combined with bioinformatic analysis using NCBI PubMed queries. As shown in Table 8 below, among top 42 consensus target genes, SPRY2, HEMGN, ID1, ADM, DDX5, SCN9A, PIK3C3, and HOXA5 were found to be highly related to CRC.

TABLE 8

Potential target genes of miR-338-5p in tumorigenesis of CRC predicted by EBI, Target Scan and DIANA combined with bioinformatic analysis using NCBI PubMed queries

| | Gene | NCBI Search (2016 Jun. 8) | | | | | | | |
|---|---|---|---|---|---|---|---|---|---|
| No. | Name | Cancer | Carcinoma | Colon | Migration | Invasion | Metastasis | Autophagy | miR-338-5p |
| 1 | RAB1A | 20 | 5 | 0 | 3 | 3 | 4 | 4 | 0 |
| 2 | SPRY2 | 114 | 36 | 13 | 41 | 24 | 15 | 0 | 0 |
| 3 | HEMGN | 13 | 24 | 6 | 10 | 1 | 7 | 2 | 0 |
| 4 | RAB28 | 3 | 0 | 0 | 1 | 0 | 1 | 0 | 0 |
| 5 | PCDH20 | 5 | 2 | 0 | 2 | 1 | 0 | 0 | 0 |
| 6 | CUL2 | 51 | 21 | 2 | 1 | 0 | 0 | 0 | 0 |
| 7 | CCDC126 | 0 | 0 | 0 | 0 | 0 | 0 | 0 | 0 |
| 8 | KLF2 | 79 | 15 | 2 | 33 | 6 | 6 | 3 | 0 |
| 9 | NDFIP1 | 11 | 0 | 0 | 1 | 0 | 0 | 0 | 1 |
| 10 | RB1CC1 | 50 | 4 | 2 | 5 | 1 | 3 | 51 | 0 |
| 11 | PIGP | 1 | 0 | 0 | 0 | 0 | 0 | 0 | 0 |
| 12 | ID1 | 551 | 146 | 17 | 93 | 72 | 96 | 3 | 0 |
| 13 | ADM | 2669 | 938 | 111 | 95 | 116 | 299 | 15 | 0 |
| 14 | NCK2 | 16 | 1 | 1 | 14 | 3 | 4 | 0 | 0 |
| 15 | RPIA | 5 | 2 | 1 | 0 | 1 | 0 | 0 | 0 |
| 16 | NTF3 | 4 | 1 | 1 | 5 | 0 | 4 | 0 | 0 |
| 17 | RAB23 | 23 | 14 | 0 | 7 | 10 | 2 | 2 | 0 |
| 18 | CLIC4 | 36 | 3 | 0 | 8 | 3 | 1 | 2 | 0 |

TABLE 8-continued

Potential target genes of miR-338-5p in tumorigenesis of CRC predicted by EBI, Target Scan and DIANA combined with bioinformatic analysis using NCBI PubMed queries

| Gene | | NCBI Search (2016 Jun. 8) | | | | | | | |
|---|---|---|---|---|---|---|---|---|---|
| No. | Name | Cancer | Carcinoma | Colon | Migration | Invasion | Metastasis | Autophagy | miR-338-5p |
| 19 | HESX1 | 5 | 0 | 0 | 4 | 0 | 0 | 0 | 0 |
| 20 | PPP2R5A | 11 | 2 | 0 | 0 | 0 | 0 | 0 | 1 |
| 21 | TOB1 | 55 | 17 | 2 | 4 | 10 | 8 | 0 | 0 |
| 22 | HORMAD | 15 | 3 | 0 | 0 | 1 | 0 | 0 | 0 |
| 23 | RBX1 | 126 | 25 | 2 | 2 | 4 | 4 | 6 | 0 |
| 24 | ANP32E | 14 | 0 | 1 | 0 | 0 | 1 | 0 | 0 |
| 25 | STK17B | 13 | 4 | 1 | 1 | 1 | 0 | 0 | 0 |
| 26 | ARNTL2 | 13 | 1 | 3 | 0 | 2 | 2 | 1 | 0 |
| 27 | INTU | 0 | 0 | 0 | 0 | 0 | 0 | 0 | 0 |
| 28 | NR1D1 | 39 | 9 | 3 | 4 | 1 | 2 | 5 | 0 |
| 29 | CBX3 | 29 | 11 | 3 | 4 | 3 | 3 | 0 | 0 |
| 30 | HS3ST5 | 1 | 0 | 0 | 0 | 1 | 1 | 0 | 0 |
| 31 | DUSP2 | 27 | 4 | 3 | 2 | 4 | 5 | 1 | 0 |
| 32 | TTC33 | 0 | 0 | 0 | 0 | 0 | 0 | 0 | 0 |
| 33 | FPGT | 0 | 0 | 0 | 0 | 0 | 0 | 0 | 0 |
| 34 | DDX5 | 83 | 16 | 4 | 6 | 4 | 4 | 0 | 0 |
| 35 | SCN9A | 24 | 4 | 4 | 6 | 6 | 7 | 0 | 0 |
| 36 | PIK3C3 | 89 | 9 | 4 | 2 | 8 | 5 | 247 | 0 |
| 37 | MAGEA10 | 11 | 2 | 0 | 0 | 0 | 1 | 0 | 0 |
| 38 | CADM2 | 11 | 5 | 0 | 1 | 4 | 1 | 0 | 0 |
| 39 | RNF170 | 0 | 0 | 0 | 0 | 0 | 0 | 0 | 0 |
| 40 | ATP6V0A4 | 3 | 1 | 0 | 0 | 1 | 0 | 0 | 0 |
| 41 | HOXA5 | 100 | 34 | 7 | 11 | 7 | 12 | 0 | 0 |
| 42 | IL22RA2 | 9 | 1 | 2 | 1 | 0 | 1 | 0 | 0 |

To verify the potential target genes, miR-338-5p expression levels were first measured in human colon cancer cell lines by qPCR, and mRNA levels of candidate genes were measured by qPCR after transfection of the cell line with miR-338-5p or anti-miR-338-5p (inhibitor of miR-338-5p).

Human colon cancer cell lines-SW480, SW620, and HCT116 were purchased from the American Type Culture Collection (ATCC, Rockville, Md., USA). Both SW480 and SW620 were cultured in L15 medium (Thermo Fisher Scientific, Carlsbad, Calif.) supplemented with 10% fetal bovine serum (FBS) (Hyclone, Logan, Utah) and antibiotic/antimycotic solution (Caisson Laboratories, Smithfield, Utah) at 37° C. in a humidified atmosphere. The HCT116 was cultured in Dulbecco's Modified Eagle's Medium (DMEM) (Thermo Fisher Scientific, Carlsbad, Calif.) supplemented with 10% FBS and antibiotic/antimycotic solution (Caisson Laboratories) at 37° C. in a humidified atmosphere of 5% $CO_2$.

Total RNA was extracted from the cell lines the same way as it was extracted from tissue specimen described above. Expression of miR-338-5p was measured by qPCR using SYBR Green Supermix (Application Biosystems, Birchwood, UK). Expression of PIK3C3, SPRY2, ADM, DDX5, HEMGN, HOXA5, ID1, NDFIP1, PPP2R5A, SCN9A and β-actin mRNA was measured using YEAtaq DNA polymerase (Yeastern Biotech Co, Taipei, Taiwan).

Figure 3A:
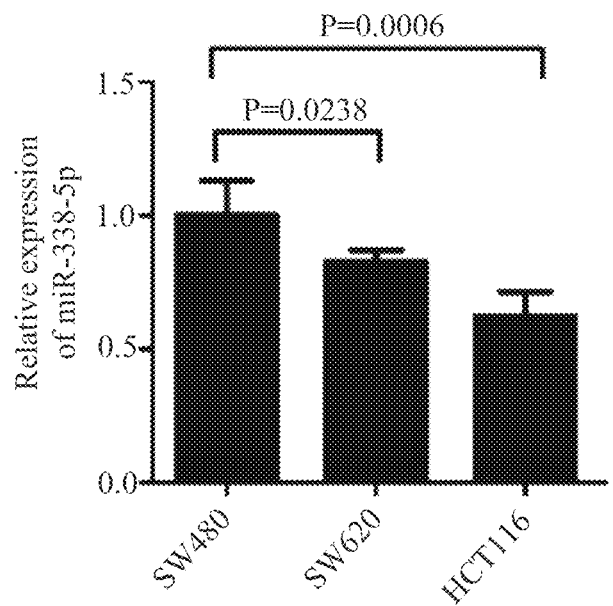
FIGS. 3(a) to 3(d) show the verification of target genes of miR-338-5p in CRC.
Figure 3B:
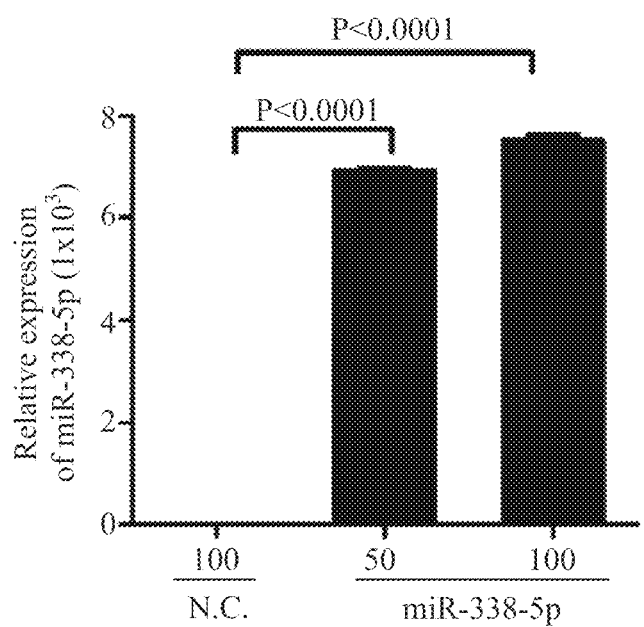
Figure 3C:
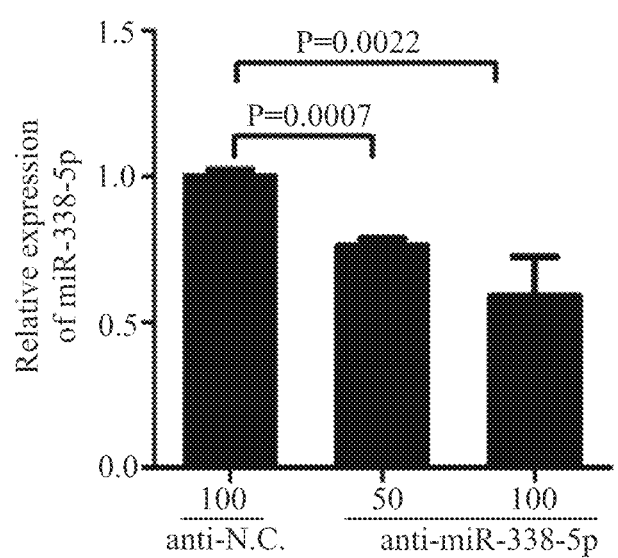

As shown in FIG. 3(a), it was found that expression of miR-338-5p is significantly higher in SW480 cells than in SW620 (P=0.0238, Mann-Whitney test) and in HCT116 (P=0.0006, Mann-Whitney test) cells, respectively. Therefore, SW480 and HCT116 cells were used for miR-338-5p knockdown and transfection experiments in vitro, respectively. RNA levels of potential target genes were measured by qPCR after HCT116 cells had been transiently transfected with miR-338-5p (mirVana miRNA mimic, Ambion, Invitrogen) (FIG. 3(b)) and SW480 cells with anti-miR-338-5p (mirVana miRNA inhibitor, Ambion, Invitrogen) (FIG. 3(c)) with Lipofectamine 2000 (Invitrogen).

Figure 3D:
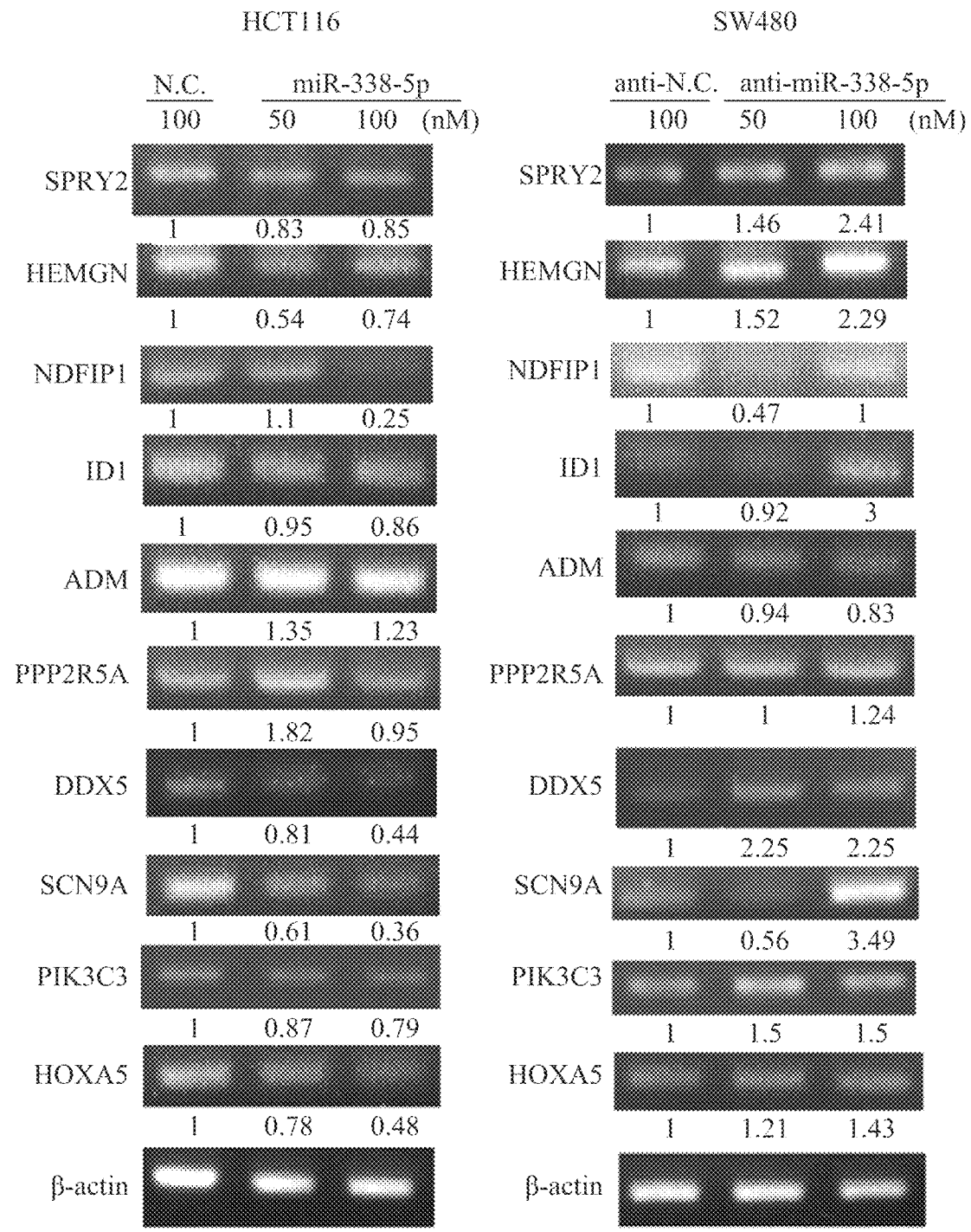

Expression of SPRY2, HEMGN, NDFIP1, ID1, DDX5, SCN9A, PIK3C3, and HOXA5 was found to be inhibited in HCT116 cells that were overexpressed with miR-338-5p. Except for NDFIP1, expressions of SPRY2, HEMGN, ID1, DDX5, SCN9A, PIK3C3, and HOXA5 were up-regulated after miR-338-5p had been inhibited (FIG. 3(d)). Accordingly, SPRY2, HEMGN, ID1, DDX5, SCN9A, PIK3C3 and HOXA5 are the target genes of miR-338-5p.

Example 3: PIK3C3 is a Target Gene of miR-338-5p in CRC

To clarify involvements of PIK3C3 and miR-338-5p in CRC, HCT116 cells with stable overexpression of miR-338-5p and shGFP control cell lines were established for RIP assay.

The miR-338-5p overexpressed lentivirus system was purchased from GE Healthcare Dharmacon (Lafayette, Colo.). Lentiviruses that express miR-338-5p or short hairpin RNAs (shRNAs) were produced according to provider's protocol. The stable overexpression cells were selected using puromycin (P8833; Sigma-Aldrich) at 15 ng/µL for SW480 cells and at 1 ng/µL for HCT116 cells. The shRNA targeting GFP were purchased from the National RNAi Core Facility (Academia Sinica, Taipei, Taiwan).

RIP assay of miR-338-5p and PIK3C3 was performed in HCT116 cells with stable overexpression of miR-338-5p by RIP-assay Kit for microRNA (RN1005, MBL). About 4 to 20 million cells were co-immunoprecipitated with 25 µg of RIP-certified anti-EIF2C2/AGO2 mouse monoclonal antibody (RN003M, MBL) overnight at 4° C., which was previously conjugated with Sepharose Protein G beads (17-0618-01, GE Healthcare Biosciences, Uppsala, Sweden). Rabbit IgG was used as negative control (RN1005, MBL).

Figure 4A:
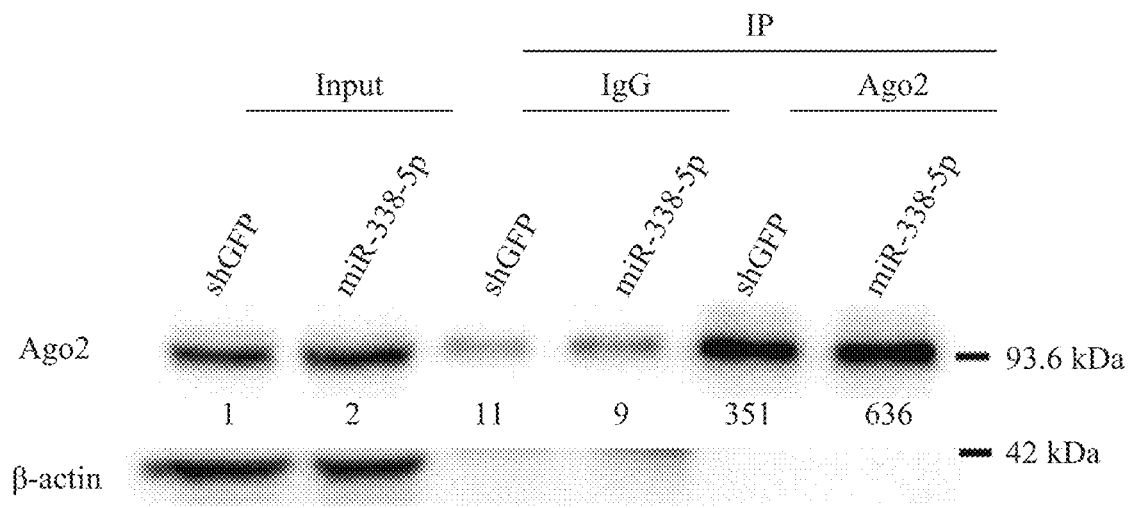
FIGS. 4(a) to 4(d) show that miR-338-5p is bound to PIK3C3 in CRC using ribonucleoprotein-immunoprecipitation (RIP) to precipitate the Ago2 complex from HCT116 cells with stable miR-338-5p overexpression or shGFP control cells.
Figure 4B:
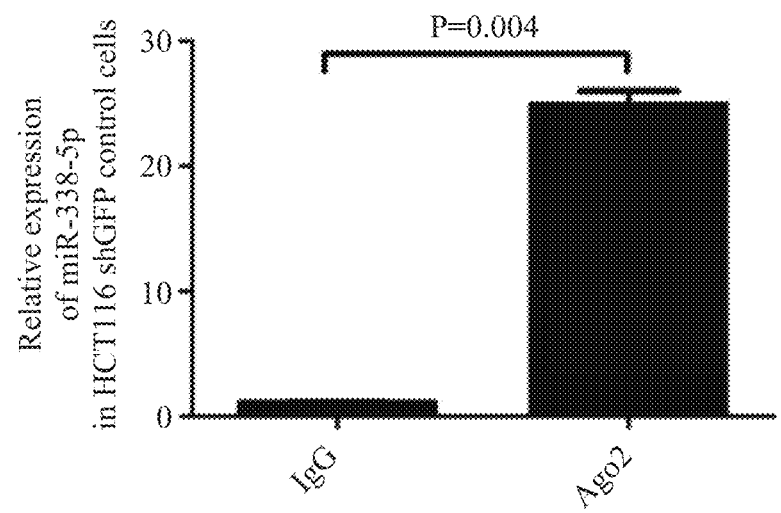
Figure 4C:
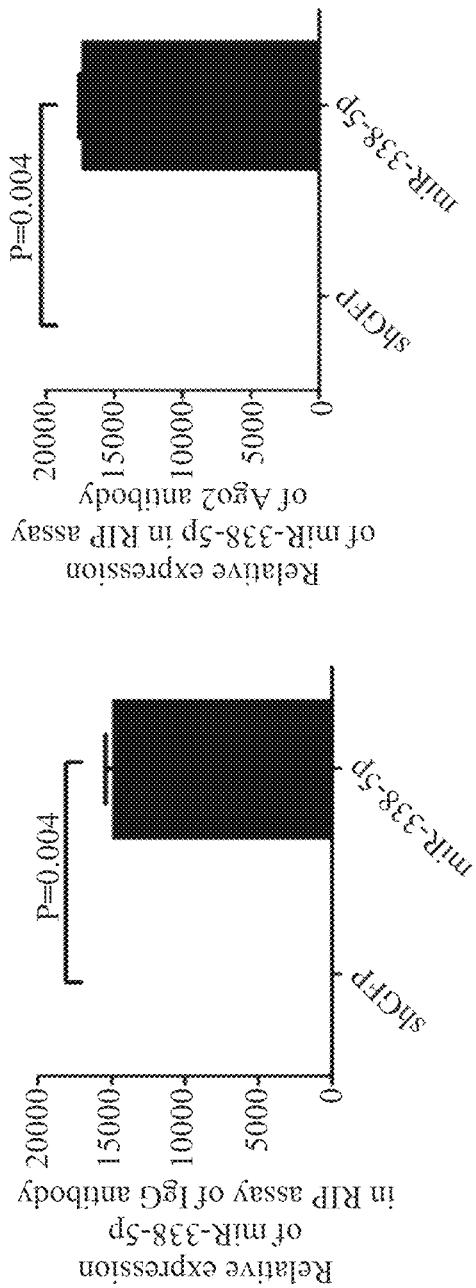
Figure 4D:
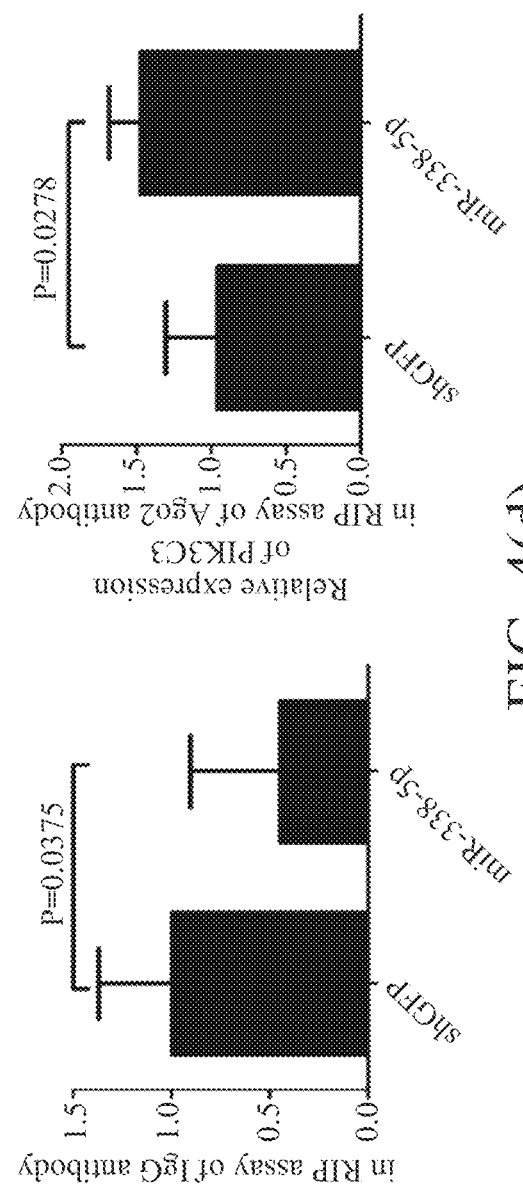

Protein argonaute-2 (Ago2) is the core of RNAi-induced silencing complex (RISC). In RNAi pathway, RISC binds to miRNA and its target gene, resulting in either mRNA degradation or translational repression. FIG. 4(a) showed the Western blot result used to confirm the quality of RIP. Western blot is a widely acknowledged technique to measure protein expression and can be routinely carried out by a skilled person in the art. Western blot in this embodiment was carried out with antibodies (Abs) to EIF2C2/AGO2 (RN003M, MBL International, Nagoya, Japan), PIK3C3 (#4263; Cell Signaling Technology, Beverly, Mass.) and β-actin (A5441; Sigma-Aldrich, St. Louis, Mo.). The result in FIG. 4(b) showed that compared with anti-IgG group, Ago2 antibody specifically precipitated with miR-338-5p in shGFP control cell lines (P=0.004, Mann-Whitney test), indicating that miR-338-5p is bound to Ago2. When IgG or Ago2 was precipitated, higher expression of miR-338-5p was demonstrated in miR-338-5p overexpressed cells than in shGFP control cells (P=0.004, Mann-Whitney test), as shown in FIG. 4(c). Compared with shGFP control cells, as shown in FIG. 4(d), a lower level of PIK3C3 mRNAs was observed in RIP-IgG lysate of miR-338-5p overexpressed cells (P=0.0375, Mann-Whitney test), indicating that miR-338-5p suppresses the mRNA expression of PIK3C3. In contrast, a higher level of PIK3C3 RNAs was demonstrated in RIP-Ago2 lysate of HCT116 cells with stable overexpression of miR-338-5p. These results indicate that PIK3C3 RNA binds to miR-338-5p.

Figure 5A:
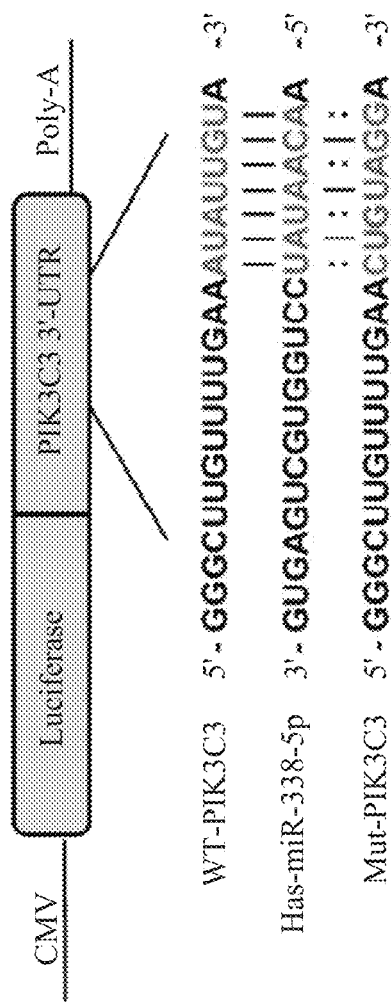
FIGS. 5(a) to 5(c) show PIK3C3 as the target gene of miR-338-5p in CRC.

Further, wild-type (WT-PIK3C3, SEQ ID NO.: 7) and mutant-type (Mut-PIK3C3, SEQ ID NO.: 8) PIK3C3 3'-UTR target sequences were constructed to confirm PIK3C3 as the target gene of miR-338-5p. As shown in FIG. 5(a), the wild-type (WT-PIK3C3, SEQ ID NO.: 7) and mutant-type (Mut: PIK3C3, SEQ ID NO.: 8) target sequences of PIK3C3 were constructed into 3'-UTR of p-miR-reporter luciferase plasmid downstream of the luciferase gene.

TABLE 9

Wild-type (WT) and mutant-type (Mut) PIK3C 3'-UTR target sequences constructed into 3'-UTR of p-miR-reporter luciferase plasmid

| Name | Sequence | SEQ ID NO. |
|---|---|---|
| WT- PIK3C3 | 5'-GGG-CUU-GUU-UUG-AAA-UAU-UGU-A-3' | 7 |
| Mut- PIK3C3 | 5'-GGG-CUU-GUU-UUG-AAC-UGU-AGG-A-3' | 8 |

The SW480 cells were then transfected with the WT or Mut p-miR-PIK3C3 plasmid (5 µg/mL) and co-transfected with miR-338-5p, anti-miR-338-5p, N.C. or anti-N.C. (100 nM), respectively. Cell lysate was obtained from the transfected cells and assayed using Dual-Glo Luciferase Assay System (E1960, Promega, Madison, Wis.), and the results were measured using a luminometer (EG&G Berthold, Wildbad, Germany).

Figure 5B:
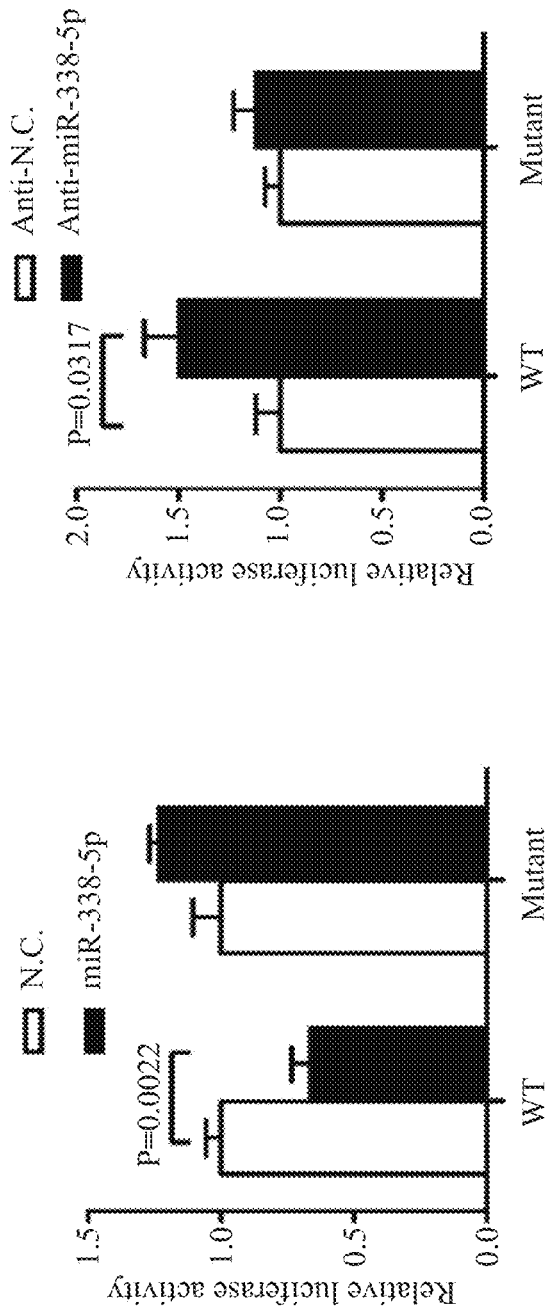

As shown in FIG. 5(b), markedly lower luciferase activity of p-miR-PIK3C3 (P=0.002, Mann-Whitney test) was observed after both miR-338-5p and WT p-miR-PIK3C3 had been transfected into SW480 cells. In contrast, significantly higher p-miR-PIK3C3 luciferase activity (P=0.0317, Mann-Whitney test) was demonstrated after miR-338-5p inhibitor had been transfected into SW480 cells. However, this regulatory effect was abolished when Mut p-miR-PIK3C3 luciferase reporter plasmid was transfected into SW480 cells. These results support that miR-338-5p is targeting to 3'-UTR of PI3KC3.

Figure 5C:
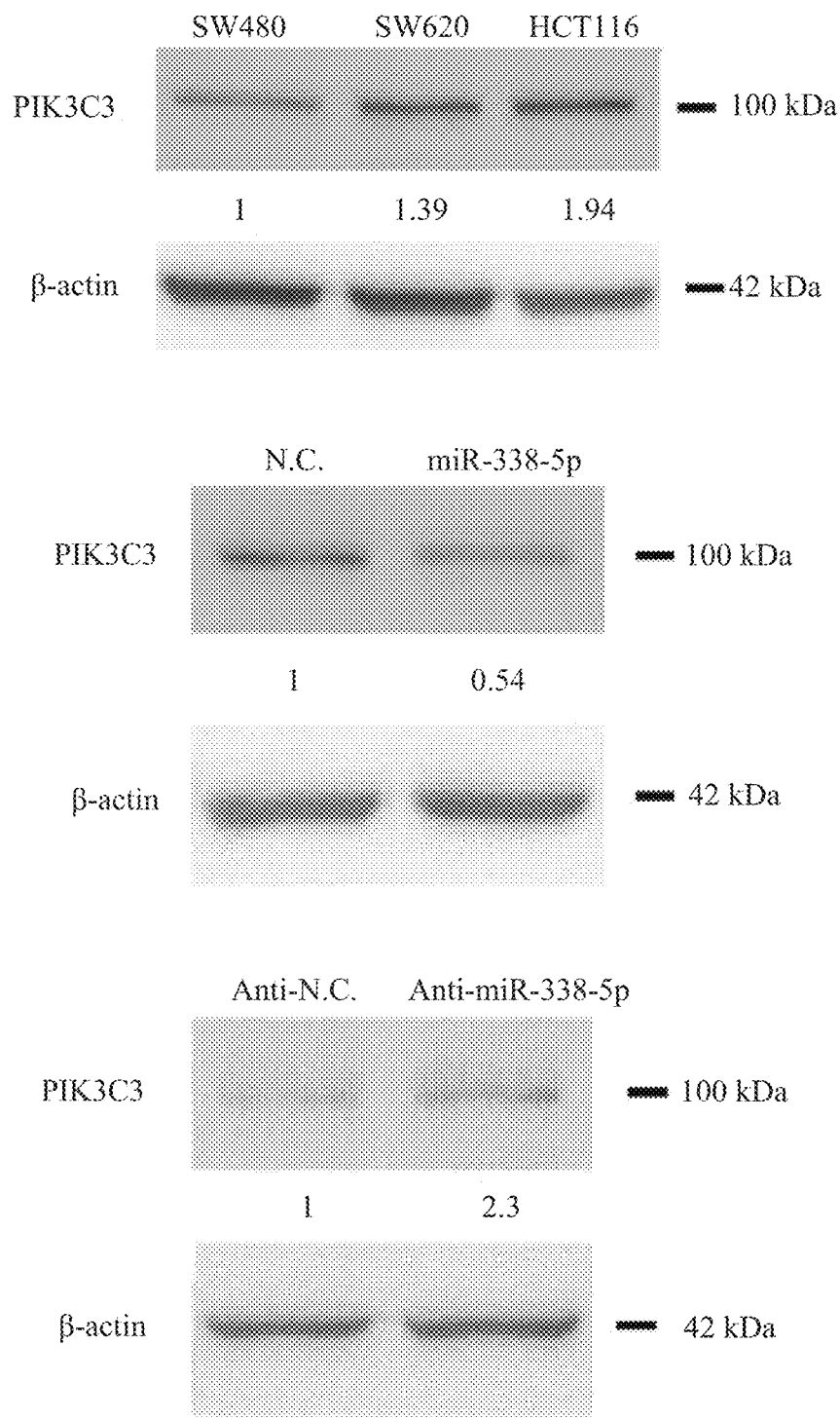

Furthermore, expression of PIK3C3 protein in CRC cell lines was evaluated using Western blot and found to be negatively correlated with that of miR-338-5p, as shown in FIG. 5(c). The SW480 cells have the lowest level of PIK3C3 protein expression, while HCT116 cells have the highest level. Also, expression of PIK3C3 in HCT116 cells was inhibited after transfection of miR-338-5p. In contrast, PIK3C3 expression was higher in SW480 cells when anti-miR-338-5p was transfected. All of these results support for PIK3C3 as the target gene of miR-338-5p in CRC.

Example 4: miR-338-5p Overexpression Triggers CRC Metastasis and Suppresses PIK3C3 Expression Involvement of miR-338-5p in the progression of CRC in vivo was investigated by establishing miR-338-5p overexpressed and PIK3C3 overexpressed stable cell lines with HCT116 cells and a xenograft mouse model. The tumorigenic potential of miR-338-5p in vivo was verified.

To establish stable PIK3C3 overexpression cell lines, the blasticidin gene (BSD) was cloned into pCMV-Vps34 plasmid (pCMV-Vps34-BSD) and transfected into HCT116 cells. The stable cell line was selected by BSD (Cyrusbioscience, Taipei, Taiwan) at 5 ng/µL. The pTRE2-BSD was used as control vector.

Stable miR-338-5p overexpression cells, miR-338-5p and PIK3C3 co-overexpressed cells, and shGFP control cells were injected into the spleens of eight-week-old female NOD/SCID mice to examine their potential impact on CRC metastasis. Each group of mice (n=5) was anesthetized using Zoletil 50 (25 mg/kg) (Virbac Laboratories, Carros, France) injected intraperitoneally (i.p.) and 2% xylazine (Rompun; Bayer HealthCare, LLC, Leverkusen, Germany) Through a 1 to 2 cm incision on the upper left lateral abdomen, cells ($1 \times 10^6$) in 100 µL of DMEM were injected into the spleen. After 42 days, the mice were sacrificed, and ascites were stained with Liu's stain for cytologic analysis.

Figure 6A:
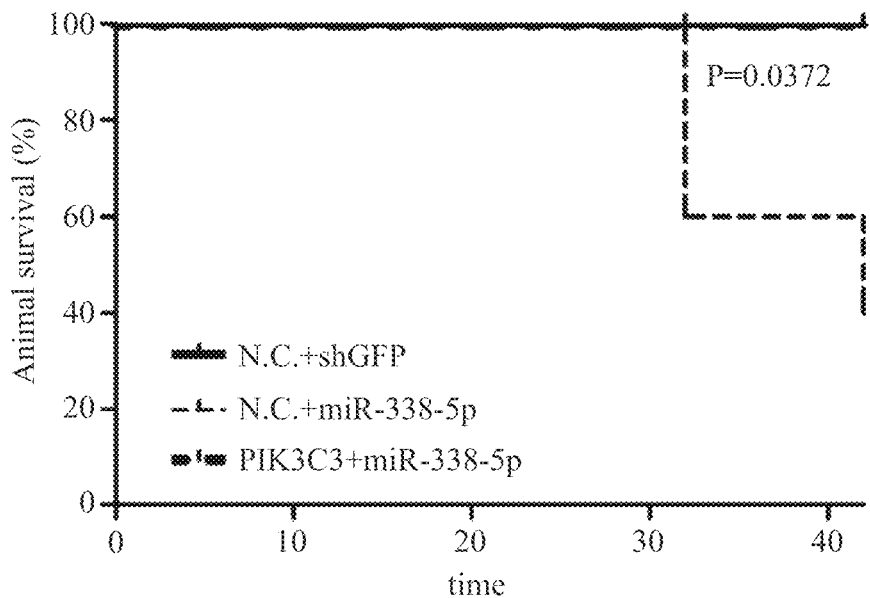
FIGS. 6(a) to 6(c) show the effect of miR-338-5p on peritoneal metastasis of CRC and its relationship to survival in vivo. Stable miR-338-5p overexpressed cells, miR-338-5p and PIK3C3 co-overexpressed cells or shGFP control cells were injected into spleen of NOD-SCID mice and analyzed for tumor metastasis.
Figure 6B:
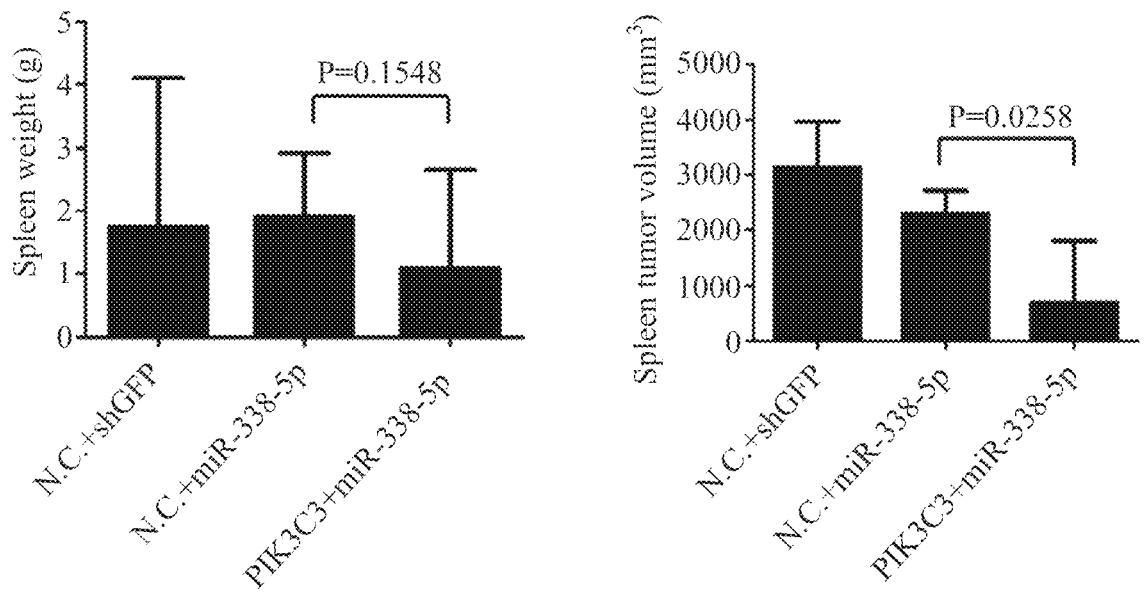

As shown in FIG. 6(a), mice injected with miR-338-5p overexpressed cells had a lower survival (P=0.0372, Log Rank test). However, when PIK3C3 was also overexpressed in stable miR-338-5p overexpression cells, survival rate of mice was recovered. FIG. 6(b) showed that overexpression of miR-338-5p did not affect tumor growth in the spleen, but when PIK3C3 was also overexpressed, spleen tumor volume reduced. The results support that overexpression of miR-338-5p negatively modulates survival of mice through suppression of PIK3C3, and PIK3C3 exhibited as a tumor suppressor in vivo and inhibited tumor growth.

Figure 6C:
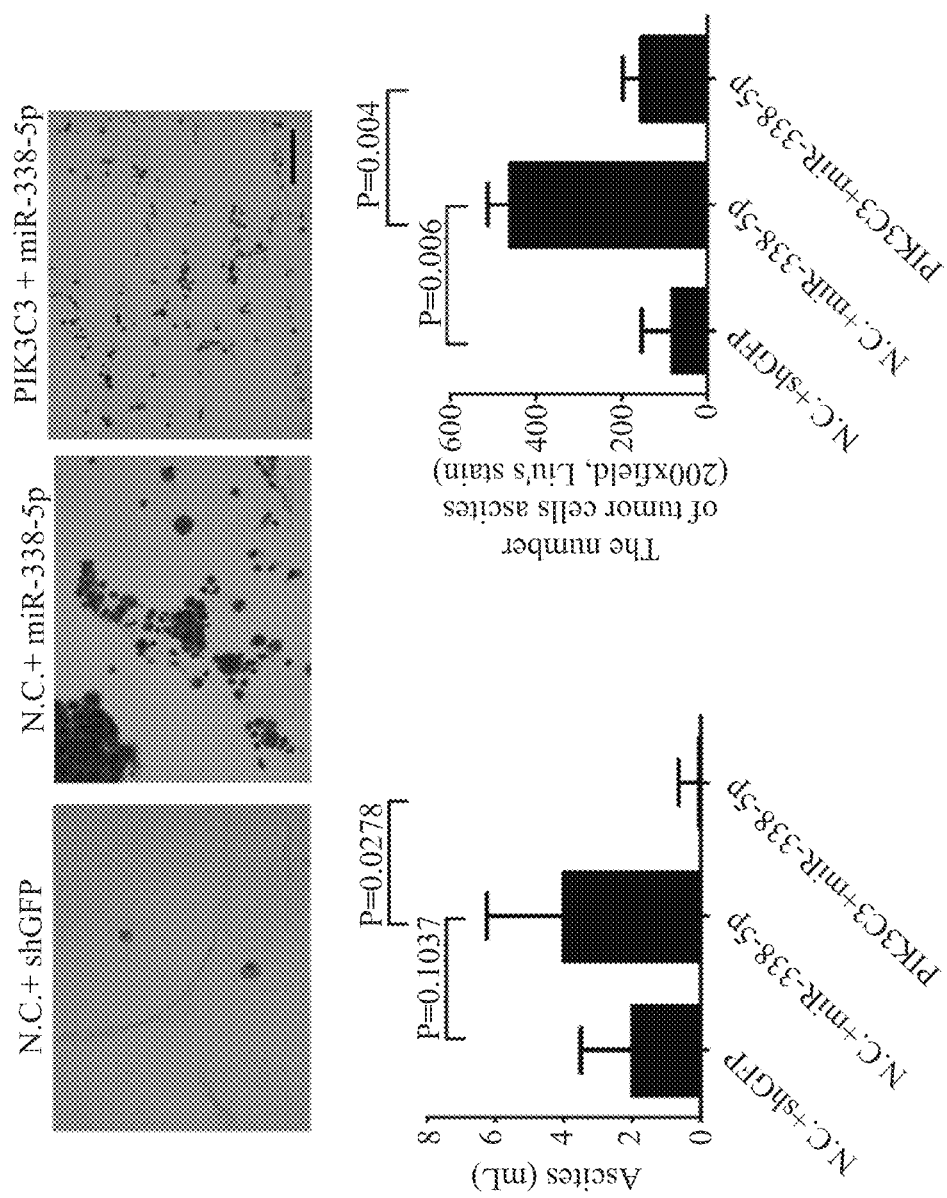

In addition, significantly greater number of tumor cells were observed in the ascites of mice with overexpression of miR-338-5p than that with shGFP control. (P=0.006, Mann-Whitney test). However, when PIK3C3 was also overexpressed in stable miR-338-5p overexpression cells, both quantity of ascites (P=0.0278, Mann-Whitney test) and number of tumor cells in the ascites (P=0.004, Mann-Whitney test) were reduced, as shown in FIG. 6(c). Therefore, miR-338-5p may promote peritoneal metastasis of CRC, and the effect could be reversed by PIK3C3.

Figure 7A:
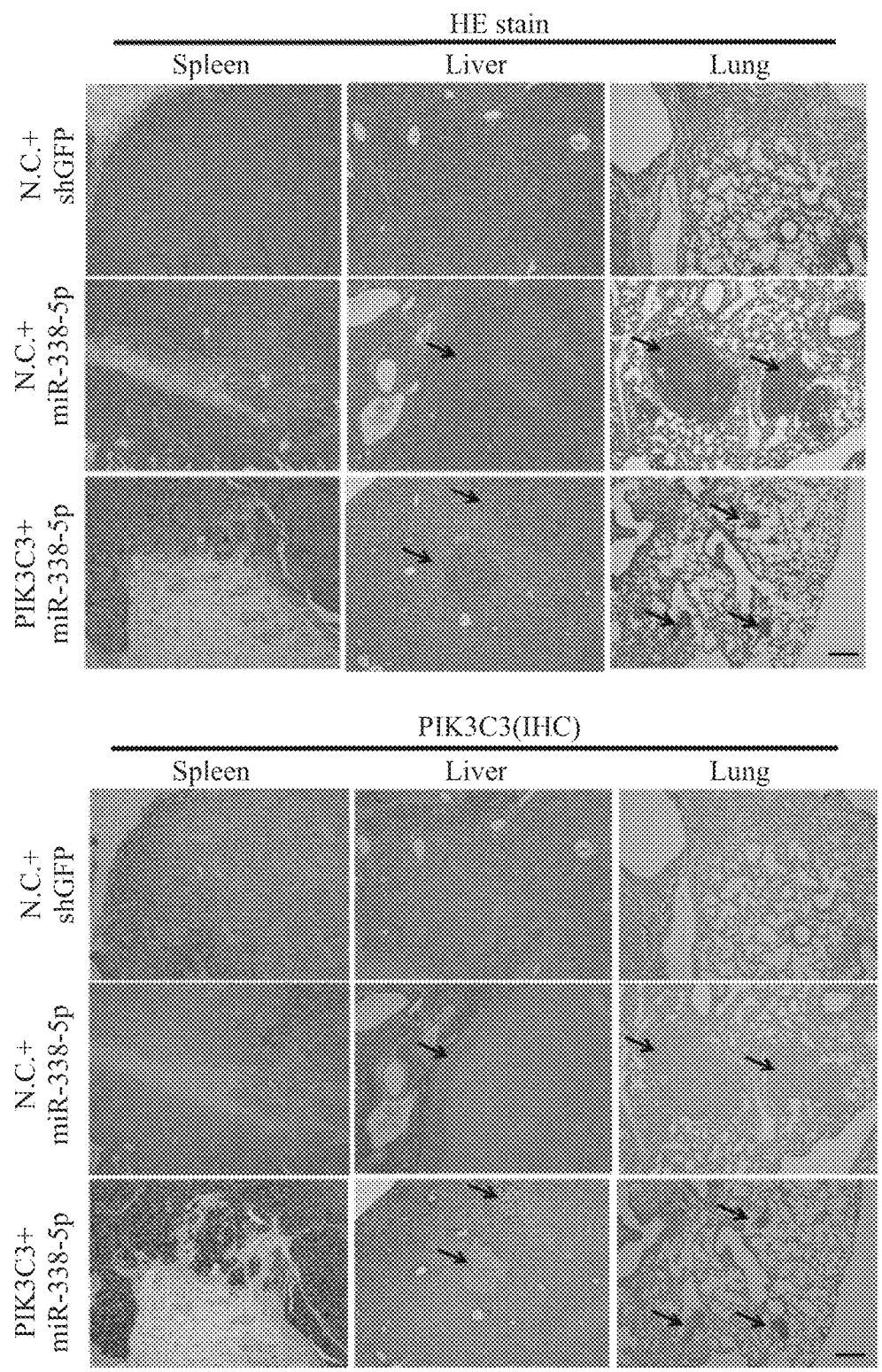
FIGS. 7(a) to 7(e) show that miR-338-5p promotes CRC metastasis in vivo and could be inhibited by PIK3C3.
Figure 7B:
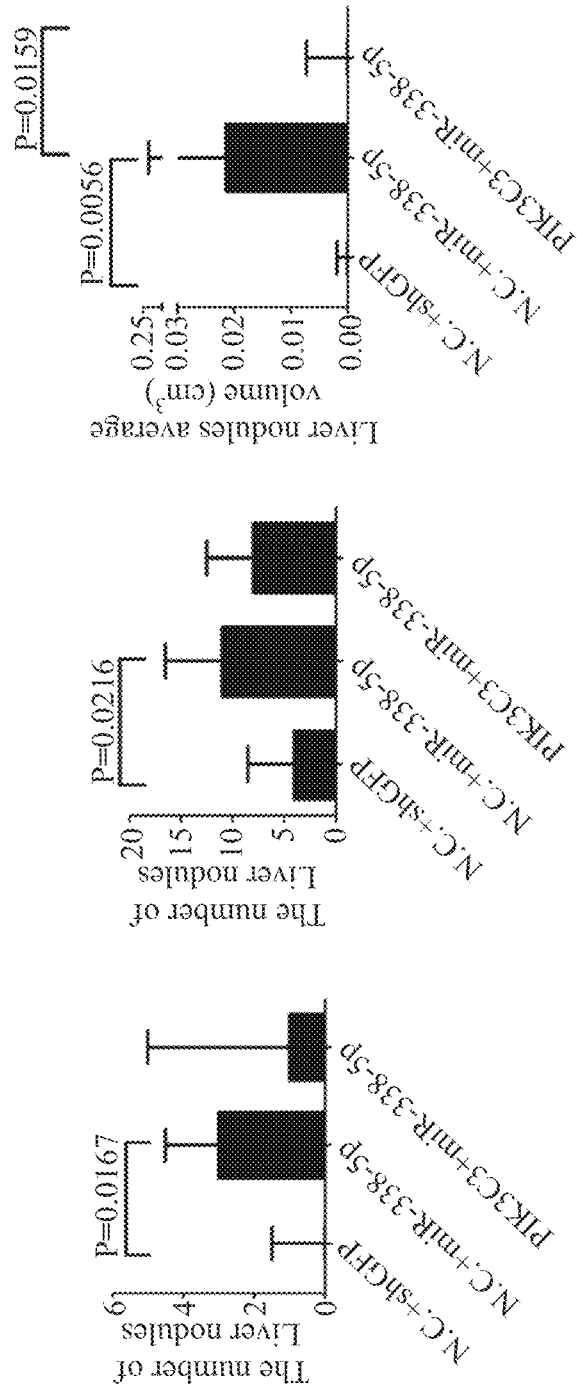

Moreover, as shown in FIGS. 7(a) and 7(b), significantly increased metastatic nodules were observed in the livers (P=0.0167, Mann-Whitney test) and lungs (P=0.0216, Mann-Whitney test) of mice after injection of stable miR-338-5p overexpression cells, and overexpression of miR-338-5p promoted the growth of metastatic nodules in the liver (P=0.0056, Mann-Whitney test), while overexpression of PIK3C3 in miR-338-5p stable cells reduced volume of metastatic nodules in the liver (P=0.0159, Mann-Whitney test).

Figure 7C:
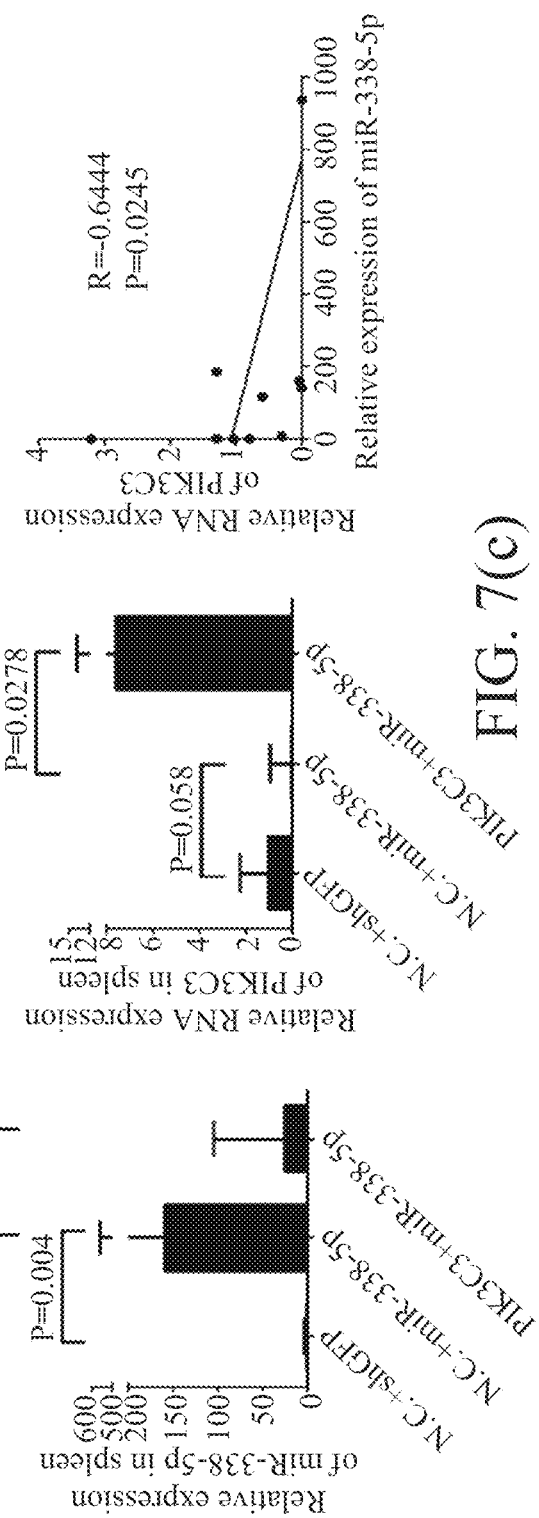

In primary xenograft tumors, expression of miR-338-5p RNAs was negatively associated with PIK3C3 levels (P=0.0245, R=−0.6444, Spearman test) when miR-338-5p was overexpressed, as shown in FIG. 7(c).

Figure 7D:
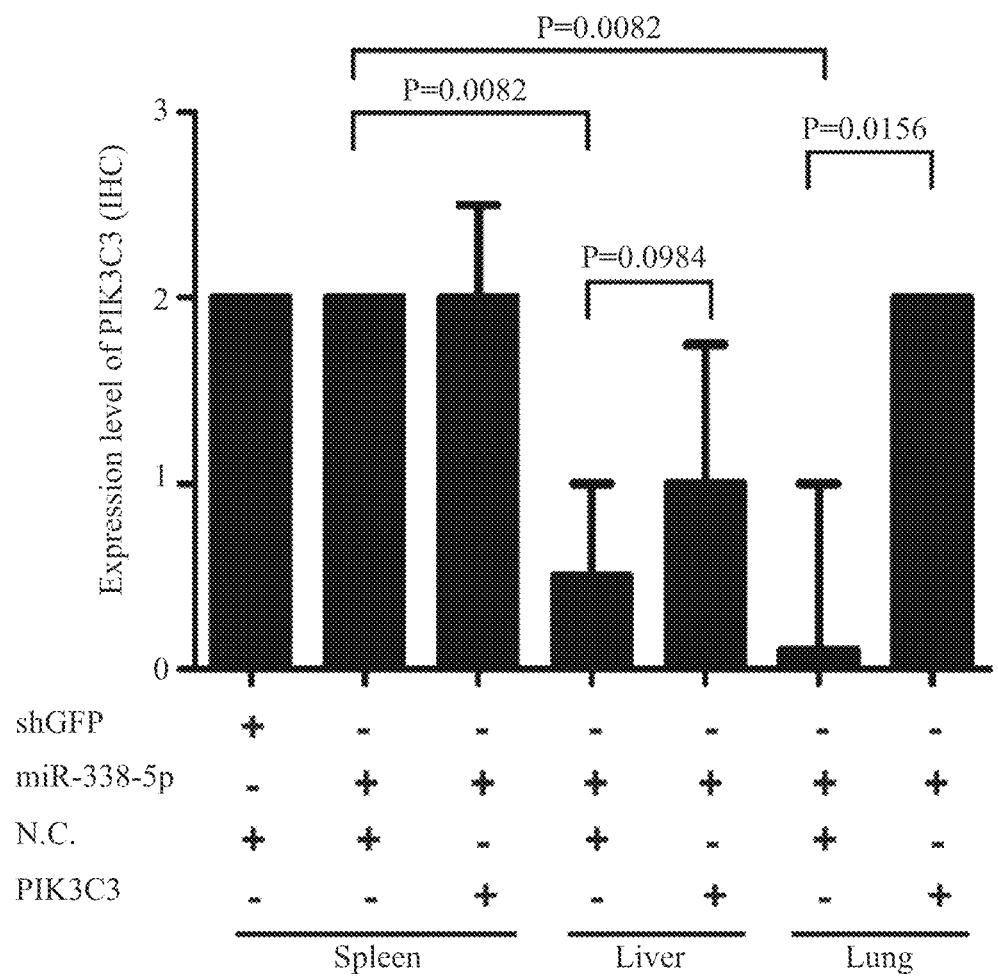

IHC using anti-PIK3C3 Ab (#4263; Cell Signaling Technology) showed that PIK3C3 protein expression in tumors with miR-338-5p overexpression is significantly higher in the spleen than that of metastatic tumors in the liver (P=0.0082, Mann-Whitney test) and lung (P=0.0082, Mann-Whitney test), as shown in FIG. 7(d). In comparison to stable miR-338-5p overexpression cells, PIK3C3 expression was higher in the tumors metastatic to the liver (P=0.0984, Mann-Whitney test) and lung (P=0.0156, Mann-Whitney test) in the mice injected with miR-338-5p and PIK3C3 co-expressed stable cells.

Figure 7E:
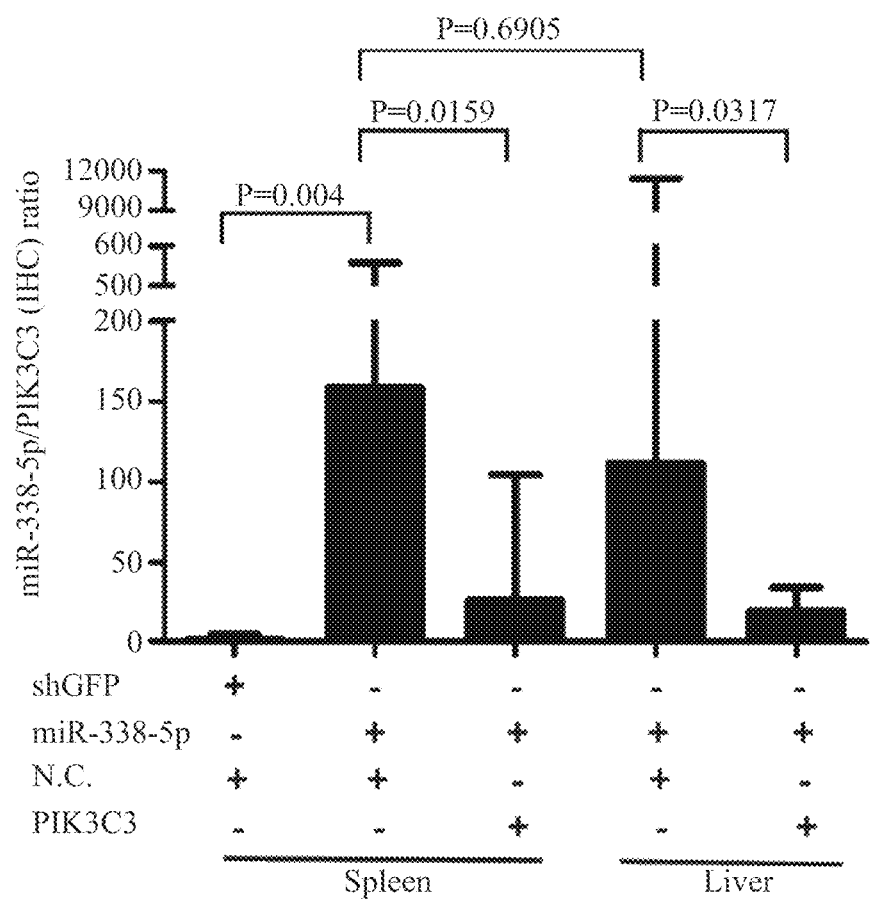

Also, as shown in FIG. 7(e), miR-338-5p/PIK3C3 ratio was higher in primary tumors with miR-338-5p overexpressed cells than in the controls (P=0.004, Mann-Whitney test), and overexpression of PIK3C3 reversed the miR-338-5p/PIK3C3 ratio in primary tumors (P=0.0159, Mann-Whitney test) and metastatic tumors in the liver (P=0.0317, Mann-Whitney test). A trend toward higher miR-338-5p/PIK3C3 ratio was observed in the metastatic tumors of liver than primary tumors in the spleen (P=0.6905, Mann-Whitney test). Therefore, miR-338-5p is involved in metastasis of CRC in vivo through silencing of PIK3C3, whereas size of metastatic tumors is reduced by PIK3C3.

Example 5: miR-338-5p Induces Migration and Invasion of CRC Through PIK3C3

Figure 8A:
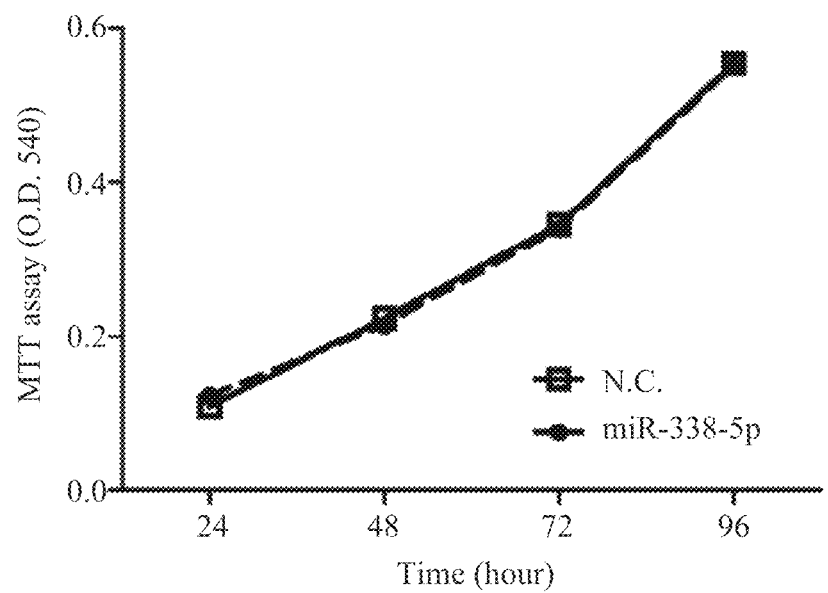
FIGS. 8(a) to 8(f) show the effect of miR-338-5p on migration and invasion in vitro assessed by wound-healing and Transwell assays.

HCT116 cells were transfected with miR-338-5p and observed for difference in growth rate with methylthiazol tetrazolium (MTT) assay. Specifically, after transfection, HCT116 cells ($8 \times 10^3$/well) were seeded in the 96-well plate and cultured for 24, 48, 72 and 96 hours, respectively. MTT solution (M2128; Sigma) (0.05 mg/mL in DMEM) was added to each well and incubated at 37° C. for 3 hours. Then, medium was removed and replaced by 100 μL dimethylsulfoxide (D4540, Sigma). A 96-well multiscanner autoreader (MRX II, Thermo Lab Systems, Franklin, Mass.) was used to measure the absorbance of formazan in cell lysate at 540 nm and calculate the number of viable cells. As shown in FIG. 8(a), no significant difference of growth rate was observed in HCT116 cells transfected with miR-338-5p.

Figure 8B:
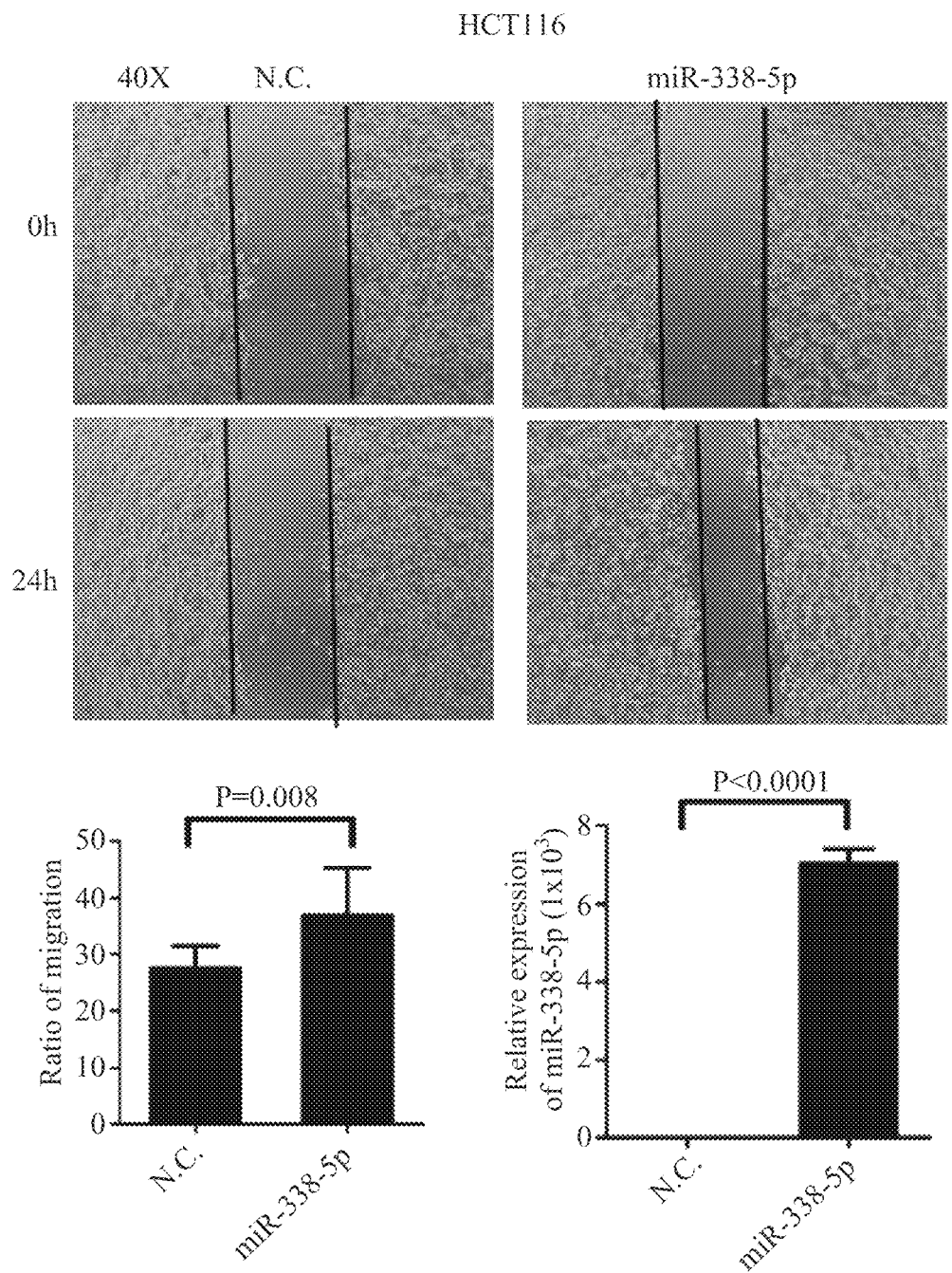
Figure 8C:
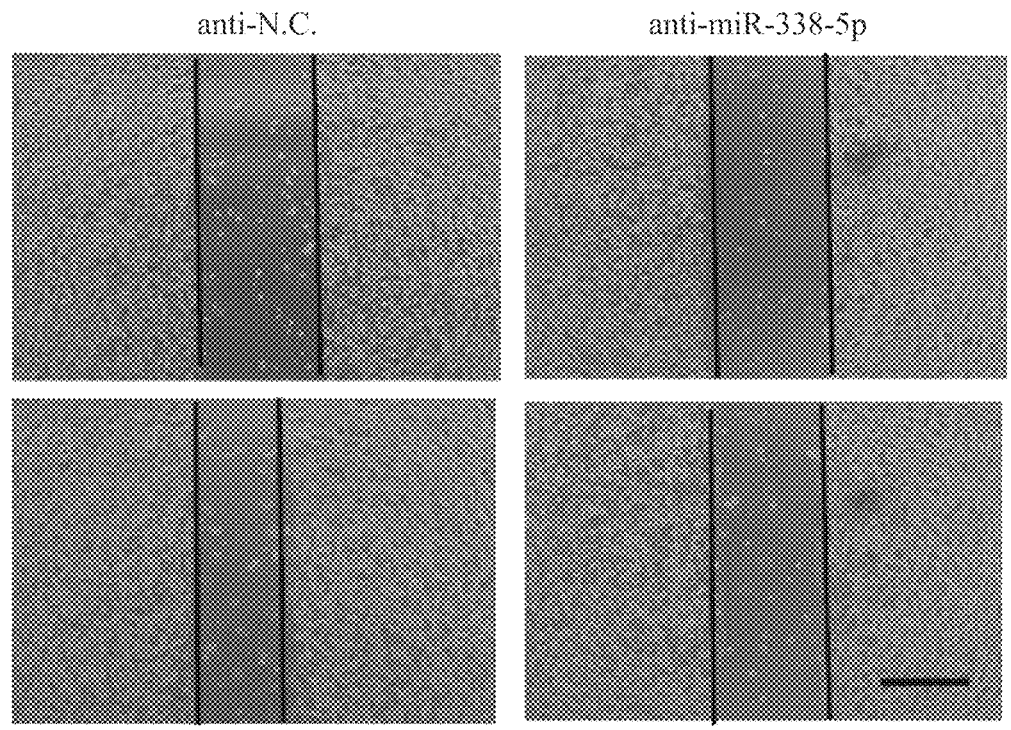
Figure 8C:
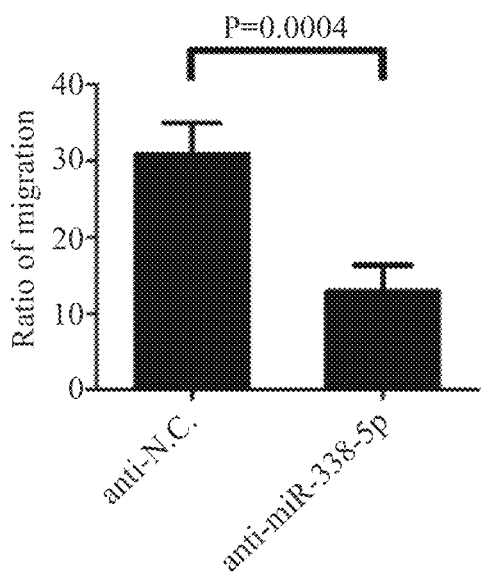
Figure 8C:
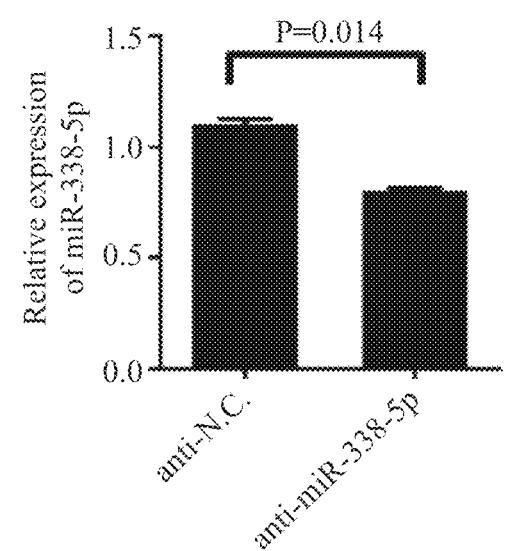
Figure 8D:
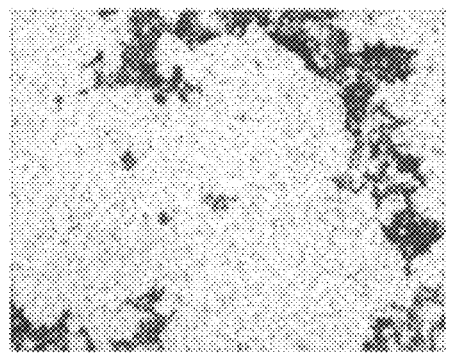
Figure 8D:
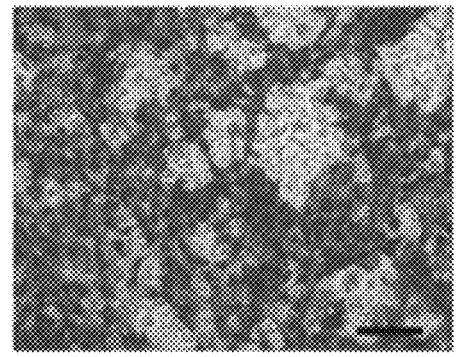
Figure 8D:
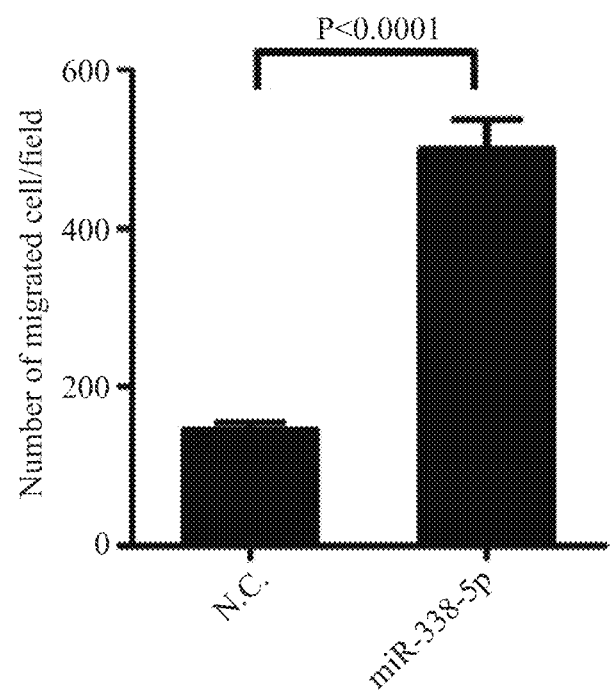
Figure 8E:
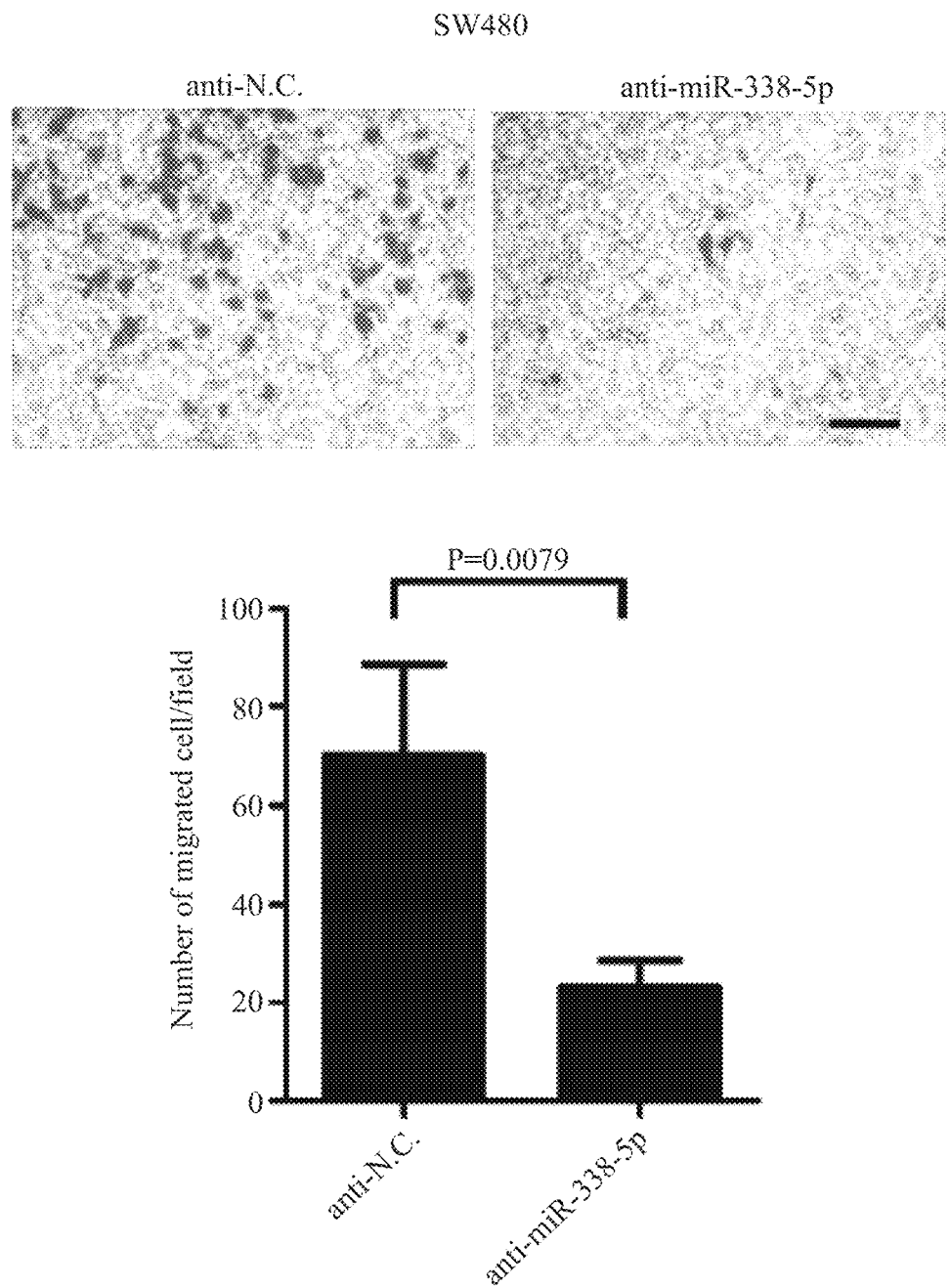
Figure 8F:
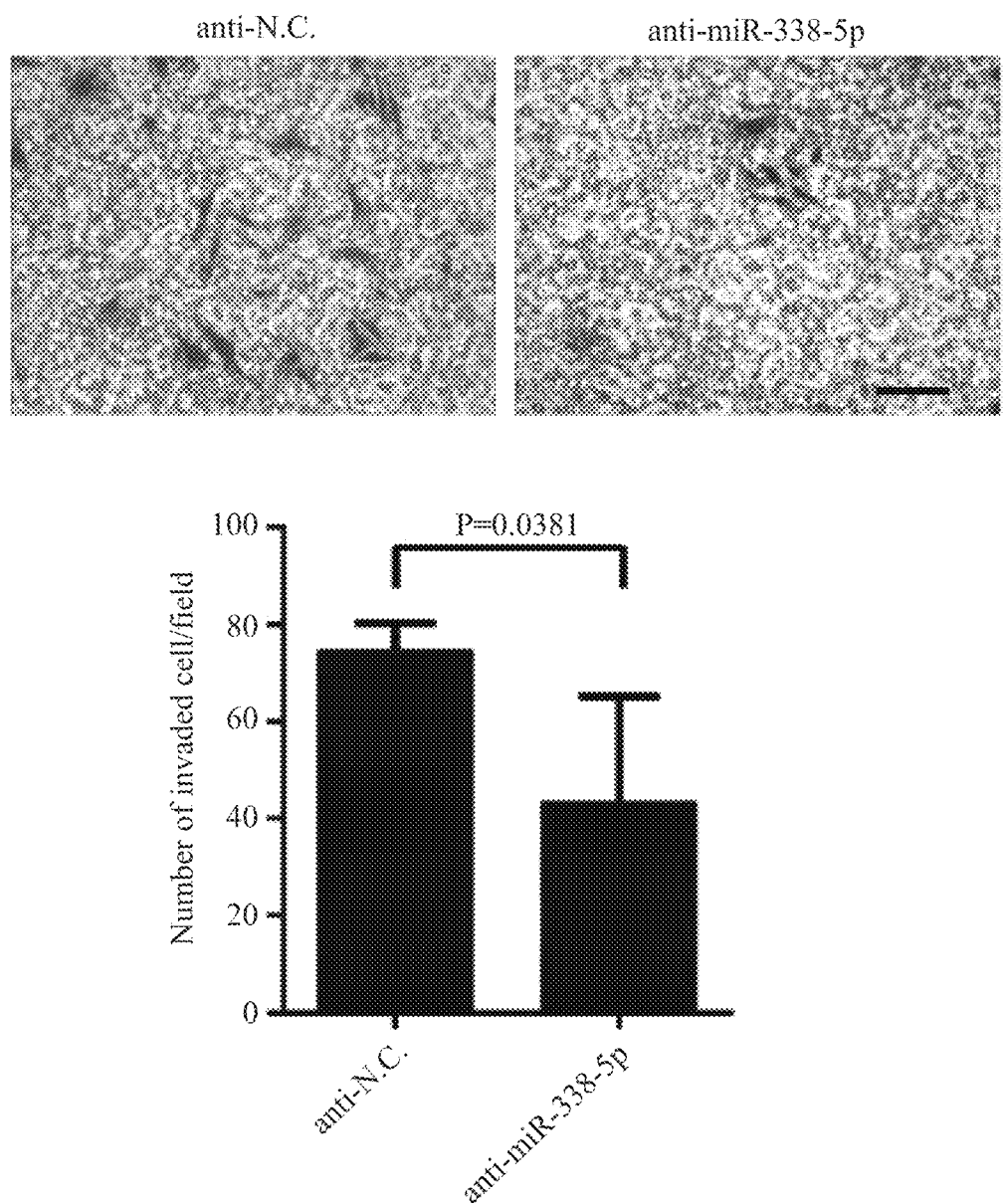

Then, HCT116 cells transfected with miR-338-5p were assessed for cell migration in vitro with a wound-healing assay analyzed at 24 h and a Transwell assay analyzed at 48 h (Corning, Corning City, N.Y.). Cell invasion in vitro was estimated using a Transwell assay, in which cells were seeded on Transwell columns coated with a Matrigel membrane (BD Biosciences, San Jose, Calif.). Then, cells on the bottom of membrane were counted after 96 h. The results as shown in FIGS. 8(b) and 8(d) revealed that significantly higher cell migration is observed in miR-338-5p-transfected HCT116 cells by both wound-healing and Transwell migration assays. In contrast, anti-miR-338-5p transfection significantly inhibited the migration, as shown in FIGS. 8(c) and 8(e) and also shown by Transwell invasion of SW480 cells (FIG. 8(f)). Thus, miR-338-5p promotes CRC migration and invasion in vitro.

Figure 9A:
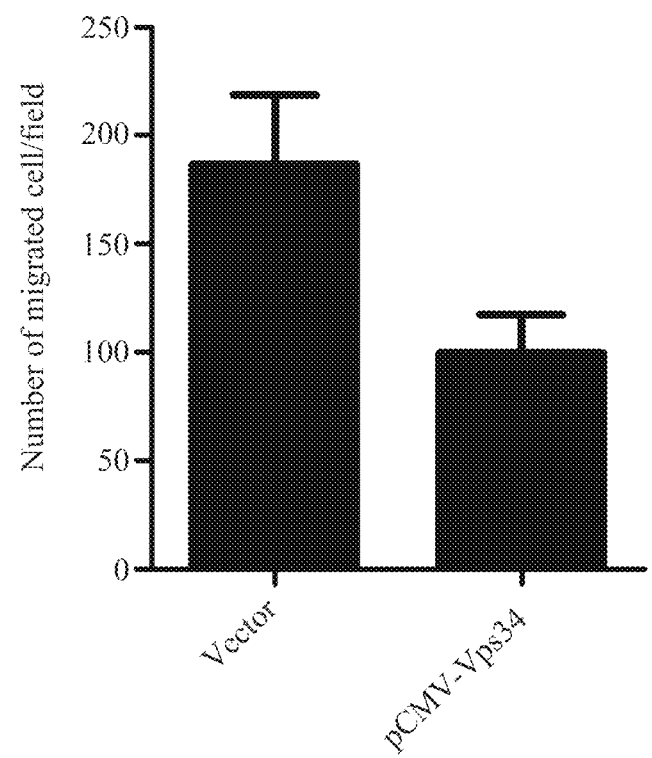
FIGS. 9(a) and 9(b) show the result of PIK3C3's inhibition on the migration and invasion of CRC in vitro.
Figure 9B:
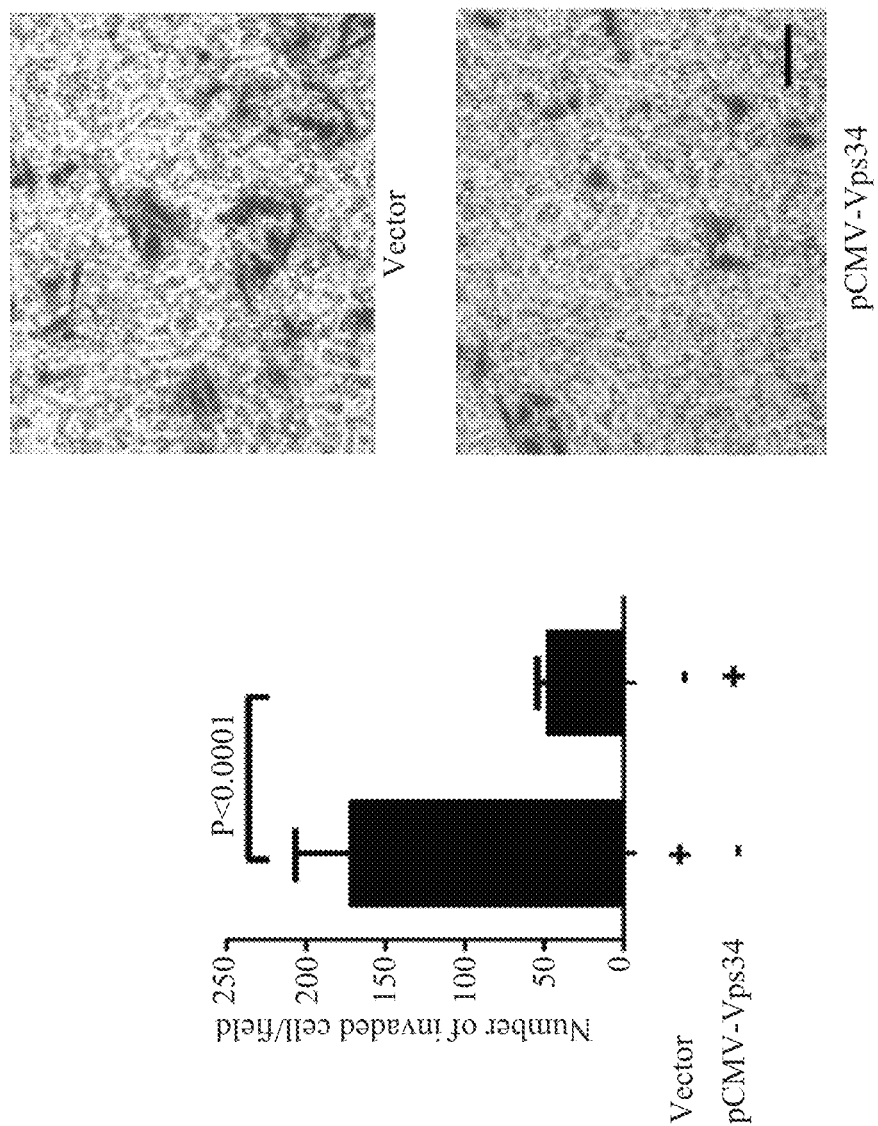
Figure 10A:
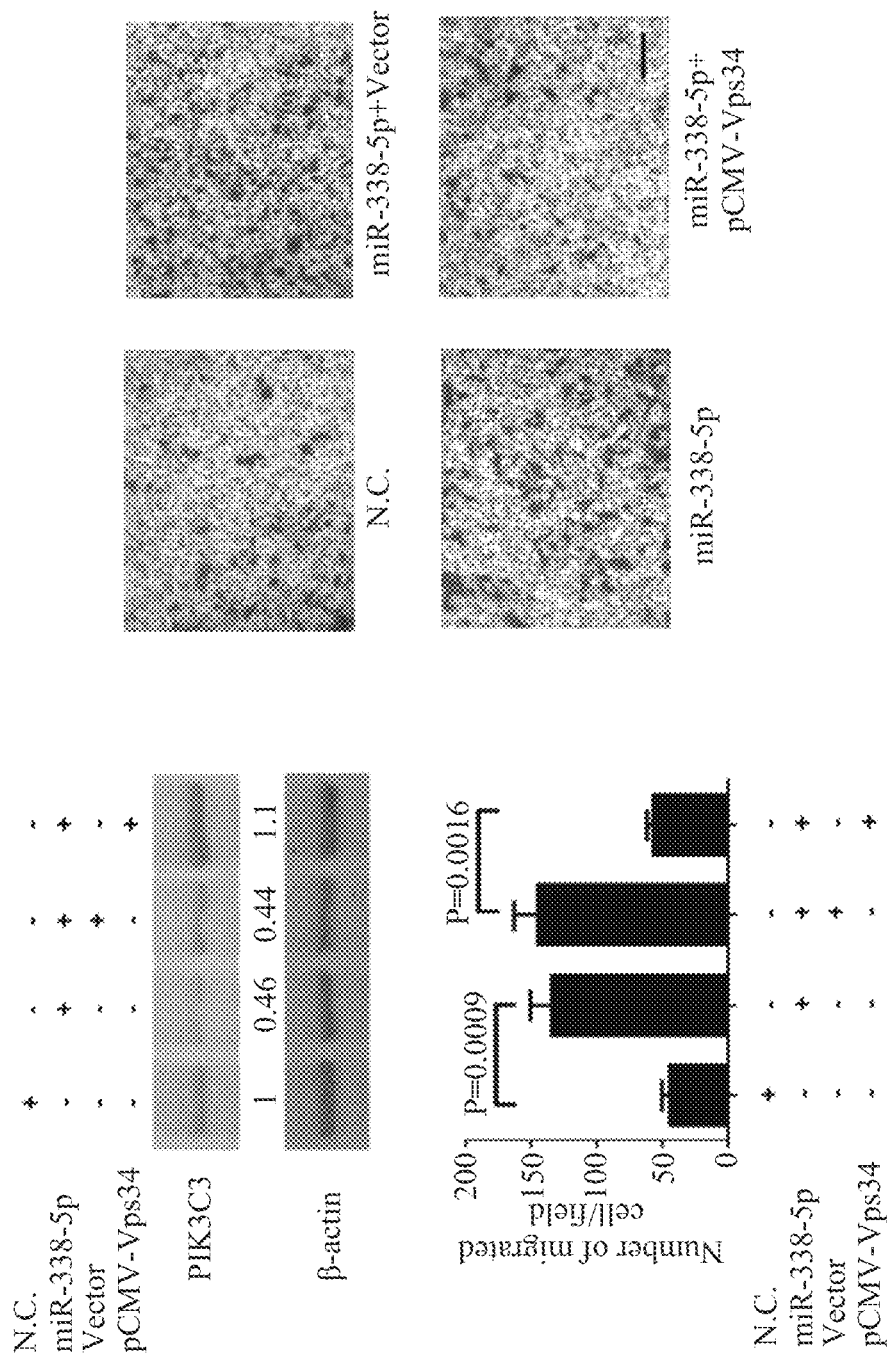
FIGS. 10(a) to 10(c) show the involvement of PIK3C3 in miR-338-5p mediated cell migration and invasion.
Figure 10B:
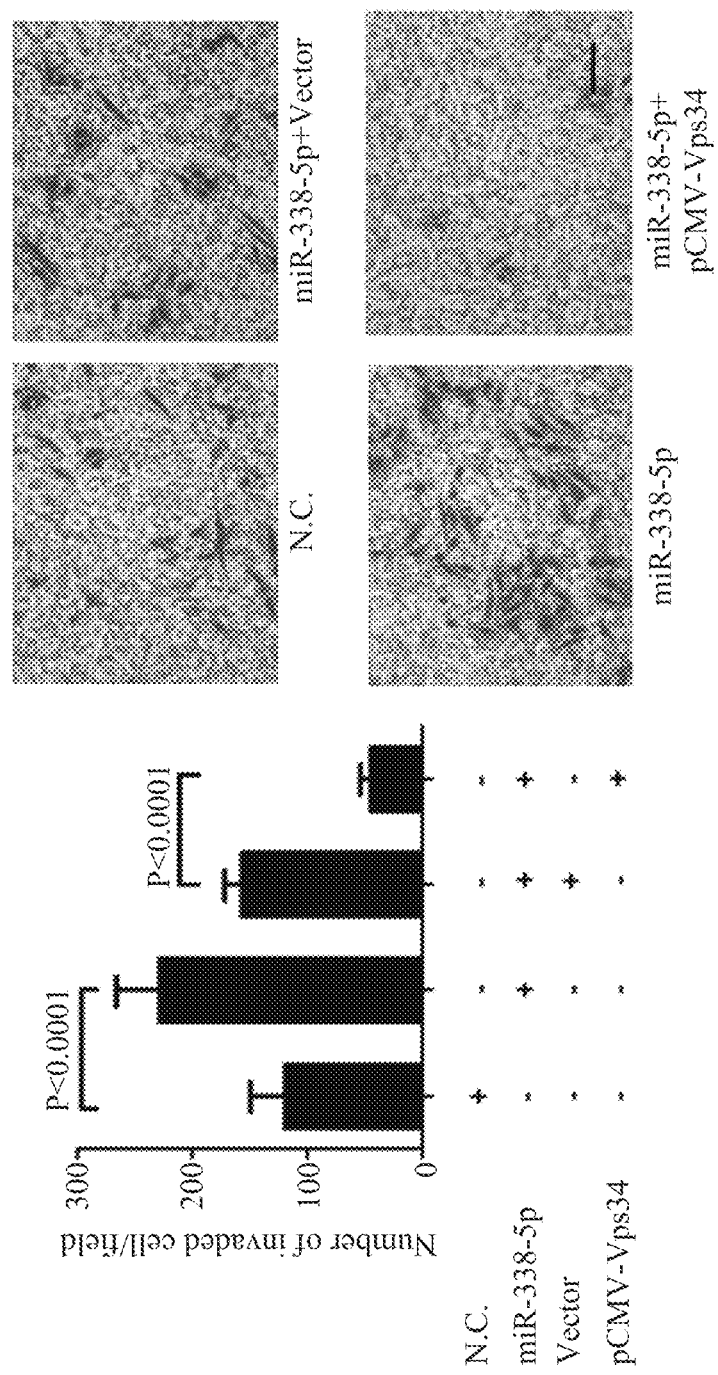
Figure 10C:
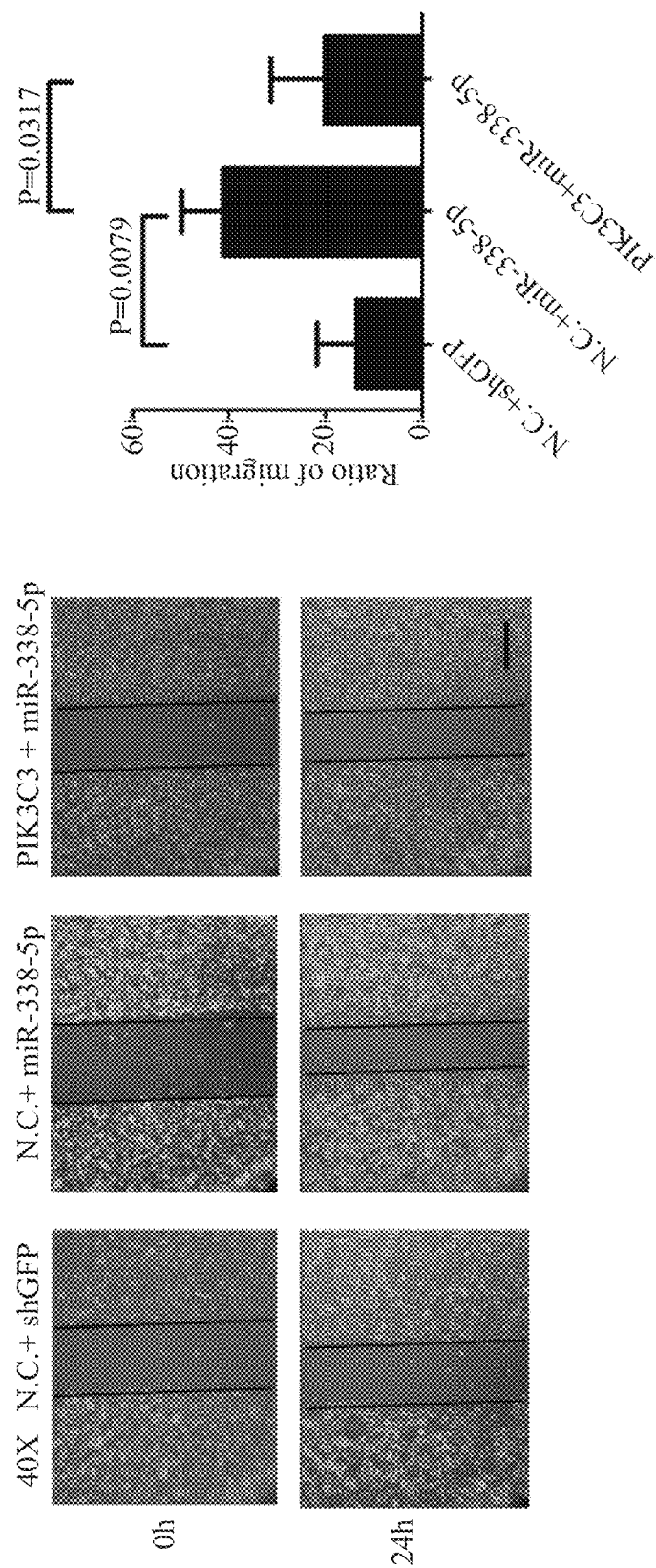

The involvement of PIK3C3 in miR-338-5p mediated processes was investigated by preparing pCMV-Vps34 (PIK3C3) vector for experiments in vitro. The pCMV-Vps34 plasmid was gifted by W. C. Su, China Medical University, Taichung, Taiwan. Both cell migration (P=0.0487) (FIG. 9(a)) and invasion (P<0.0001) (FIG. 9(b)) in vitro were significantly inhibited in SW480 cells transfected with PIK3C3 vector. Furthermore, migration (P=0.0009, t-test) and invasion (P<0.0001, t-test) were significantly induced in SW480 cells when overexpressing miR-338-5p, and both cell migration and invasion were significantly inhibited again when PIK3C3 was reactivated (P=0.0016 and P<0.0001, t-test, respectively), as shown in FIG. 10(a) and FIG. 10(b). Wound healing assay using HCT116 stable cells confirmed that overexpression of PIK3C3 rescues the inhibition of cell migration by overexpressing miR-338-5p as shown in FIG. 10(c).

Figure 11A:
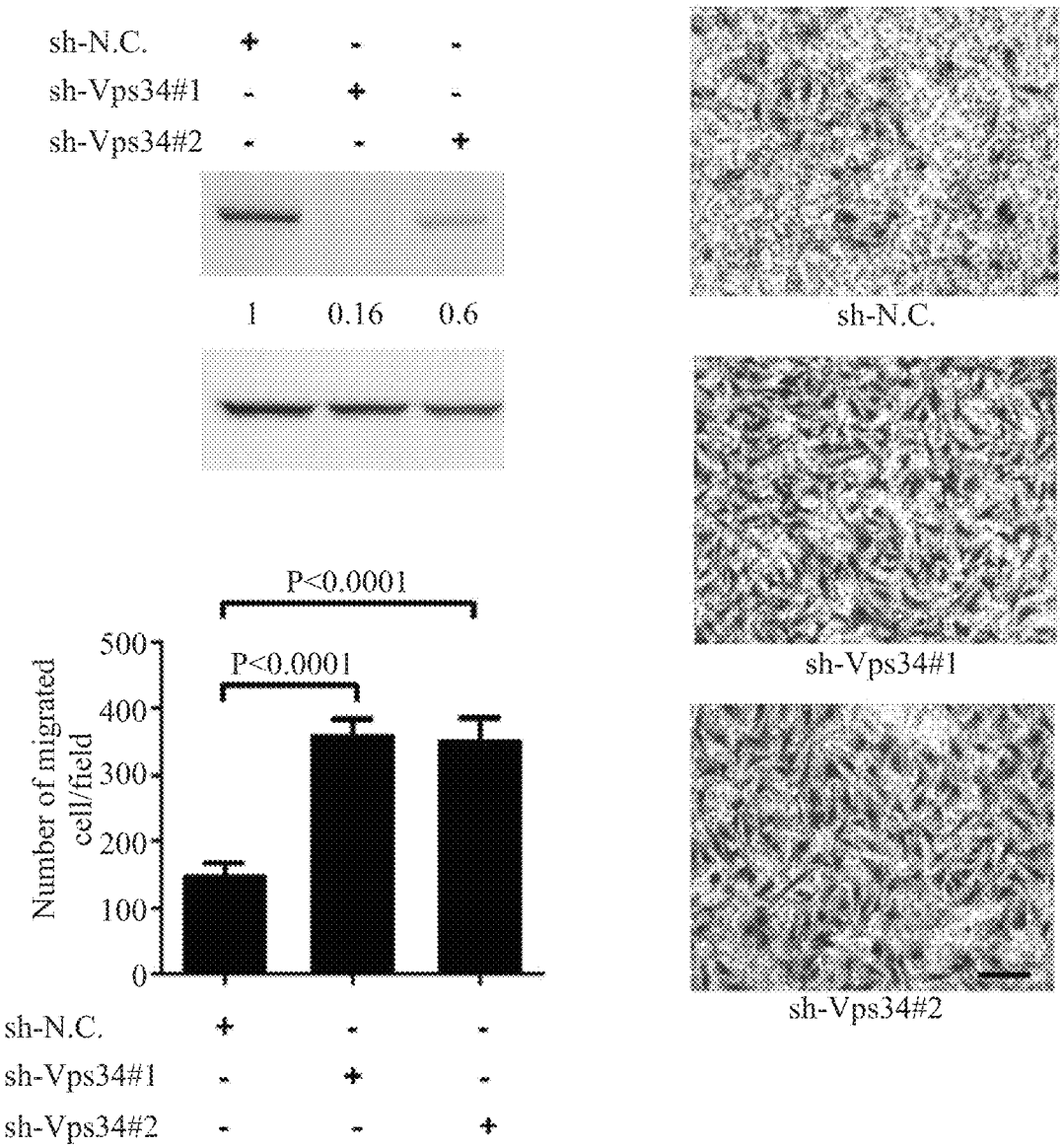
FIGS. 11(a) and 11(b) show the result of inhibition of PIK3C3's induction on migration and invasion of CRC in vitro.
Figure 11B:
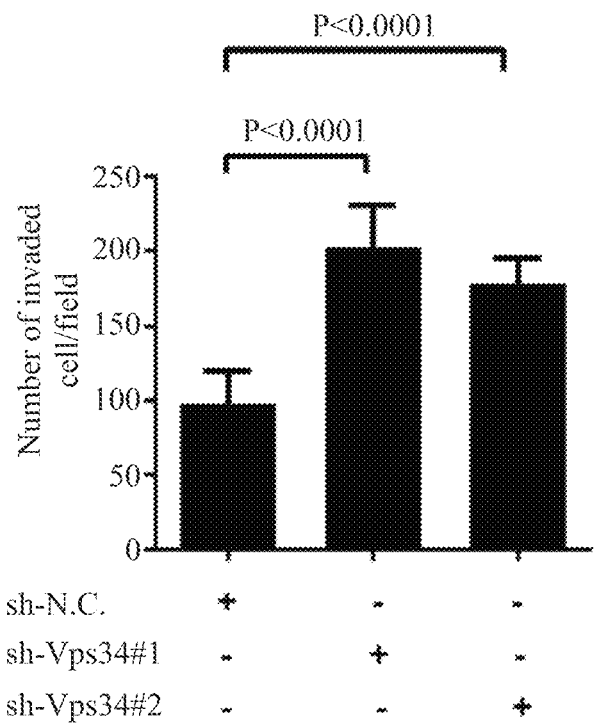
Figure 11B:
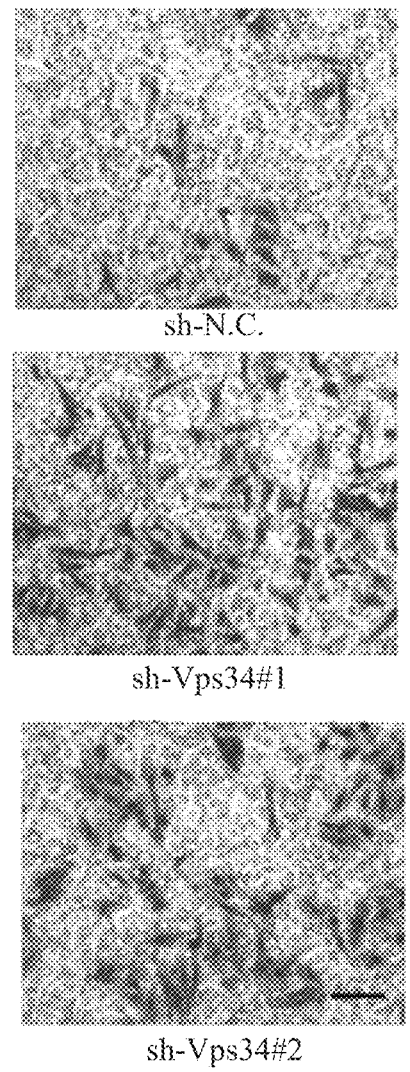

Conversely, as shown in FIGS. 11(a) and 11(b), inhibition of PIK3C3 expression in the cells using lentivirus for sh-Vps34 (PIK3C3) showed an increased migration and invasion of SW480 cells after transfection. The shRNAs targeting PIK3C3 (Vps34) were purchased from the National RNAi Core Facility (Academia Sinica, Taipei, Taiwan). The IDs of selected clones are: TRCN0000037794 for sh-Vps34 #1, and TRC0000296151 for sh-Vps34 #2, respectively. Lentiviruses that express shRNAs were produced according to provider's protocol. The cells were selected using puromycin (P8833; Sigma-Aldrich) at 15 ng/μL for SW480 cells and 1 ng/μL for HCT116 cells.

Figure 12A:
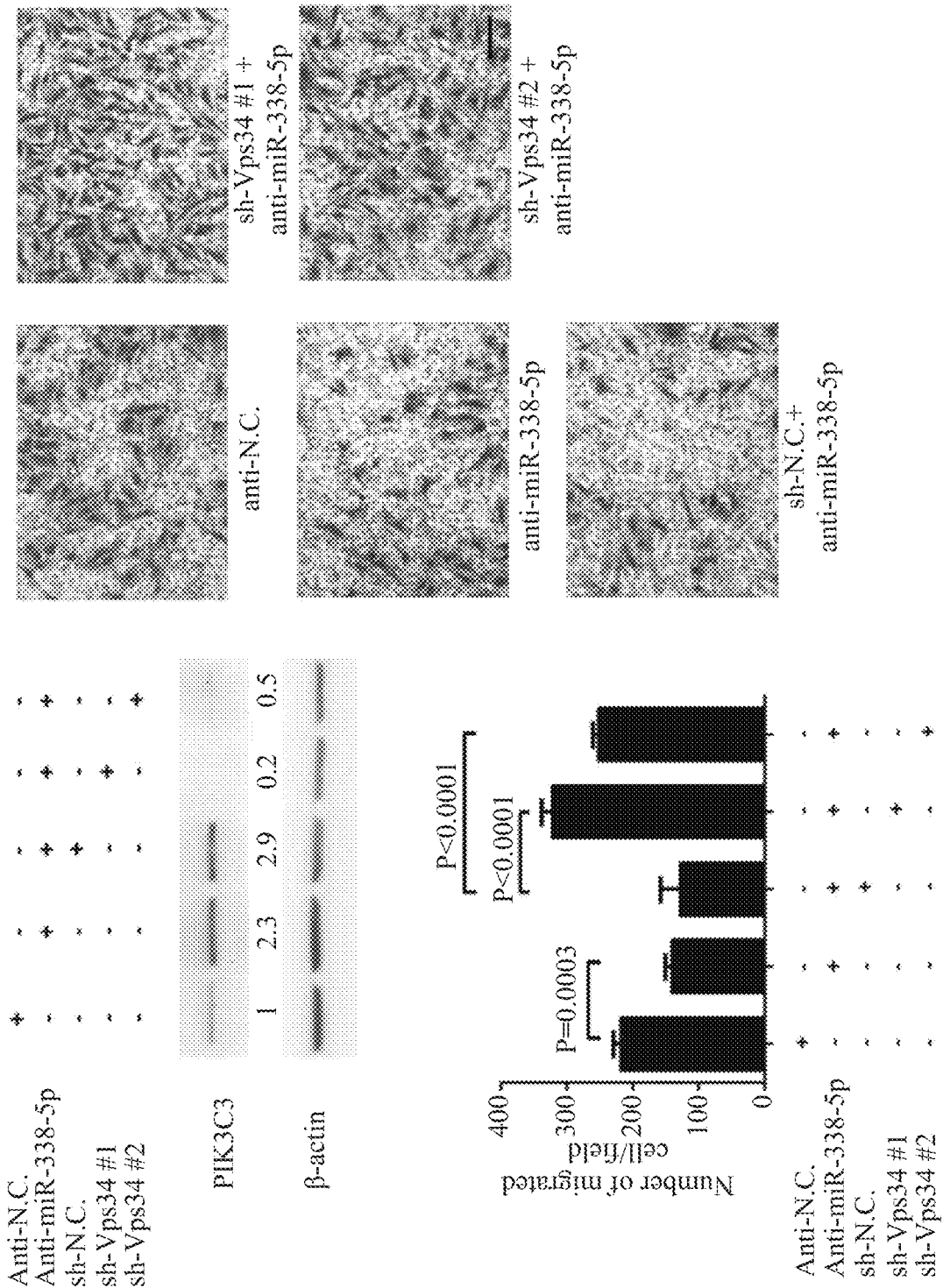
FIGS. 12(a) and 12(b) show the involvement of PIK3C3 in miR-338-5p mediated inhibition of cell migration and invasion.
Figure 12B:
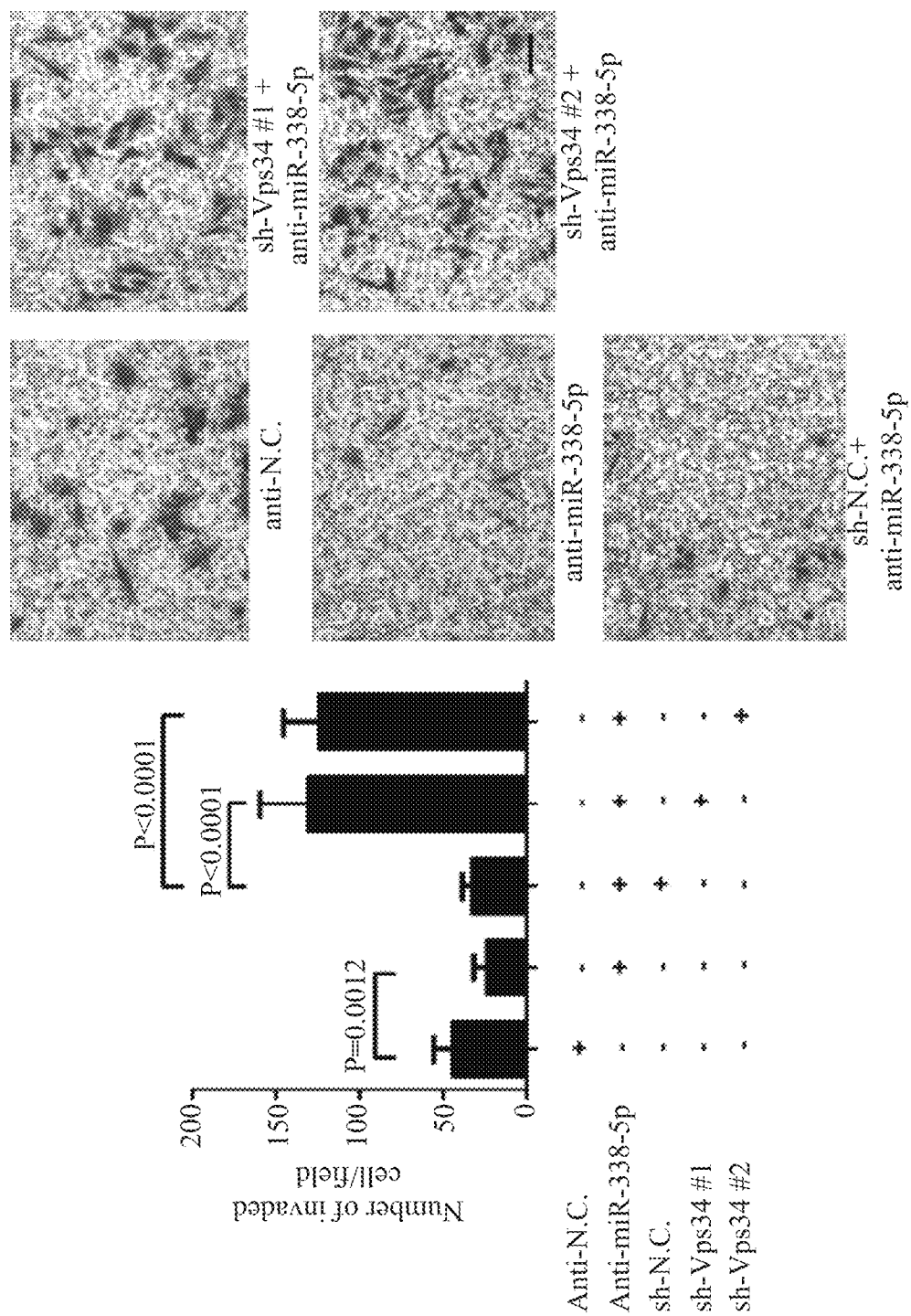

As shown in FIGS. 12(a) and 12(b), transfection of anti-miR-338-5p up-regulated the PIK3C3 expression in SW480 cells with inhibition of migration (P=0.0003, t-test) and invasion (P=0.0012, t-test). On the contrary, sh-Vps34 lentivirus transfection reversed the PIK3C3 expression and also the biologic effects of migration and invasion in vitro. The results support that miR-338-5p induces CRC migration and invasion through inhibition of PIK3C3.

Example 6: miR-338-5p Modulates CRC Through Suppression of SPRY2

As shown in Table 8 above, miR-338-5p is predicted to have many target genes. To confirm SPRY2 as one of the target genes, stable miR-338-5p overexpression and shGFP control cells were established in HCT116 cell lines for RIP assay, respectively.

Figure 13A:
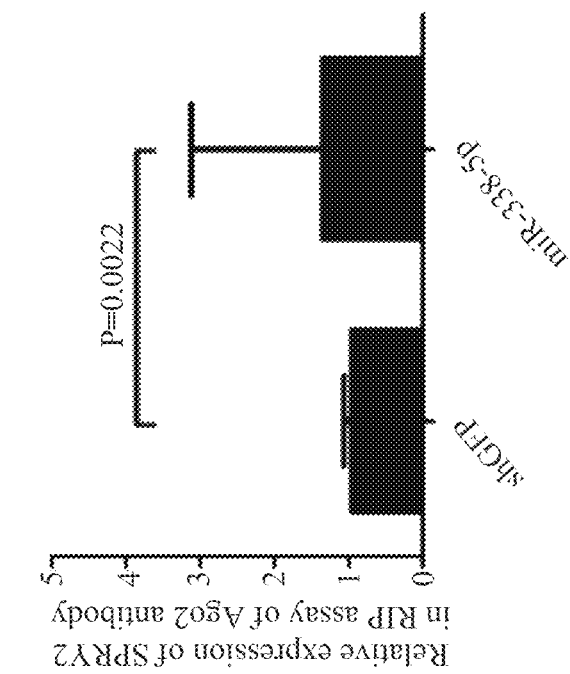
FIGS. 13(a) and 13(b) show the involvement of SPRY2 in the activation of ERK and AKT by miR-338-5p.
Figure 13A:
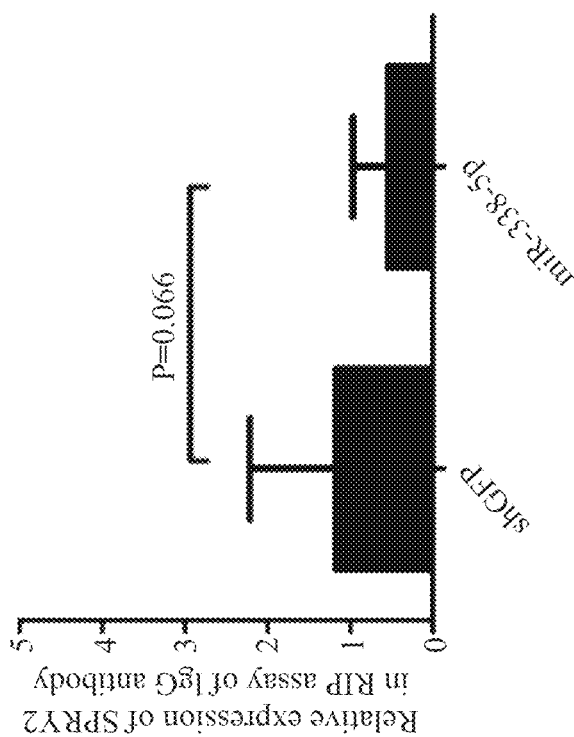

As shown in FIG. 13(a), compared to shGFP control cells, miR-338-5p overexpressed cells had a lower level of SPRY2 RNA in RIP-IgG lysate, supporting that miR-338-5p suppresses the expression of SPRY2. In contrast, a higher level of SPRY2 RNA (P=0.0022, Mann-Whitney test) was demonstrated in RIP-Ago2 lysate of stable miR-338-5p overexpression HCT116 cells. These results confirmed that SPRY2 RNA binds to miR-338-5p.

Figure 13B:
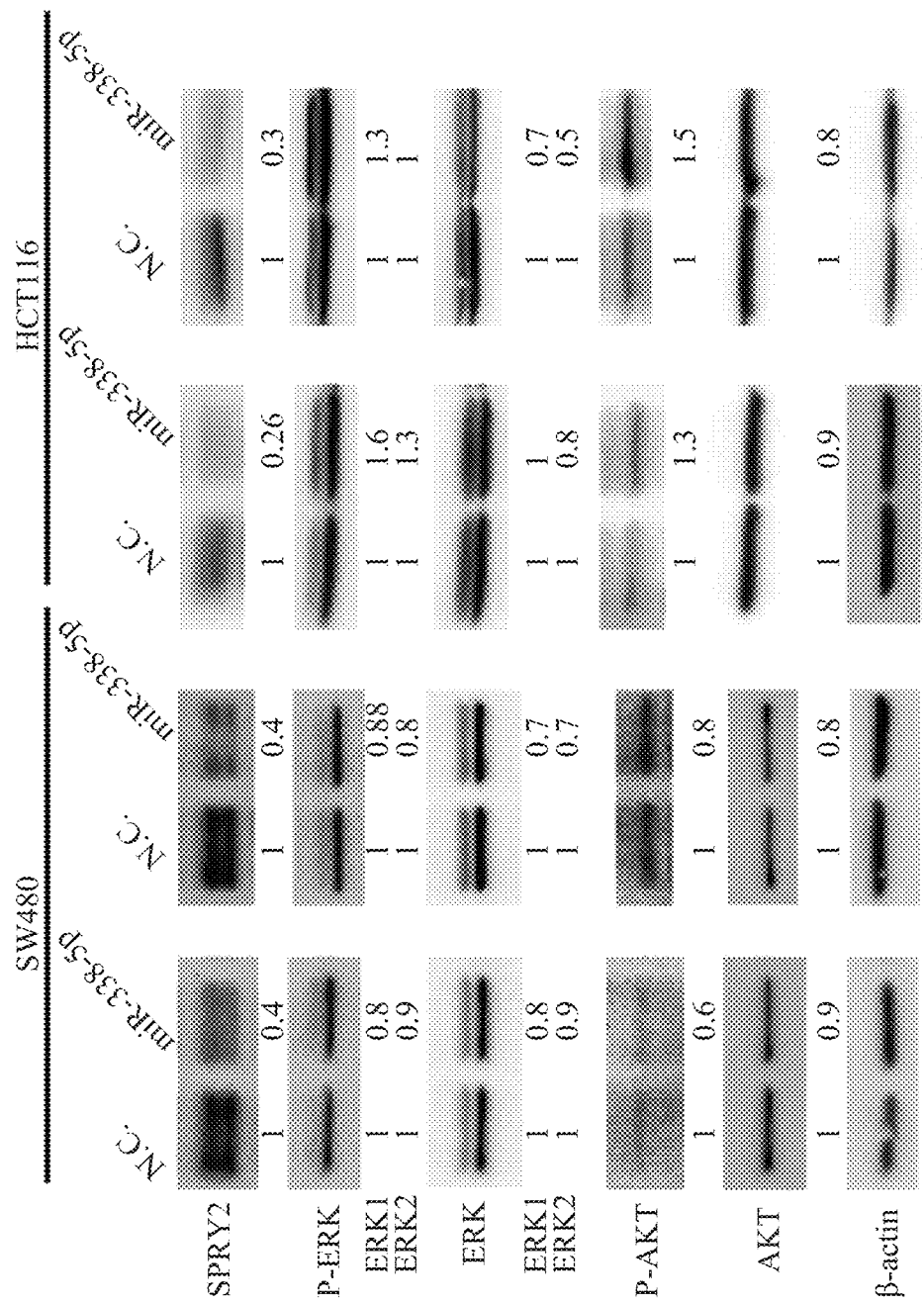

To clarify the significance of SPRY2 for CRC cells, miR-338-5p was transfected into SW480 and HCT116 cells, respectively. MiR-338-5p suppresses the expression of SPRY2 in both cell lines. However, only HCT116 cells demonstrated an induced phosphorylation of ERK and AKT by miR-338-5p, as shown in FIG. 13(b). This result suggests that miR-338-5p suppresses SPRY2 with activation of ERK and AKT signaling in HCT116 cells, whereas other pathway (s), independent of ERK and AKT, may be involved in SW480 cells.

Figure 14A:
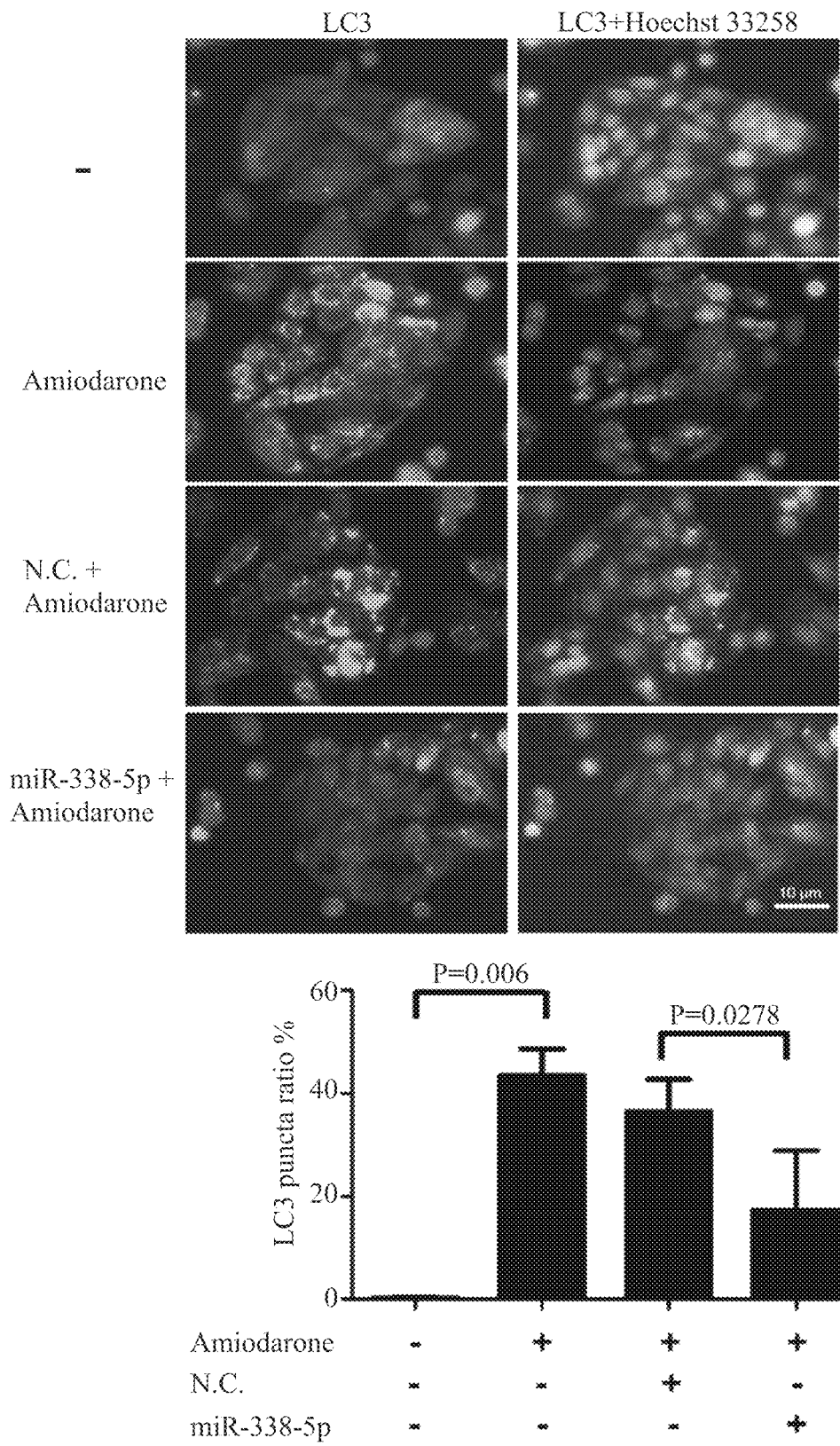
FIGS. 14(a) to 14(f) show the involvement of autophagy in miR-338-5p-related CRC migration and invasion in vitro.
Figure 14B:
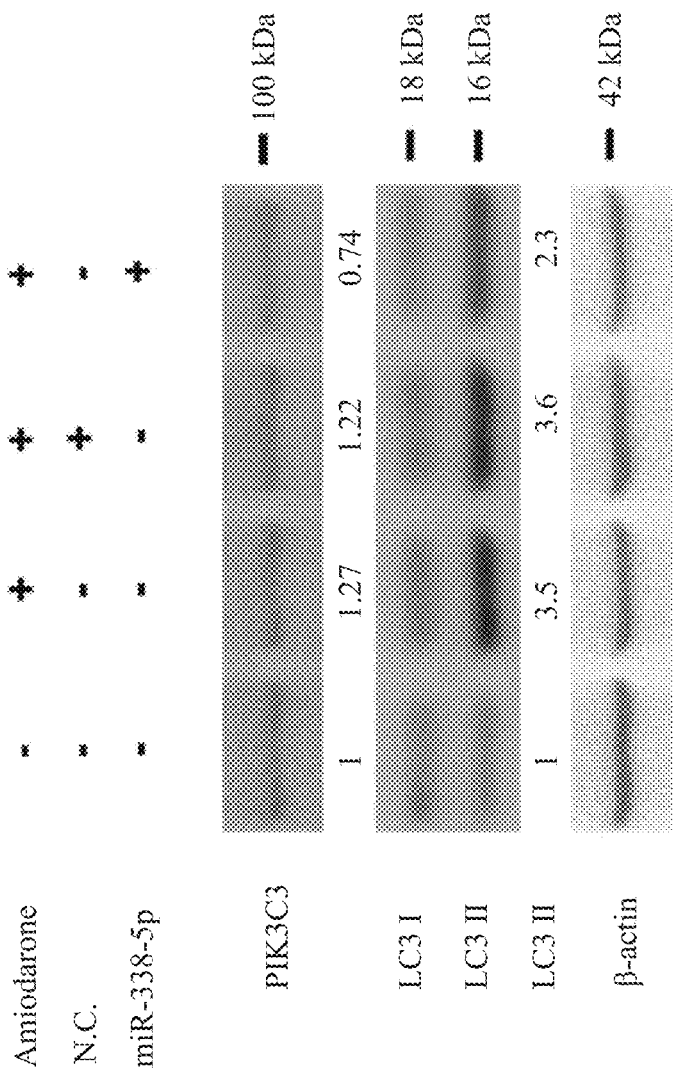
Figure 14C:
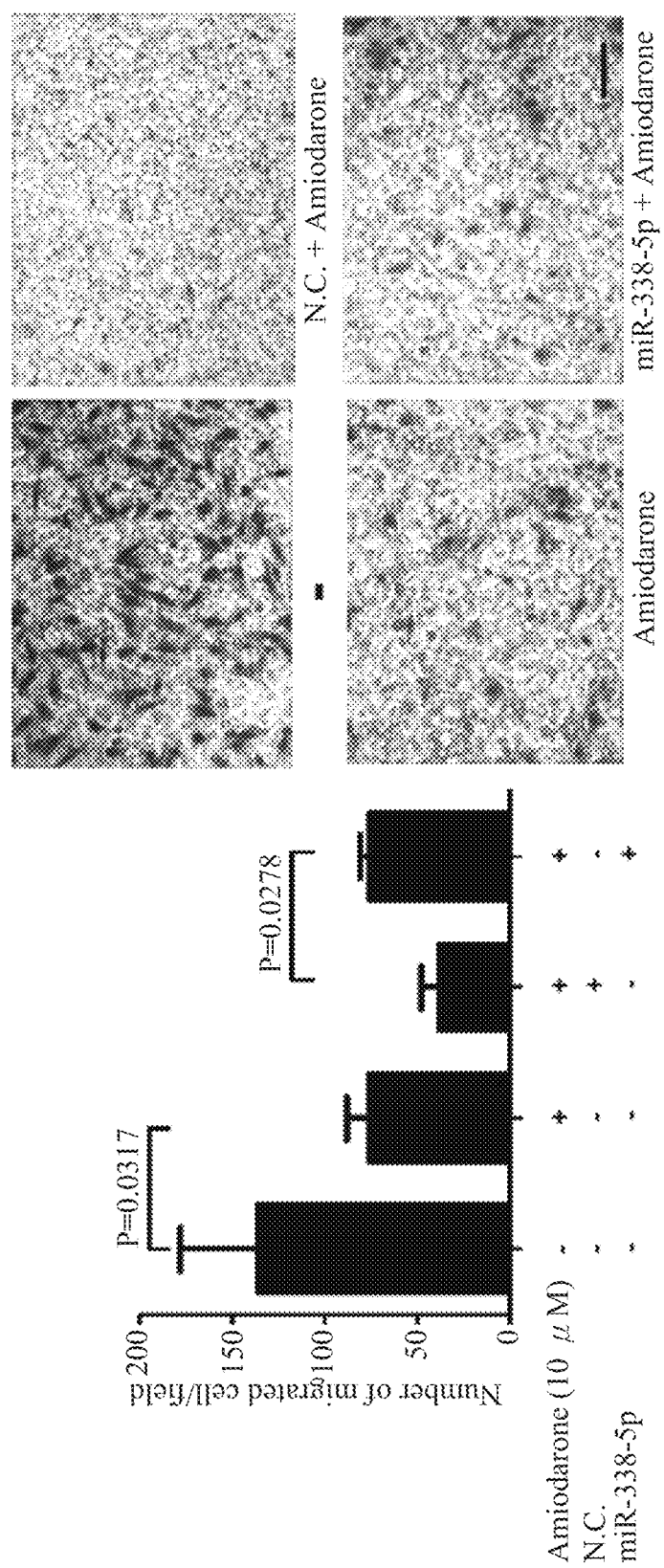
Figure 14D:
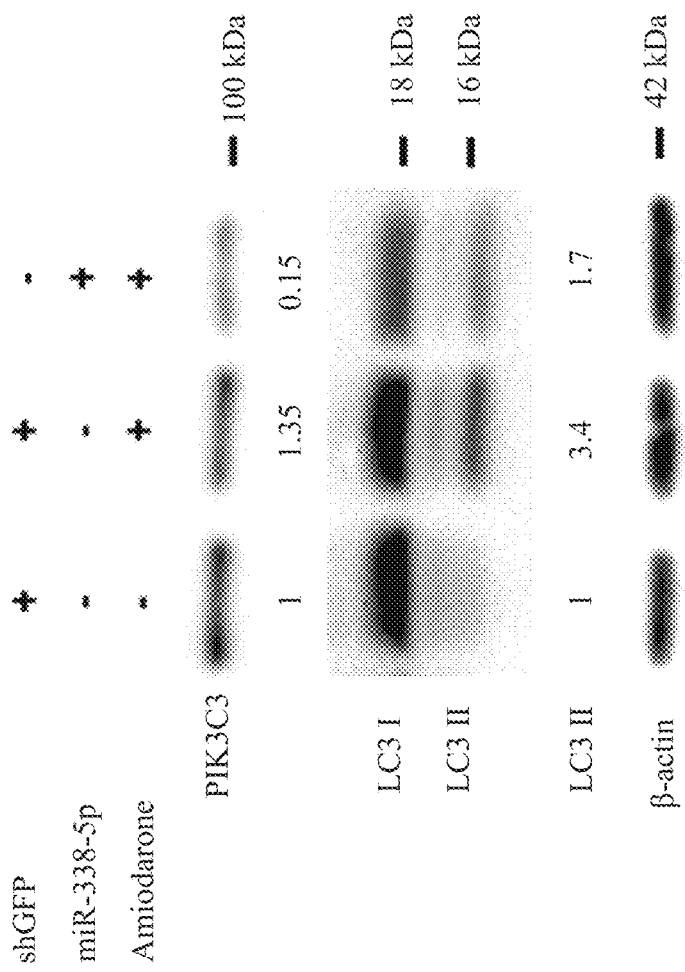
Figure 14E:
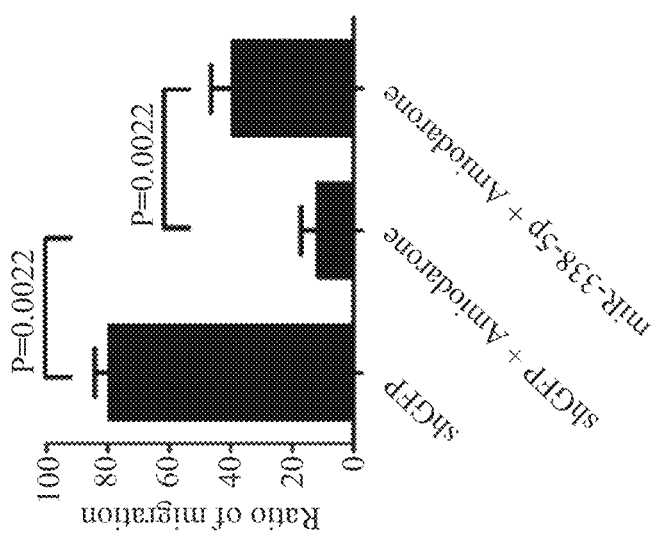
Figure 14E:
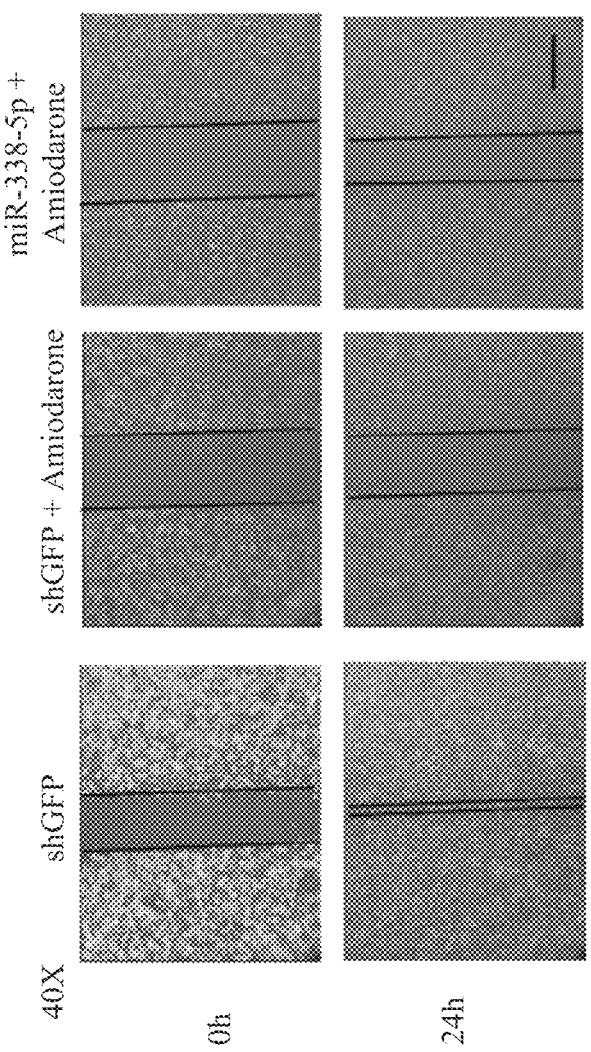
Figure 14F:
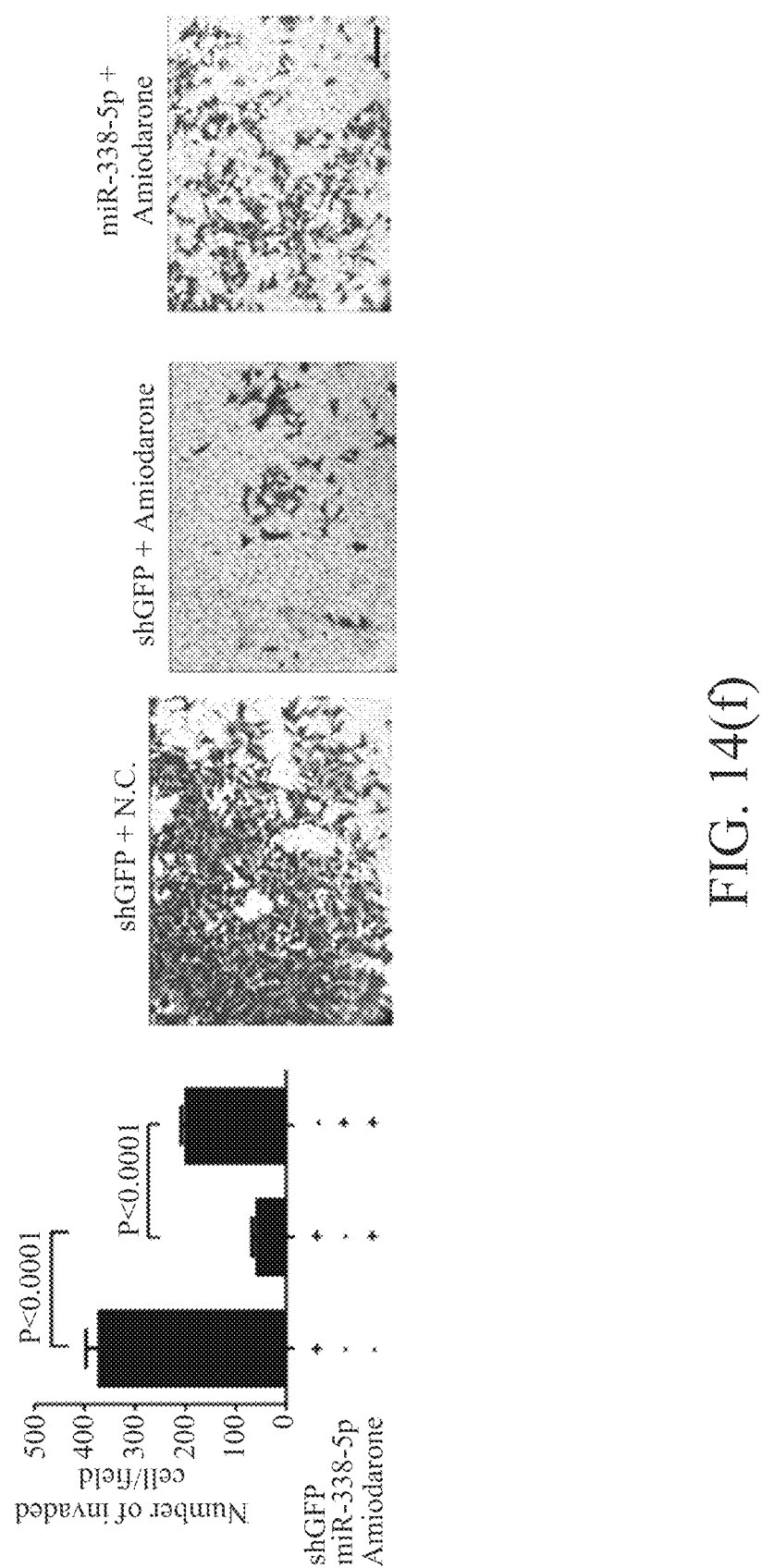

Example 7: Autophagy Involvement in miR-338-5p Induces the Migration and Invasion of CRC To clarify the mechanism(s) underlying miR-338-5p induced migration and invasion of CRC, the involvement of autophagy was assessed. Specifically, the LC3 puncta (microtubule associated protein 1A/1B-LC3) formation and LC3 type II (LC3-II) protein expression were examined in cells treated with amiodarone (an autophagy inducer) by immunofluorescent assay. Amiodarone treatment (10 µM) induced LC3 puncta formation (P<0.0001, Mann-Whitney test) as shown in FIG. 14(a) and activated LC3-II expression of CRC cells as shown in FIGS. 14(b) and 14(d). FIG. 14(c) and FIG. 14(e) show inhibition of cell migration, and FIG. 14(f) shows inhibition of cell invasion in amiodarone-treated cells that could be rescued in miR-338-5p-overexpressing cells.

Furthermore, suppression of PIK3C3 in miR-338-5p-overexpressing cells significantly inhibited the autophagy induced by amiodarone, as shown in FIGS. 14(a), 14(b) and 14(d). The results indicate that miR-338-5p induces migration and invasion of CRC cells through repression of autophagy.

Figure 15A:
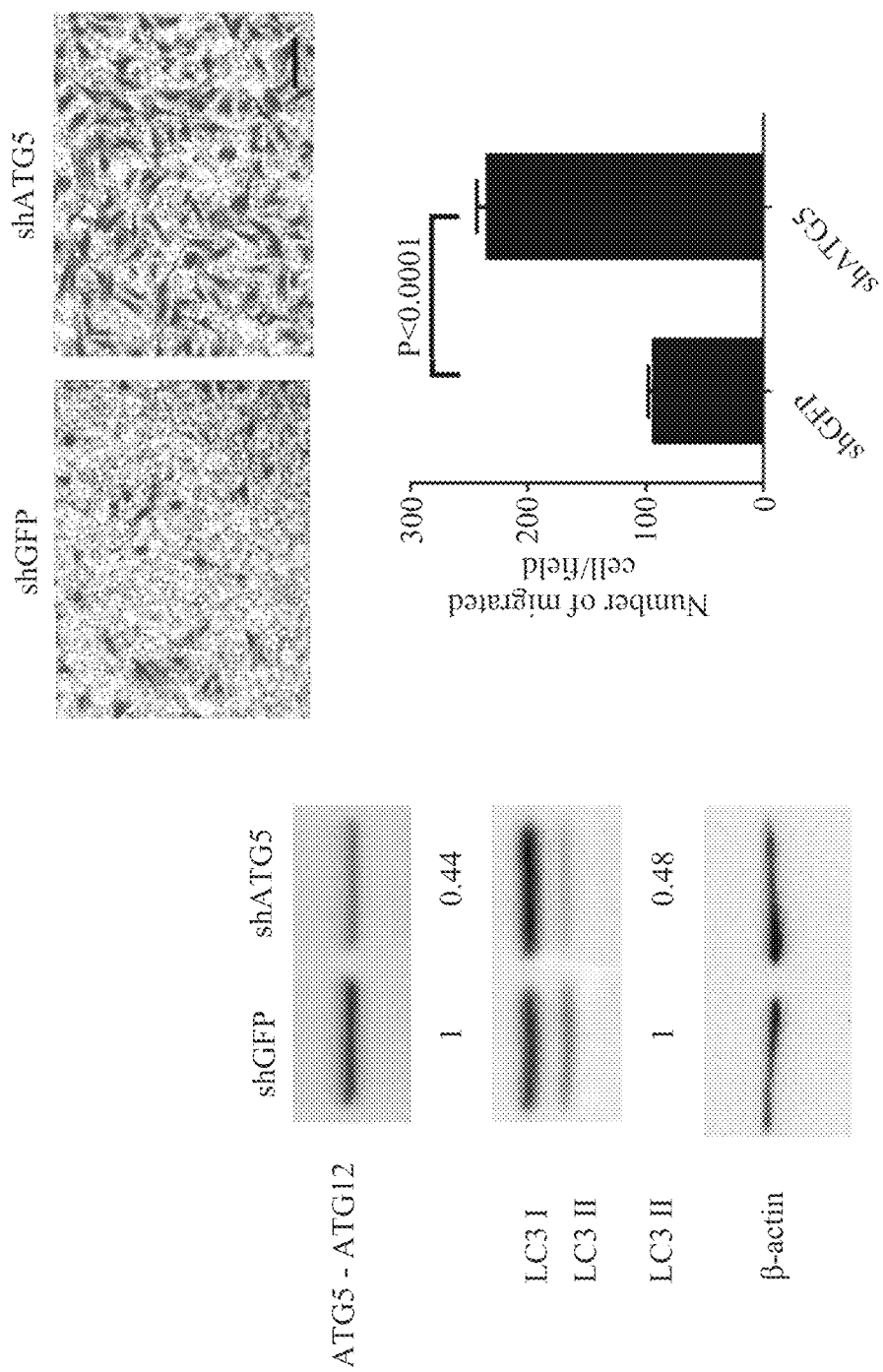
FIGS. 15(a) to 15(c) show the involvement of autophagy or EMT pathway in miR-338-5p-related CRC migration in vitro.
Figure 15B:
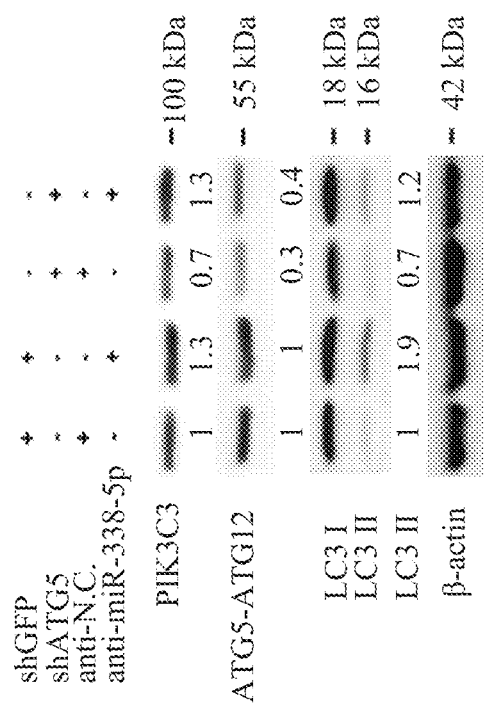
Figure 15B:
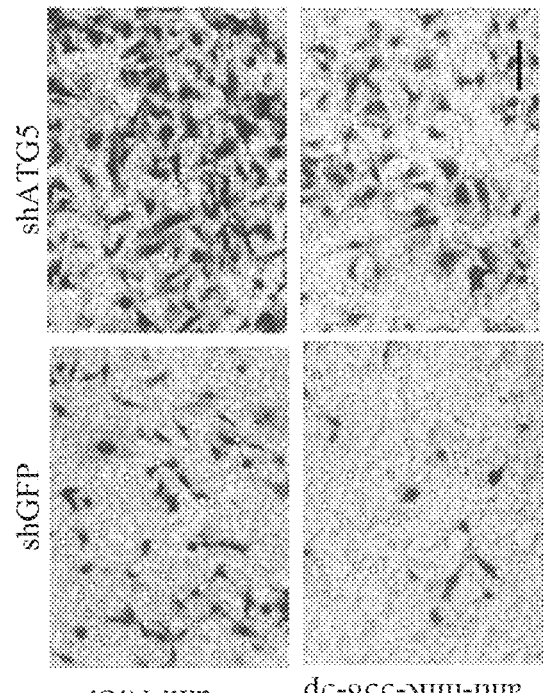
Figure 15B:
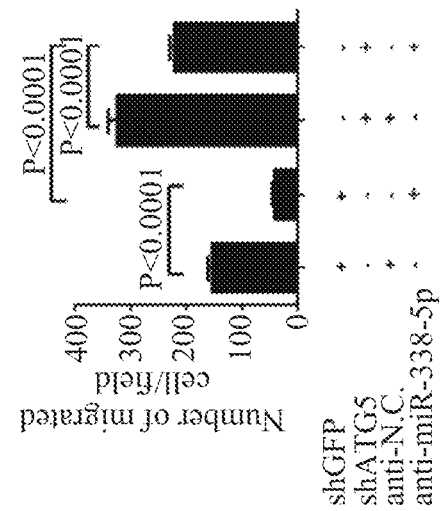

To confirm this observation, a shATG5 lentivirus was used to modulate autophagy in vitro. Knocking down of ATG5 in SW480 cells inhibited the autophagy activity (LC3 II) associated with increased cell migration, as shown in FIG. 15(a). When anti-miR-338-5p was transiently transfected, expression of PIK3C3 and LC3-II were restored, and migration of SW480 cells were inhibited (P<0.0001, t test). Silencing of ATG5 reversed the inhibited migration of SW480 cells transfected with anti-miR-338-5p (P<0.0001, t test). However, number of migrated cells observed with anti-miR-338-5p was even less than that of receiving shATG5 lentivirus infection only (P<0.0001, t test), as shown in FIG. 15(b), implying the existence of miR-338-5p independent mechanism(s) in the autophagy related cell migration. Therefore, miR-338-5p induces migration and invasion of CRC cells in part through inhibition of autophagy.

Figure 15C:
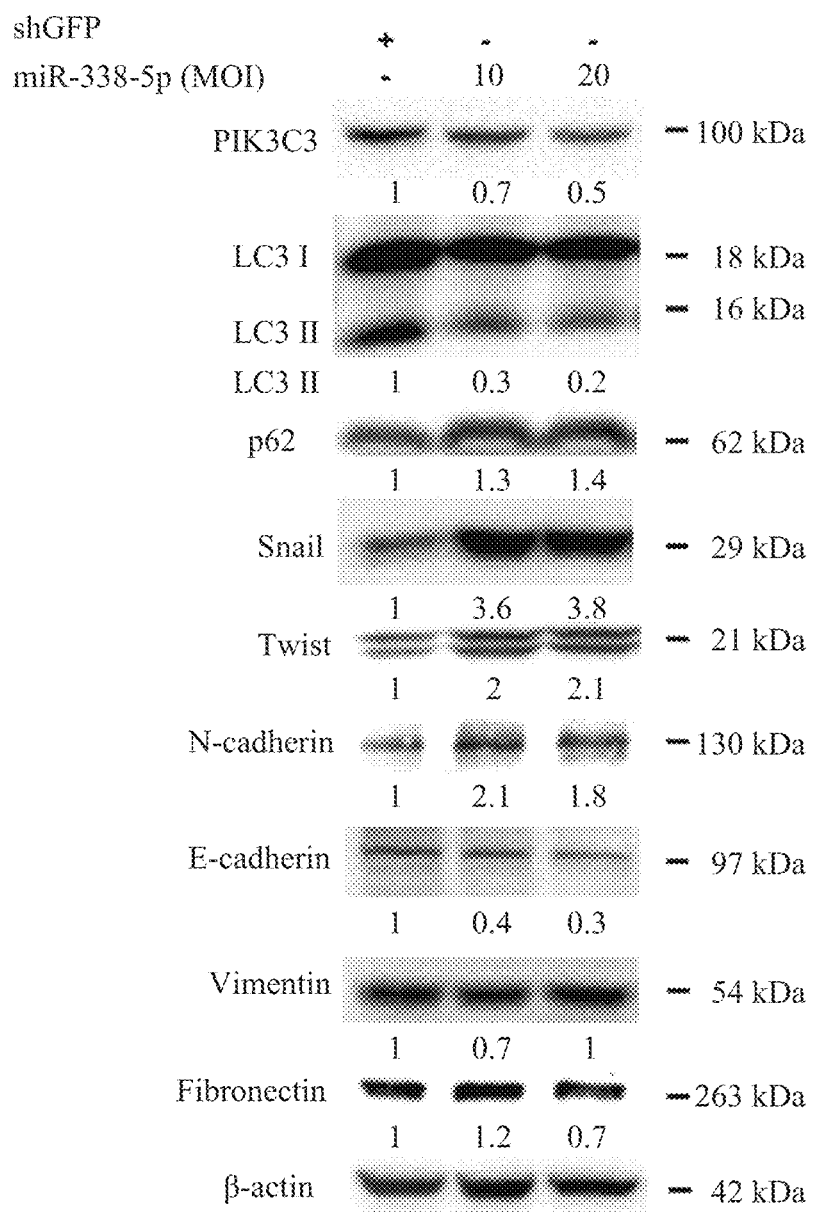

Moreover, HCT116 stable miR-338-5p-overexpression cell line was analyzed by Western blot. When miR-338-5p was overexpressed, both PIK3C3 and LC3 II protein expressions were inhibited together with increased p62 (SQSTM1), an autophagosome degradation marker. In addition, E-cadherin was down-regulated with up-regulated N-cadherin, Snail and Twist proteins, indicative of an EMT phenotype, as shown in FIG. 15(c). However, expressions of vimentin and fibronectin were not affected. The results implied that miR-338-5p could modulate EMT in conjunction with inhibition of autophagy. Altogether, PIK3C3-related autophagy contributes to part of miR-338-5p mediated CRC migration, invasion and metastasis in vitro.

The foregoing examples are used to exemplify the present disclosure. A person of ordinary skill in the art can conceive the other advantages of the present disclosure, based on the specification of the present disclosure. The present disclosure can also be implemented or applied as described in different examples. It is possible to modify and/or alter the examples for carrying out this disclosure without contravening its spirit and scope for different aspects and applications.

What is claimed is:

1. A method for assessing prognosis of colorectal cancer, comprising:

measuring, by a first pair of oligonucleotides comprising a sequence of SED ID NO. 1, a first expression level of at least one miRNA associated with the colorectal cancer in a cancer tissue from a subject in need thereof;

measuring, by a second pair of oligonucleotides comprising a sequence of SED ID NO. 4, a sequence of SED ID NO. 3, or a combination thereof, a second expression level of at least one target gene of the miRNA in the cancer tissue; and determining a ratio between the first expression level of the miRNA and the second expression level of the target gene as indicative of the prognosis of the colorectal cancer of the subject, wherein the at least one miRNA is miRNA-338-5p, wherein the target gene encodes phosphatidylinositol 3-kinase catalytic subunit type 3 (PIK3C3); and wherein the ratio determined as greater or equal to about 4.405 or a predetermined value indicates poor prognosis of colorectal cancer.

2. The method of claim 1, wherein the prognosis is indicative of metastatic potential of the colorectal cancer, a tumor stage of the colorectal cancer, or survival of the subject.

3. The method of claim 2, wherein the metastatic potential of the colorectal cancer is the metastatic potential to at least one of liver, lung, lymph nodes, peritoneum, abdominal wall, small intestine, stomach, pancreas, biliary tract, spleen, kidney, uterus, ovary, fallopian tube, head, neck, brain, respiratory organs, skin, bone, and distant soft tissue.

4. The method of claim 2, wherein the survival is recurrence-free survival, disease-free survival, disease-specific survival, overall survival or metastasis-free survival.

5. The method of claim 1, further comprising determining a therapy based on the prognosis and treating the subject with the therapy.

6. The method of claim 5, wherein the therapy comprises surgery, radiation therapy, chemotherapy, targeted therapy, immunotherapy, hyperthermia or a combination thereof.

7. The method of claim 1, wherein the measurement of the first expression level and the second expression level includes amplification or hybridization.

8. The method of claim 1, wherein at least one of the first expression level and the second expression is measured by real-time PCR.

* * * * *